(12) United States Patent
Schramm et al.

(10) Patent No.: US 9,290,501 B2
(45) Date of Patent: Mar. 22, 2016

(54) METHODS, ASSAYS AND COMPOUNDS FOR TREATING BACTERIAL INFECTIONS BY INHIBITING METHYLTHIOINOSINE PHOSPHORYLASE

(75) Inventors: Vern L. Schramm, New Rochelle, NY (US); Keith Clinch, Lower Hutt (NZ); Peter Charles Tyler, Wellington (NZ); Gary Brian Evans, Lower Hutt (NZ); Richard Hubert Furneaux, Wellington (NZ)

(73) Assignees: Albert Einstein College of Medicine, Inc., Bronx, NY (US); Victoria Link Limited, Wellington (NZ)

( * ) Notice: Subject to any disclaimer, the term of this patent is extended or adjusted under 35 U.S.C. 154(b) by 171 days.

(21) Appl. No.: 13/884,298

(22) PCT Filed: Nov. 28, 2011

(86) PCT No.: PCT/US2011/062208
§ 371 (c)(1),
(2), (4) Date: Jun. 19, 2013

(87) PCT Pub. No.: WO2012/074912
PCT Pub. Date: Jun. 7, 2012

(65) Prior Publication Data
US 2013/0274220 A1     Oct. 17, 2013

Related U.S. Application Data

(60) Provisional application No. 61/458,660, filed on Nov. 29, 2010.

(51) Int. Cl.
| | | |
|---|---|---|
| *A01N 43/04* | (2006.01) | |
| *A61K 31/70* | (2006.01) | |
| *C07D 487/04* | (2006.01) | |
| *A61K 31/7076* | (2006.01) | |
| *A61K 31/7064* | (2006.01) | |
| *A61K 31/7042* | (2006.01) | |
| *A61K 31/7052* | (2006.01) | |
| *A61K 31/708* | (2006.01) | |
| *A61K 31/706* | (2006.01) | |
| *A61K 31/00* | (2006.01) | |
| *A61K 31/519* | (2006.01) | |
| *A61K 31/7068* | (2006.01) | |
| *A61K 45/06* | (2006.01) | |
| *C12Q 1/48* | (2006.01) | |

(52) U.S. Cl.
CPC .............. *C07D 487/04* (2013.01); *A61K 31/00* (2013.01); *A61K 31/519* (2013.01); *A61K 31/706* (2013.01); *A61K 31/708* (2013.01); *A61K 31/7042* (2013.01); *A61K 31/7052* (2013.01); *A61K 31/7064* (2013.01); *A61K 31/7068* (2013.01); *A61K 31/7076* (2013.01); *A61K 45/06* (2013.01); *C12Q 1/48* (2013.01)

(58) Field of Classification Search
None
See application file for complete search history.

(56) References Cited

U.S. PATENT DOCUMENTS

| | | | |
|---|---|---|---|
| 5,985,848 A * | 11/1999 | Furneaux et al. | ........... 514/44 R |
| 6,066,722 A | 5/2000 | Furneaux et al. | |
| 6,228,847 B1 | 5/2001 | Furneaux et al. | |
| 6,492,347 B2 | 12/2002 | Furneaux et al. | |
| 6,693,193 B1 | 2/2004 | Furneaux et al. | |
| 6,803,455 B2 | 10/2004 | Furneaux et al. | |
| 7,022,852 B2 | 4/2006 | Furneaux et al. | |
| 7,098,334 B2 | 8/2006 | Furneaux et al. | |
| 7,109,331 B2 | 9/2006 | Furneaux et al. | |
| 7,211,653 B2 | 5/2007 | Furneaux et al. | |
| 7,211,677 B2 | 5/2007 | Furneaux et al. | |
| 7,390,890 B2 | 6/2008 | Furneaux et al. | |
| 7,405,297 B2 | 7/2008 | Furneaux et al. | |
| 7,655,795 B2 | 2/2010 | Evans et al. | |
| 8,173,662 B2 | 5/2012 | Evans et al. | |
| 8,183,019 B2 | 5/2012 | Lenz et al. | |
| 8,283,345 B2 | 10/2012 | Evans et al. | |
| 8,383,636 B2 | 2/2013 | Clinch et al. | |
| 2009/0233948 A1 | 9/2009 | Evans et al. | |
| 2009/0325986 A1 | 12/2009 | Furneaux et al. | |
| 2010/0062995 A1 | 3/2010 | Schramm et al. | |
| 2010/0222370 A1 | 9/2010 | Schramm et al. | |
| 2011/0086812 A1 | 4/2011 | Schramm et al. | |
| 2011/0092521 A1 | 4/2011 | Furneaux et al. | |
| 2011/0130412 A1 | 6/2011 | Clinch et al. | |
| 2011/0190265 A1 | 8/2011 | Schramm et al. | |
| 2012/0157479 A1 | 6/2012 | Evans et al. | |

FOREIGN PATENT DOCUMENTS

WO    WO 2009/082247 A1 *    7/2009    ........... C07D 471/04

OTHER PUBLICATIONS

Murkin et al. Bioorganic & Medicinal Chemistry Letters (2008), vol. 18, pp. 5900-5903.*

* cited by examiner

*Primary Examiner* — Patrick Lewis
(74) *Attorney, Agent, or Firm* — Amster, Rothstein & Ebenstein LLP

(57) ABSTRACT

The present invention discloses methods for treating bacterial infections in a subject comprising administering to the subject a sub-growth inhibiting amount of a 5'-methylthioinosine phosphorylase (MTIP) inhibitor, as well as assays for identifying such inhibitors, and compounds and pharmaceutical compositions comprising the inhibitors.

12 Claims, 3 Drawing Sheets

```
1YR3    6   -FSHNPLFCIDIIKTYKPD-FTPRVAFILGSGLGALAD-QIENAVAISYEKLPGFPVSTVHGHAGELVLGHLQGVPVVCMKGR------GHFYEGRGM
1N3I    9   --DELARRAAQVIADRTG-IGEHDVAVVLGSWLPAVAALGSPTTVLPQAELPGFVPPTAAGHAGELLSVPIGAHRVLVLAGR------IHAYEGHDL
3KHS    3   -DYDLAKETAAWLNKQLQ--IRPVLGIVCGSGLGKIGD-SLETSITVAYSDIPNFPVGSVKGHAGSLIFGSVNGVSCVCMKGR------FHLYEGHTA
2P4S    90  YTYDTLQEIATYLLERTE--LRPKVGIICGSGLGTLAE-QLTDVDSFDYETIPHFPVSTVAGHVGRLVFGYLAGVPVMCMQGR------FHHYEGYPL
1VMK    1   -MMKKIEEARTFISERTN--LSPDILILGSGFGPFIE--KVEDPVIIDYKDIPHFPQPTVEGHSGKLVFGRISDKPVMIMAGR------FHLYEGHDP
1A9T    5   YTYEDYQDTAKWLLSHTE--QRPQVAVICGSGLGGLVN-KLTQAQTFDYSEIPNFPESTVPGHAGRLVFGILNGRACVMMQGR------FHMYEGYPF
1RR6    5   YTYEDYKNTAEWLLSHTK--HRPQVAIICGSGLGGLTD-KLTQAQIFDYSEIPNFPRSTVPGHAGRLVFGFLNGRACVMMQGR------FHMYEGYPL
3OZB    17  -------------VYAIIG--GTGLTQLEGLTLSESL---PIETPYGAPS---APLQRGRYAGREVLFLARHGHPHRFPPHQV------
1V4N    7   ------------------EKASIGIIG--GSGLYDPQILTNVKEI---KVYTPYGEPS---DNIILGELEGRKVAFLPRHGRGHRIPPHKI----
1K27    11  -----------KIGIIGGTGLDD-PE--ILEGRTEK----YDTPFGKPS---DALILGKIKNVDCVLLARHGRQHTIMPSKV----
1WTA    3   ---EITR--PPG---VRAHVGVIG---GSGLYDPGIVENPVEV---KVSTPYGNPS---DFIVVGDVAGVKVAFLPRHGRGHRIPPHAI----
2A8Y    2   ---IEQN------EKASIGIIGGSGLYDP-G--IFSESKEI----KVYTPYGQPS---DFITIGKIGNKSVAFLPRHGRGHRIPPHKI----

1YR3    95  TIMTDAIRTFKLLGCELLFCTNAAGSLRPEVGAGSIVALKDHINTM---PGTPMVGL-NDDRFGER FTSLANAYDAEYRALLQKVAKEEGFP--LTEG
1N3I    98  RYVVHPVRAARAAGAQIMVLTNAAGGLRADLQVGQPVLISDHLNLTA--RSPLVGG------EFVDLTDAYSPRLRELARQSDP------QLAEG
3KHS    91  ARATFPMRVFKALGVKIVVLTNAAGGLNPSYRPGDFMVVRDHINLPGLAGANPLTGP-NDDTEGER FPSMTSVYDKTLRKYAISAARELGMSYATHEG
2P4S    179 AKCAMPVRVMHLIGCTHLIATNAAGGANPKYRVGDIMLIKDHINLMGFAGNNPLQGP-NDERFGPR FGMANTYDPKLNQQAKVIARQIGIENELREG
1VMK    89  ATVAFPVYLAKYVGVGKGVVVTNAAGAINPEFKPGEIILVRDIINFMF---RNPLRGP-NDEKIGPR FPDMSSVVDPEWARKIQERLS------LKEG
1A9T    94  WKVTFPVRVFRLLGVETLVVTNAAGGLNPNFEVGDIMLIRDHINLPGFSGENPLRGP-NEERFGVR FPAMSDAYDRDMRQKAHSTWKQMGEQRELQEG
1RR6    94  WKVTFPVRVFHLLGVDTLVVTNAAGGLNPKFEVGDIMLIRDHINLPGFSGQNPLRGP-NDERFGDR FPAMSDAYDRTMRQALSTWKQMGEQRELQEG
3OZB    79  -NYRANLWALKQAGAEAVIAVNAVGGIHAAMGTGHLCVPHQLIDYTSG-REHTYFAG---DIEHVThIDFSHPYDEPLRQRLIEALRALGL-AHSSHG
1V4N    72  -NYRANIWALKSLGVKWVIAVSAVGSLRLDYKPGDFVVPNQFIDMTKG-RTYTFFDG-----PTVAhVSMADPFCEHLRSIILDSAKDLGI-TTHDKG
1K27    73  -NYQANIWALKEEGCTHVIVTTACGSLREEIQPGDIVIIDQFIDRTTM-RPQSFYDGSHSCARGVChIPMAEPFCPKTREVLIETAKKLGL-RCHSKG
1WTA    75  -NYRANIWALKALGVRWVISVSAVGSLRMDYRPGDFVVPDQFIDMTKNRRHYTFYD-----GPVTVhVSMADPFCEDLRQRLIDSGRRLGY-TVHERG
2A8Y    71  -NYRANIWALKELGVRWVISVSAVGSLRMDYKLGDFVIPDQFIDMTKN-REYSFFD-----GPVVAhVSMADPFCNSLRKLAIETAKELNI-KTHESG

1YR3    190 VFVSYPGPNFETAAEIRMMQI-IGGDVVGMSVVPEVISARHCDLKVVAVSAITNMAEGL--SDVKLSHAQTLAAAELSKQNFINLICGFLRKIA---
1N3I    182 VYAGLPGPHYETPAEIRMLQT-LGADLVGMSTVHETIAARAAGAEVLGVSLVTNLAAGI--TGEPLSHAEVLAAGAASATRMGALLADVIARF----
3KHS    191 VYCCVNGPSFETPAECKILRL-MGSDAVGMSTAPETIVAKHGGMRCLAVSLISNVIASNCETPAEPTHEEVLRAGEEASARMTALVKLVIEKIRGE-
2P4S    279 VYTCLGGPNFETVAEVKMLSM-LGVDAIGMSTVHEIITARHCGMTCFAFSLITNMCTMSYEEEEHCHDSIVGVGKNREKTLGEFVSRIVKHIHYEA-
1VMK    179 VYIGVLGPSYETPAEIRVFEK-LGADLVGMSTVPEVIAAKHCGLKVVVFSCVTNMAAG---ITHGRLSHEEVVRTTKMAQGKIEKALTTAVEVF---
1A9T    194 TYMLGGPNFETVAECRLLRN-LGADAVGMSTVPEVIVARHCGLRVFGFSLITNKVIMDTESQGKANHEEVLAAGKQAAQKLEQFVSLLMASI----
1RR6    194 TYMVAGPSFETVAECRVLQK-LGADAVGMSTVPEVIVARHCGLRVFGFSLITNKVIMDYESLEKANHEEVLAAGKQAAQKLEQFVSILMASI----
3OZB    174 VYACTQGPRLETVAEIARLER-DGNDIVGMTGMPEAALARELDLPYACLALVVNPAAG-K--SAGIITMAEIEQALHDGIGKVREVLARVLA----
1V4N    165 TYICIEGPRFSTRAESIVWKEVFKADIIGMTLVPEVNLACEAEMCYSVIGMVTDYDV-F--ADIPVTAEEVTKVMAENTAKVKKLLYEVIRRLP--
1K27    171 TMVTIEGPRFSSRAESFMFRT-WGADVINMTTVPEVVLAKEAGICYASIAMATDYDC-WKEHEEAVSVDRVLKTLKENANKAKSLLLTTIPQIGSTE
1WTA    169 TYCIEGPRFSTRAESRVWKDVFKADIIGMTLVPEINLACEAQLCYATLAMVTDYDV-W--ADRPVTAEEVERVMISNVERARRMLYDVIPKLAGE--
2A8Y    164 TYICIEGPRFSTRAESRTWREVYKADIIGMTLVPEVNLACEAQMCYATIAMVTDYDV-F--AEIPVTAEEVTRVMAENTEKAKKLLYALIQKLPEKP
                    *                                                                             *
```

FIGURE 2

METHODS, ASSAYS AND COMPOUNDS FOR TREATING BACTERIAL INFECTIONS BY INHIBITING METHYLTHIOINOSINE PHOSPHORYLASE

CROSS-REFERENCE TO RELATED APPLICATIONS

This application is a U.S. national stage entry under 35 U.S.C. X371 of PCT International Patent Application No. PCT/US2011/062208, filed Nov. 28, 2011, which claims priority to U.S. Provisional Patent Application No. 61/458,660, filed Nov. 29, 2010, the contents of which are incorporated herein by reference into the subject application.

STATEMENT OF GOVERNMENT SUPPORT

This invention was made with government support under Grant No. GM041916 awarded by the National Institutes of Health. The government has certain rights in the invention.

FIELD OF THE INVENTION

The present invention relates to methods, assay, compounds and compositions for treating infections caused by bacteria that use 5'-methylthioinosine phosphorylase (MTIP) in a quorum sensing pathway, such as *Pseudomonas aeruginosa*.

BACKGROUND OF THE INVENTION

Throughout this application various publications are referred to by Arabic numerals in parentheses. Full citations for these references may be found at the end of the specification immediately preceding the claims. The disclosures of these publications are hereby incorporated by reference in their entireties into the subject application to more fully describe the art to which the subject application pertains.

*Pseudomonas aeruginosa* is a Gram-negative bacterium found in a wide range of environments including water, soil, and mammals (1). It is a major opportunistic human pathogen, infecting burns, and lungs in cystic fibrosis (2). Compromised immune systems and extended hospitalization are correlated with infections, making *P. aeruginosa* the causative agent of approximately 15% of all hospital infections (2, 3). *P. aeruginosa* infections are difficult to treat since the bacterium has multiple antimicrobial resistance mechanisms (4). Chronic infections can be severe in patients with cystic fibrosis, causing high rates of morbidity and mortality (5, 6). *P. aeruginosa* infections are related to quorum sensing (QS) pathways, which regulate virulence factors and biofilm formation.

Signal molecules of QS include N-acyl-homoserine lactones (AHLs). The concentration of AHLs increases during bacterial growth to allow AHL binding to specific receptors and the regulation of target genes. In *P. aeruginosa*, the las and rhl QS systems use AHLs of 3-oxo-$C_{12}$-homoserine lactone and $C_4$-homoserine lactone as signal molecules, respectively. Microarray studies on *P. aeruginosa* indicated that QS regulated 3-7% of the total open reading frames (7-9). Deletion of single or multiple QS genes reduced the virulence of *P. aeruginosa* in mouse studies, indicating a strong correlation between the QS system and *P. aeruginosa* pathogenesis (10-15). Quorum sensing blockade does not affect bacterial growth and is therefore expected to attenuate the virulence of infection without causing drug resistance (16, 17).

Potential therapeutic targets in the QS system include enzymes involved in the formation of AHLs that act as signaling molecules and as virulence factors in *P. aeruginosa* (16). AHLs are synthesized from S-adenosylmethionine (SAM) and acylated-acyl carrier protein by AHL synthase with 5'-methylthioadenosine (MTA) as a by-product. MTA is recycled to ATP and methionine for SAM recycling (17). In bacteria, 5'-methylthioadenosine nucleosidase (MTAN) is the normal path to produce adenine and 5-methylthioribose-α-D-1-phosphate (MTR-1-P) from MTA for recycling. Transition state analogue inhibitors of *E. coli* and *V. cholerae* MTAN disrupted quorum sensing and reduced biofilm formation, supporting MTAN as a target for QS (17).

With the growing global threat of multi-drug resistance, nonconventional antibacterial discovery approaches are required that are nonlethal to bacteria where the potential to develop drug resistance is assumed to be less significant. The present invention addresses that need for infections caused by bacteria such as *Pseudomonas aeruginosa* that use 5'-methylthioinosine phosphorylase (MTIP) in a quorum sensing pathway.

SUMMARY OF THE INVENTION

The invention provides methods for treating infections caused by bacteria that use 5'-methylthioinosine phosphorylase (MTIP) in a quorum sensing pathway comprising administering to a subject having the infection a sub-growth inhibiting amount of a 5'-methylthioinosine phosphorylase (MTIP) inhibitor. The invention also provides pharmaceutical compositions comprising a sub-bacterial-growth inhibiting amount of a 5'-methylthioinosine phosphorylase (MTIP) inhibitor and a pharmaceutically acceptable carrier.

The invention also provides methods for determining whether or not a compound is a candidate for treating an infection caused by bacteria that use 5'-methylthioinosine phosphorylase (MTIP) in a quorum sensing pathway, the method comprising determining whether or not the compound inhibits MTIP, wherein a compound that inhibits MTIP is a candidate for treating an infection caused by bacteria that use MTIP in a quorum sensing pathway and wherein a compound that does not inhibit MTIP is not a candidate for treating an infection caused by bacteria that use MTIP in a quorum sensing pathway.

BRIEF DESCRIPTION OF THE FIGURES

FIG. 2. Structure-based sequence alignment. Protein are listed by PDB ID. The top 7 sequences are PNPs, the bottom 4 sequences are MTAPs, and PaMTIP is 3OZB. The conserved residues in the phosphate binding site of PNPs (bold font) and MTAPs (bold font) are indicated. The conserved residues in the purine binding site of PNPs and MTAPs are underlined. The conserved Phe ("F") and His ("H") in ribose-binding site of PNPs are in italics. The conserved His and small hydrophobic amino acid in the (methylthio)ribose-binding site of MTAPs are in lower case letters. The residues in columns marked by * are conserved (but not identical) in all species. The Leu ("L") of PaMTIP is not conserved in either MTAPs or PNPs and is in underlined italic. The PDB IDs are as follows: 1YR3, *E. coli* PNP II (SEQ ID NO:1); 1N3I, *Mycobacterium tuberculosis* PNP (SEQ ID NO:2); 3 KHS, Grouper Iridoviurs PNP (SEQ ID NO:3); 2P4S, *Anopheles Gambia* PNP (SEQ ID NO:4); 1VMK, *Thermotoga maritime* PNP (SEQ ID NO:5); 1A9T, bovine PNP (SEQ ID NO:6);

1RR6, human PNP (SEQ ID NO:7); 3OZB, PaMTIP (SEQ ID NO:8); 1V4N, *Sulfolobus tokodaii* MTAP (SEQ ID NO:9); 1K27, human MTAP (SEQ ID NO:10); 1WTA, *Aeropyrum pernix* K1 MTAP (SEQ ID NO:11); 2A8Y, *Sulfolobus solfataricus* MTAP (SEQ ID NO:12).

Figure 3:
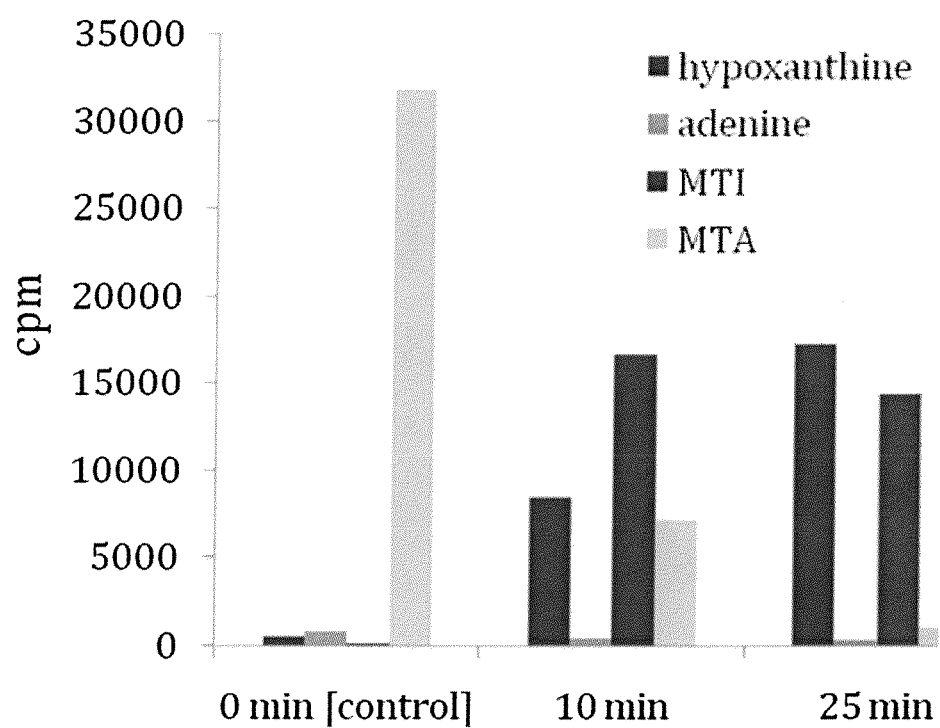

FIG. 3. Metabolism of [8-$^{14}$C]MTA in *P. aeruginosa*. *P. aeruginosa* lysate was incubated with [8-$^{14}$C]MTA for 0, 10, and 25 min, respectively. The $^{14}$C-metabolites MTA, MTI, adenine and hypoxanthine were purified using RP-HPLC and quantitated by scintillation counting. Bar graphs from left to right of figure for hypoxanthine, adenine, MTI and MTA.

DETAILED DESCRIPTION OF THE INVENTION

The invention provides a method for treating an infection caused by bacteria that use 5'-methylthioinosine phosphorylase (MTIP) in a quorum sensing pathway comprising administering to a subject having the infection a sub-growth inhibiting amount of a 5'-methylthioinosine phosphorylase (MTIP) inhibitor.

The bacteria can be, for example, *Pseudomonas aeruginosa, Pseudomonas syringae* or *Xanthomonas campestris.*

The subject can be, for example, an animal, such as a mammal, such as a primate, such as a human, or a plant.

For example, in one embodiment, the bacteria is *Pseudomonas aeruginosa* and the subject is a human. In another embodiment, for example, the bacteria is *Pseudomonas syringae* or *Xanthomonas campestris* and the subject is a plant.

As used herein, to treat a bacterial infection in a subject means to reduce the virulence of the bacteria in the subject. The term "bacterial infection" shall mean any deleterious presence of bacteria in the subject.

The term "sub-growth inhibiting amount" of a MTIP inhibitor as used herein means an amount of the inhibitor, which when contacted with a population of bacteria, does not reduce the growth of the bacterial population. Preferably, the sub-growth inhibiting amount of the MTIP inhibitor inhibits quorum sensing in the bacteria. Preferably, the sub-growth inhibiting amount of the MTIP inhibitor is effective to reduce virulence of the bacteria without promoting the development of resistance by the bacteria to the MTIP inhibitor.

The term "quorum sensing" as used herein refers to the process by which bacteria produce and detect signaling molecules with which to coordinate gene expression and regulate processes beneficial to the microbial community. The term "inhibit quorum sensing" as used herein means altering this process such that coordination of gene expression and process regulation in microbial communities are impaired or prevented.

The invention also provides a pharmaceutical composition or an agrochemical composition comprising a sub-bacterial-growth inhibiting amount of a 5'-methylthioinosine phosphorylase (MTIP) inhibitor and a pharmaceutically or agrochemically acceptable carrier. Preferably, the pharmaceutical composition is formulated in dosage form. Preferably, the sub-bacterial-growth inhibiting amount of the MTAN inhibitor inhibits quorum sensing in bacteria. Preferred bacteria include, for example, *Pseudomonas aeruginosa, Pseudomonas syringae* and *Xanthomonas campestris.*

As used herein, "pharmaceutically acceptable carriers" are materials that (i) are compatible with the other ingredients of the composition without rendering the composition unsuitable for its intended purpose, and (ii) are suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include any of the standard pharmaceutical carriers such as phosphate buffered saline solutions, water, and emulsions such as oil/water emulsions and microemulsions.

Definitions as Applied to MTIP Inhibitors:

The term "alkyl" is intended to include straight- and branched-chain alkyl groups, as well as cycloalkyl groups and having up to 30 carbon atoms, and includes any $C_1$-$C_{25}$, $C_1$-$C_{20}$, $C_1$-$C_{15}$, $C_1$-$C_{10}$, or $C_1$-$C_6$ alkyl group. Cycloalkyl groups may have one or two carbon atoms substituted by a nitrogen, oxygen or sulfur atom. The same terminology applies to the non-aromatic moiety of an aralkyl radical. Examples of alkyl groups include, but are not limited to: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group and 1-methyl-2-ethylpropyl group. Examples of cycloalkyl group include cyclopropyl, cyclobutyl, cyclopentyl, cyclohexyl, cycloheptyl, adamantly, 2-tetrahydrofuranyl, 2-thietaneyl, 3-piperidinyl, 2-pyrrolidinyl and 4-thiacyclohexanyl.

The term "alkenyl" means any hydrocarbon radical having at least one double bond, and having up to 30 carbon atoms, and includes any $C_2$-$C_{25}$, $C_2$-$C_{20}$, $C_2$-$C_{15}$, $C_2$-$C_{10}$, or $C_2$-$C_6$ alkenyl group, as well as cycloalkenyl groups, and is intended to include both straight- and branched-chain alkenyl groups. The same terminology applies to the non-aromatic moiety of an aralkenyl radical. Examples of alkenyl groups include but are not limited to: ethenyl group, prop-1-en-1-yl group, prop-2-en-1-yl group, prop-1-en-2-yl group, cis-but-2-en-1-yl group, trans-but-2-en-1-yl group, but-3-en-1-yl group, but-1-en-1-yl group, but-3-en-2-yl group, pent-4-en-1-yl group, 2-methyl-but-3-en-2-yl group, hex-5-en-1-yl group, cyclohex-1-enyl group, cyclohex-2-enyl group and cyclohex-3-enyl group The term "alkynyl" means any hydrocarbon radical having at least one triple bond, and having up to 30 carbon atoms, and includes any $C_2$-$C_{25}$, $C_2$-$C_{20}$, $C_2$-$C_{15}$, $C_2$-$C_{10}$, or $C_2$-$C_6$ alkynyl group, and is intended to include both straight- and branched-chain alkynyl groups. The same terminology applies to the non-aromatic moiety of an aralkynyl radical. Examples of alkynyl groups include but are not limited to: ethynyl group, prop-1-yn-1-yl group, prop-2-yn-1-yl group, but-1-yn-1-yl group, but-2-yn-1-nyl group, but-3-yn-1-yl group, pent-1-yn-1-yl group, 3,3-dimethyl-but-1-yn-1-yl group, 2-methyl-but-3-yn-2-yl group and hex-1-yn-1-yl group.

The term "aryl" means an aromatic radical having 1 to 18 carbon atoms and includes heteroaromatic radicals. Examples include monocyclic groups, as well as fused groups such as bicyclic groups and tricyclic groups. Examples include but are not limited to: phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

The term "aralkyl" means an alkyl radical having an aryl substituent.

The term "aralkenyl" means an alkenyl radical having an aryl substituent.

The term "alkoxy" means an hydroxy group with the hydrogen replaced by an alkyl group.

The term "halogen" includes fluorine, chlorine, bromine and iodine.

The term "prodrug" as used herein means a pharmacologically acceptable derivative of the MTIP inhibitor, such that an in vivo biotransformation of the derivative gives the MTIP inhibitor. Prodrugs of MTIP inhibitors may be prepared by modifying functional groups present in the compounds in such a way that the modifications are cleaved in vivo to give the parent compound.

As used herein, the structural formulae showing the "wedge" notation, e.g.:

are intended to represent pure enantiomeric forms of a trans isomer. Similarly, the structural formulae showing the "rectangular" notation, e.g.:

are intended to represent racemic mixtures of trans isomers.

It will be appreciated that the representation of the compound of the invention where B is a hydroxy group, is of the enol-type tautomeric form of a corresponding amide, and this will largely exist in the amide form. The enol-type tautomeric representation is reproduced the referenced patents and patent applications simply to allow direct comparison the compounds of the invention with those in the references.

In one embodiment, as described in part in U.S. Pat. No. 5,985,848 and in PCT International Patent Application Publication No. WO 99/19338, the contents of which are herein incorporated by reference, the MTIP inhibitor comprises a compound having formula (I):

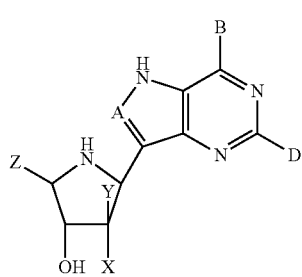

(I)

wherein A is CH or N; B is OH; D is chosen from H, OH, $NH_2$, or $SCH_3$; and X and Y are independently selected from H, OH or halogen, except that when one of X and Y is hydroxy or halogen, the other is hydrogen; Z is selected from $CH_2SQ$, $CH_2OQ$ or Q, where Q is an optionally substituted alkyl, alkenyl, aralkyl, aralkenyl or aryl group, each of which is optionally substituted with one or more substituents selected from hydroxy, halogen, methoxy, amino, carboxy, or straight- or branched-chain $C_1$-$C_6$ alkyl; provided that Q is not $CH_2OH$; or a tautomer thereof; or a pharmaceutically acceptable salt thereof; or an ester thereof.

Preferably A is CH. Preferably D is H. Preferably X is OH and Y is H. Preferably Z is $CH_2SQ$. Preferably, when Z is $CH_2SQ$, Q is alkyl, preferably an optionally substituted $C_1$-$C_6$ alkyl group such as methyl, ethyl, propyl or butyl, or Q is an aryl group such as a phenyl group or an aralkyl group such as a benzyl group. It is also preferred that Q is an alkyl group substituted with one or more amino groups. Preferably Q is an alkyl group substituted with one or more amino and one or more carboxy groups.

Alternatively preferably, Z is Q. Preferably, when Z is Q, Q is an optionally substituted alkyl group, e.g. a $C_1$-$C_6$ alkyl group such as a methyl, ethyl, propyl or butyl group. It is also preferred that Q is an alkyl group substituted with one or more amino groups. Preferably Q is an alkyl group substituted with one or more amino and one or more carboxy groups.

Alternatively, preferably, Z is Q and Q is an optionally substituted aralkyl group, e.g. a phenylethyl group. In still other preferred embodiments, Q is an optionally substituted aralkenyl group, e.g. a phenylethenyl group, e.g. a cis-phenylethenyl group or a trans-phenylethenyl group.

It is preferred that Z is selected from the group consisting of: phenylthiomethyl, p-chlorophenylthiomethyl, methylthiomethyl, ethylthiomethyl, propylthiomethyl, e.g. n-propylthiomethyl or isopropylthiomethyl, butylthiomethyl, —$CH_2$, $S(CH_2)_2CH(NH_2)COOH$, methyl, ethyl, propyl, butyl, benzyl, cis-phenylethenyl, trans-phenylethenyl and —$(CH_2)_4CH_3C(NH_2)COOH$.

Preferably when one or more halogens are present they are chosen from chlorine and fluorine.

In one embodiment, A is CH or N; B is OH; D is chosen from H, OH, $NH_2$, or $SCH_3$; and X is OH; Y is H; Z is Q, where Q is a methyl group optionally substituted with a halogen, a methoxy, an amino or a carboxy group, or Q is an optionally substituted aralkyl, aryl or $C_2$-$C_{10}$ alkyl group, each of which is optionally substituted with one or more substituents selected from hydroxy, halogen, methoxy, amino, carboxy, or straight- or branched-chain $C_1$-$C_6$ alkyl; or a tautomer thereof; or a pharmaceutically acceptable salt thereof; or an ester thereof.

Preferred compounds include those having the formula (II):

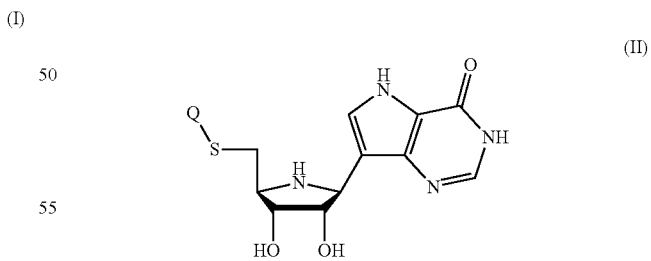

(II)

where Q is aryl, aralkyl or alkyl, each of which is optionally substituted with one or more substituents selected from hydroxy, halogen, methoxy, amino, carboxy, or straight- or branched-chain $C_1$-$C_6$ alkyl; or a tautomer thereof; or a pharmaceutically acceptable salt thereof, or an ester thereof. Preferably, Q is alkyl, preferably a $C_1$-$C_6$ alkyl group such as methyl, ethyl, propyl or butyl, or Q is an aryl group such as a phenyl group or an aralkyl group such as a benzyl group. Preferably Q is an alkyl group substituted with one or more amino and one or more carboxy groups. Preferred compounds include those where Q is methyl or optionally substituted phenyl.

Additional preferred compounds include those having the formula (IIa):

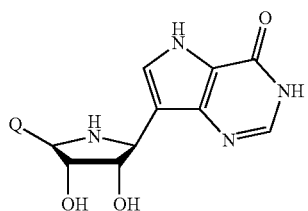

(IIa)

where Q is a methyl group optionally substituted with a halogen, a methoxy, an amino or a carboxy group, or Q is an optionally substituted aralkyl, aryl or $C_2$-$C_{10}$ alkyl group, each of which is optionally substituted with one or more substituents selected from hydroxy, halogen, methoxy, amino, carboxy, or straight- or branched-chain $C_1$-$C_6$ alkyl; or a tautomer thereof; or a pharmaceutically acceptable salt thereof, or an ester thereof. Preferably, Q is alkyl, preferably a $C_1$-$C_6$ alkyl group such as methyl, ethyl, propyl or butyl, or Q is an aryl group such as a phenyl group or an aralkyl group such as a benzyl group or an aralkenyl group such as a phenylethenyl group e.g. a cis-phenylethenyl group or a trans-phenylethenyl group. Preferably Q is an alkyl group substituted with one or more amino and one or more carboxy groups.

Examples of compounds of formula (I) include:

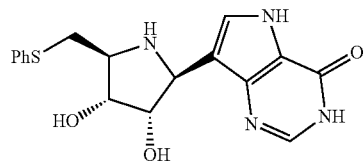

7-((2S,3S,4R,5S)-3,4-dihydroxy-5-(phenylthiomethyl)pyrrolidin-2-yl)-3H-pyrrolo[3,2-d]pyrimidin-4(5H)-one

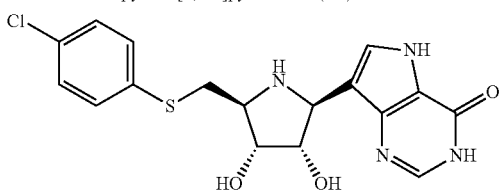

7-((2S,3S,4R,5S)-5-((4-chlorophenylthio)methyl)-3,4-dihydroxypyrrolidin-2-yl)-3H-pyrrolo[3,2-d]pyrimidin-4(5H)-one

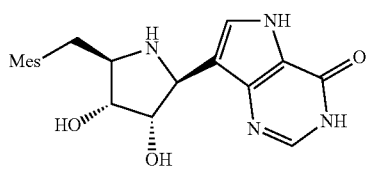

7-((2S,3S,4R,5S)-3,4-dihydroxy-5-(methylthiomethyl)pyrrolidin-2-yl)-3H-pyrrolo[3,2-d]pyrimidin-4(5H)-one -continued

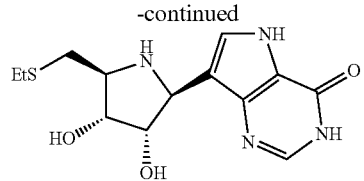

7-((2S,3S,4R,5S)-5-(ethylthiomethyl)-3,4-dihydroxypyrrolidin-2-yl)-3H-pyrrolo[3,2-d]pyrimidin-4(5H)-one

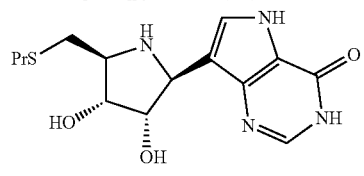

7-((2S,3S,4R,5S)-3,4-dihydroxy-5-(propylthiomethyl)pyrrolidin-2-yl)-3H-pyrrolo[3,2-d]pyrimidin-4(5H)-one

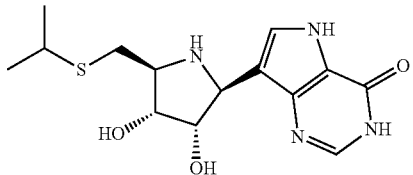

7-((2S,3S,4R,5S)-3,4-dihydroxy-5-(isopropylthiomethyl)pyrrolidin-2-yl)-3H-pyrrolo[3,2-d]pyrimidin-4(5H)-one

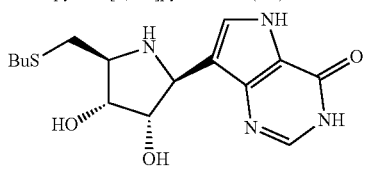

7-((2S,3S,4R,5S)-5-(butylthiomethyl)-3,4-dihydroxypyrrolidin-2-yl)-3H-pyrrolo[3,2-d]pyrimidin-4(5H)-one

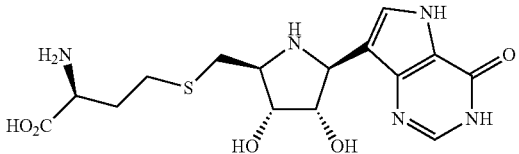

(S)-2-amino-4-(((2S,3R,4S,5S)-3,4-dihydroxy-5-(4-oxo-4,5-dihydro-3H-pyrrolo[3,2-d]pyrimidin-7-yl)pyrrolidin-2-yl)methylthio)butanoic acid

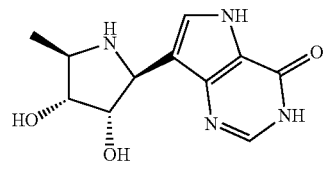

7-((2S,3S,4R,5R)-3,4-dihydroxy-5-methylpyrrolidin-2-yl)-3H-pyrrolo[3,2-d]pyrimidin-4(5H)-one

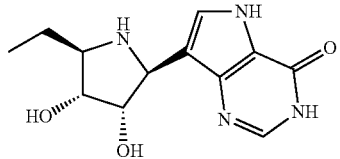

7-((2S,3S,4R,5R)-5-ethyl-3,4-dihydroxypyrrolidin-2-yl)-3H-pyrrolo[3,2-d]pyrimidin-4(5H)-one -continued

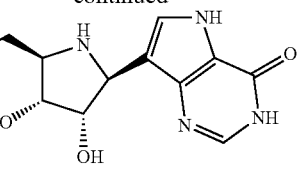

7-((2S,3S,4R,5R)-3,4-dihydroxy-5-propylpyrrolidin-2-yl)-3H-pyrrolo[3,2-d]pyrimidin-4(5H)-one

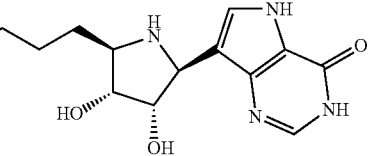

7-((2S,3S,4R,5R)-5-butyl-3,4-dihydroxypyrrolidin-2-yl)-3H-pyrrolo[3,2-d]pyrimidin-4(5H)-one

7-((2S,3S,4R,5R)-3,4-dihydroxy-5-phenethylpyrrolidin-2-yl)-3H-pyrrolo[3,2-d]pyrimidin-4(5H)-one

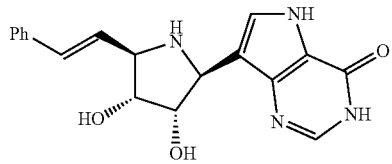

7-((2S,3S,4R,5R)-cis-3,4-dihydroxy-5-styrylpyrrolidin-2-yl)-3H-pyrrolo[3,2-d]pyrimidin-4(5H)-one

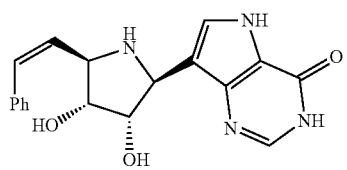

7-((2S,3S,4R,5R)-trans-3,4-dihydroxy-5-styrylpyrrolidin-2-yl)-3H-pyrrolo[3,2-d]pyrimidin-4(5H)-one

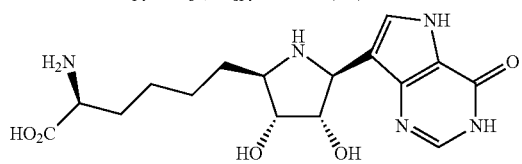

(S)-2-amino-6-((2R,3R,4S,5S)-3,4-dihydroxy-5-(4-oxo-4,5-dihydro-3H-pyrrolo[3,2,d]pyrimidin-7-yl)pyrrolidin-2-yl)hexanoic acid

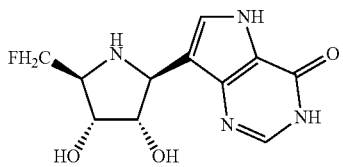

7-((2S,3S,4R,5S)-5-(fluoromethyl)-3,4-dihydroxypyrrolidin-2-yl)-3H-pyrrolo[3,2-d]pyrimidin-4(5H)-one and

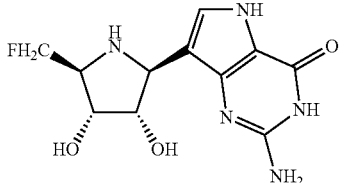

2-amino-7-((2S,3S,4R,5S)-5-(fluoromethyl)-3,4-dihydroxypyrrolidin-2-yl)-3H-pyrrolo[3,2-d]pyrimidin-4(5H)-one or a tautomer thereof; or a pharmaceutically acceptable salt thereof; or an ester thereof.

Preferred compounds include those having the structure:

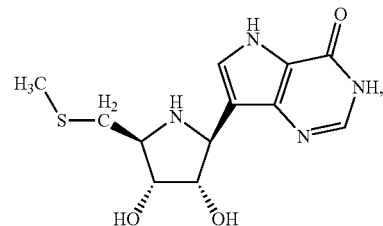

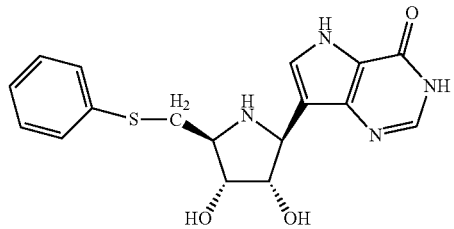
or

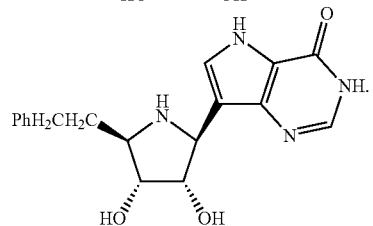

In another embodiment, as described in U.S. Pat. No. 7,553,839 and in PCT International Patent Application Publication No. WO 04/018496, and in WO 2007/069924, the contents of which are herein incorporated by reference, the MTIP inhibitor comprises a compound having formula (III) or (IIIa):

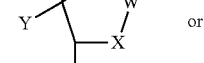  (III)

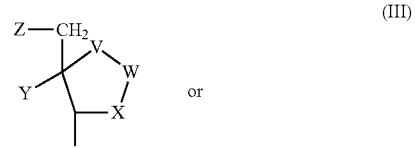

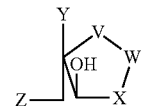  (IIIa)

wherein V is $CH_2$ and W is $NR^1$; X is $CH_2$; Y is selected from hydrogen, halogen and hydroxyl; Z is selected from hydrogen, halogen, SQ, OQ and Q, where Q is an optionally substituted alkyl, aralkyl or aryl group, each of which is optionally substituted with one or more substituents selected from hydroxy, halogen, methoxy, amino, carboxy, or straight- or branched-chain $C_1$-$C_6$ alkyl; $R^1$ is a radical of the formula (IV)

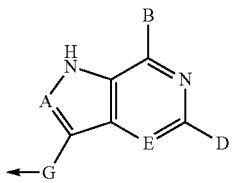
(IV)

A is selected from N, CH and CR, where R is selected from halogen or optionally substituted alkyl, aralkyl or aryl group, each of which is optionally substituted with one or more substituents selected from hydroxy, halogen, methoxy, amino, carboxy, or straight- or branched-chain $C_1$-$C_6$ alkyl; B is OH; D is selected from OH, $NH_2$, $SCH_3$ and hydrogen; E is N; G is $CH_2$; or a tautomer thereof or a pharmaceutically acceptable salt thereof; or an ester thereof.

Preferably Y is H. Preferably Z is SQ. Preferably A is CH. Preferably D is H. Preferably Q is alkyl, preferably a $C_1$-$C_6$ alkyl group such as methyl, ethyl, propyl, butyl, pentyl or cyclohexyl or Q is an aryl group such as a phenyl group or an aralkyl group such as a benzyl group. It is also preferred that Q is an alkyl group substituted with one or more amino and one or more carboxy groups.

Preferred compounds include those having the formula (V):

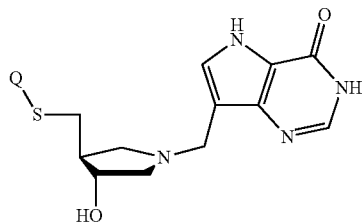
(V)

where Q is aryl, aralkyl or alkyl, each of which is optionally substituted with one or more substituents selected from hydroxy, halogen, methoxy, amino, carboxy, and straight- or branched-chain $C_1$-$C_6$ alkyl; or a tautomer thereof; or an ester thereof; or a pharmaceutically acceptable salt thereof, or a prodrug thereof. Preferably, Q is optionally substituted alkyl, preferably a $C_1$-$C_6$ alkyl group such as methyl, ethyl, propyl or butyl, or Q is an optionally substituted aryl group such as a phenyl group or an optionally substituted aralkyl group such as a benzyl group. Preferred compounds include those where Q is methyl or phenyl. It is also preferred that Q is an alkyl group substituted with one or more amino groups. Preferably Q is an alkyl group substituted with one or more amino and one or more carboxy groups.

Other preferred compounds include those having the formula (Va):

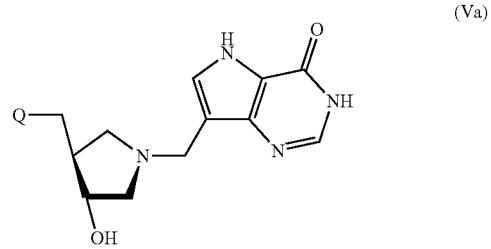
(Va)

where Q is aryl, aralkyl or alkyl, each of which is optionally substituted with one or more substituents selected from hydroxy, halogen, methoxy, amino, carboxy, and straight- or branched-chain $C_1$-$C_6$ alkyl; or a tautomer thereof; or an ester thereof; or a pharmaceutically acceptable salt thereof, or a prodrug thereof. Preferably, Q is optionally substituted alkyl, preferably a $C_1$-$C_6$ alkyl group such as methyl, ethyl, propyl or butyl, or Q is an optionally substituted aryl group such as a phenyl group or an aralkyl group such as a benzyl group. Preferred compounds include those where Q is methyl, ethyl or phenyl. It is also preferred that Q is an alkyl group substituted with one or more amino groups. Preferably Q is an alkyl group substituted with one or more amino and one or more carboxy groups.

Examples of compounds of formula (III) include:

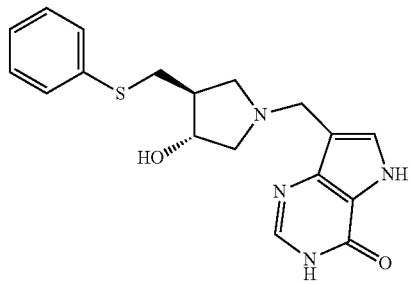

7-(((3R,4S)-3-hydroxy-4-(phenylthiomethyl)pyrrolidin-1-yl)methyl)-3H-pyrrolo[3,2-d]pyrimidin-4(5H)-one

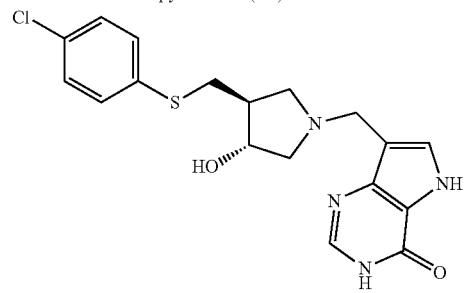

7-(((3S,4R)-3-((4-chlorophenylthio)methyl)-4-hydroxypyrrolidin-1-yl)methyl)-3H-pyrrolo[3,2-d]pyrimidin-4(5H)-one

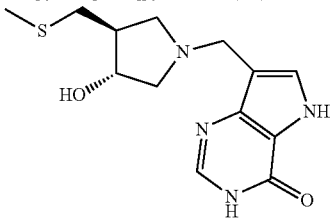

7-(((3R,4S)-3-hydroxy-4-(methylthiomethyl)pyrrolidin-1-yl)methyl)-3H-pyrrolo[3,2-d]pyrimidin-4(5H)-one

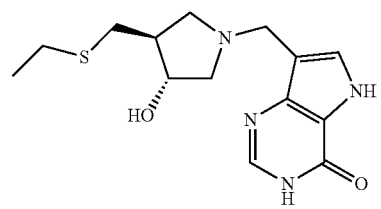

7-(((3S,4R)-3-(ethylthiomethyl)-4-
hydroxypyrrolidin-1-yl)methyl)-3H-
pyrrolo[3,2-d]pyrimidin-4(5H)-one

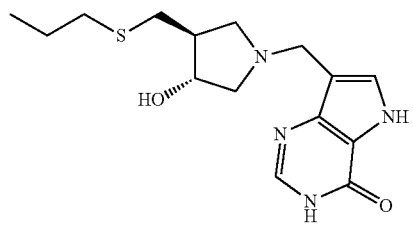

Compound 24 in Example 1.20, WO 04 069856
7-(((3R,4S)-3-hydroxy-4-(propylthiomethyl)
pyrrolidin-1-yl)methyl)-3H-pyrrolo[3,2-d]
pyrimidin-4(5H)-one

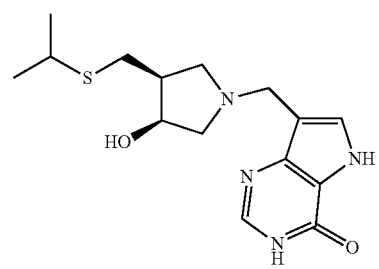

7-(((3R,4S)-3-hydroxy-4-(isopropylthiomethyl)pyrrolidin-1-
yl)methyl)-3H-pyrrolo[3,2-d]pyrimidin-4(5H)-one

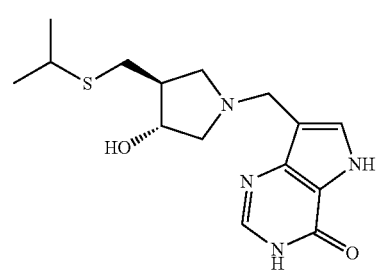

7-(((3R,4S)-3-hydroxy-4-
(isopropylthiomethyl)pyrrolidin-1-yl)methyl)-
3H-pyrrolo[3,2-d]pyrimidin-4(5H)-one

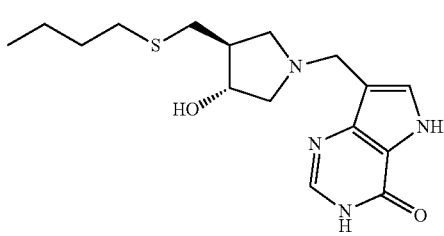

Compound 25 in Example 1.20, WO 04 069856
7-(((3S,4R)-3-(butylthiomethyl)-4-hydroxypyrrolidin-
1-yl)methyl)-3H-pyrrolo[3,2-d]pyrimidin-4(5H)-one

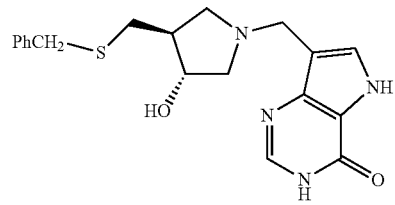

7-(((3R,4S)-3-(benzythiomethyl)-4-
hydroxypyrrolidin-1-yl)methyl)-
3H-pyrrolo[3,2-d]pyrimidin-4(5H)-one

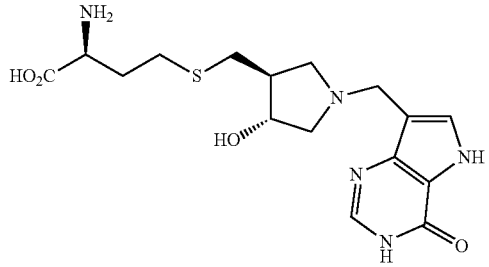

(S)-2-amino-4-(((3S,4R)-4-hydroxy-1-((4-oxo-4,5-
dihydro-3H-pyrrolo[3,2-d]pyrimidin-7-yl)methyl)
pyrrolidin-3-yl)methylthio)butanoic acid

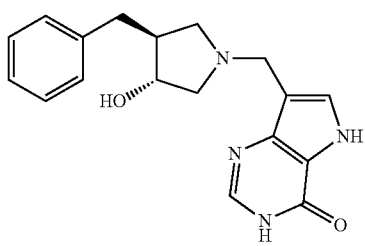

7-(((3S,4R)-3-benzyl-4-
hydroxypyrrolidin-1-yl)methyl)-
3H-pyrrolo[3,2-d]pyrimidin-4(5H)-one

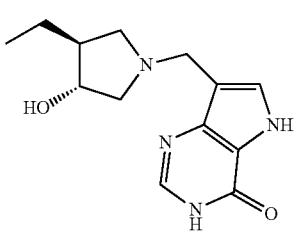

7-(((3S,4R)-3-ethyl-4-
hydroxypyrrolidin-1-yl)methyl)-3H-
pyrrolo[3,2-d]pyrimidin-4(5H)-one

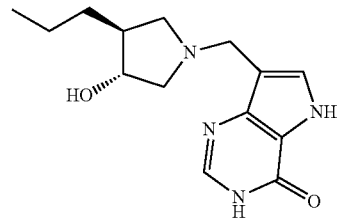

Compound 28 in Example 1.24,
WO 04 069856
7-(((3R,4S)-3-hydroxy-4-
propylpyrrolidin-1-yl)methyl)-3H-
pyrrolo[3,2-d]pyrimidin-4(5H)-one

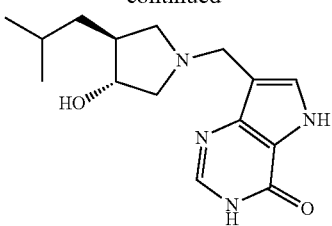

7-(((3R,4S)-3-hydroxy-4-isobutylpyrrolidin-1-yl)methyl)-3H-pyrrolo[3,2-d]pyrimidin-4(5H)-one

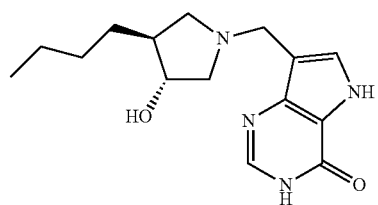

7-(((3S,4R)-3-butyl-4-hydroxypyrrolidin-1-yl)methyl)-3H-pyrrolo[3,2-d]pyrimidin-4(5H)-one

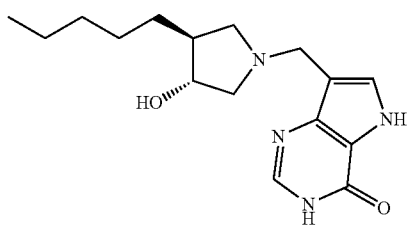

7-(((3R,4S)-3-hydroxy-4-pentylpyrrolidin-1-yl)methyl)-3H-pyrrolo[3,2-d]pyrimidin-4(5H)-one

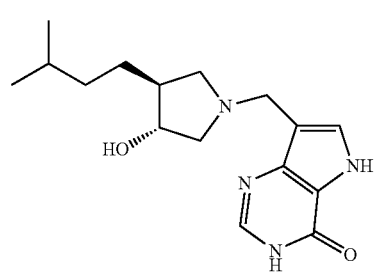

7-(((3R,4S)-3-hydroxy-4-isopentylpyrrolidin-1-yl)methyl)-3H-pyrrolo[3,2-d]pyrimidin-4(5H)-one

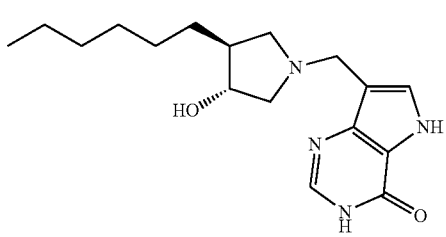

7-(((3R,4S)-3-hydroxy-4-phenethylpyrrolidin-1-yl)methyl)-3H-pyrrolo[3,2-d]pyrimidin-4(5H)-one

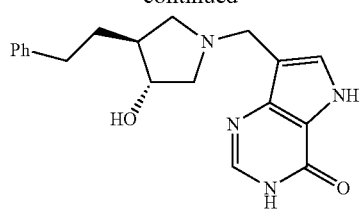

7-(((3S,4R)-3-hexyl-4-hydroxypyrrolidin-1-yl)methyl)-3H-pyrrolo[3,2-d]pyrimidin-4(5H)-one

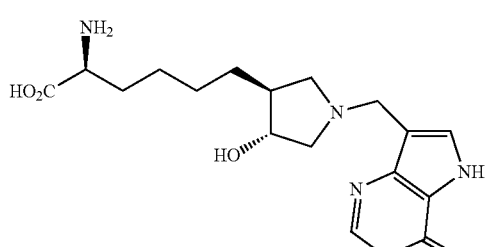

(S)-2-amino-6-((3S,4R)-4-hydroxy-1-((4-oxo-4,5-dihydro-3H-pyrrolo[3,2-d]pyrimidin-7-yl)methyl)pyrrolidin-3-yl)hexanoic acid

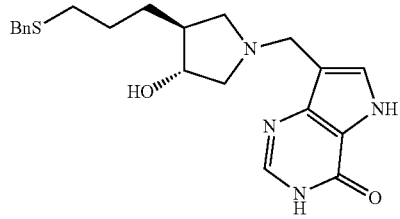

7-(((3S,4R)-3-(3-(benzylthio)propyl)-4-hydroxypyrrolidin-1-yl)methyl)-3H-pyrrolo[3,2-d]pyrimidin-4(5H)-one

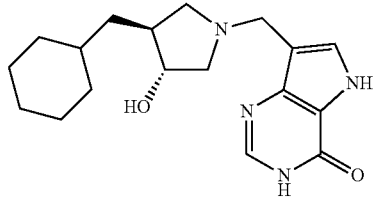

7-(((3S,4R)-3-(cyclohexylmethyl)-4-hydroxypyrrolidin-1-yl)methyl)-3H-pyrrolo[3,2-d]pyrimidin-4(5H)-one

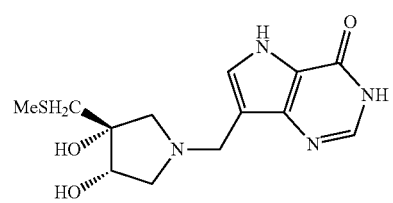

7-(((3R,4S)-3,4-dihydroxy-3-(methylthiomethyl)pyrrolidin-1-yl)methyl)-3H-pyrrolo[3,2-d]pyrimidin-4(5H)-one and

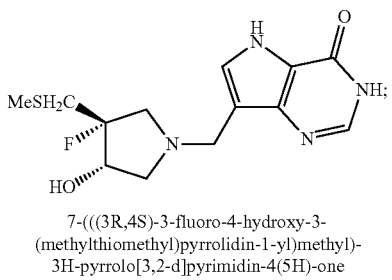

7-(((3R,4S)-3-fluoro-4-hydroxy-3-(methylthiomethyl)pyrrolidin-1-yl)methyl)-3H-pyrrolo[3,2-d]pyrimidin-4(5H)-one or a tautomer thereof; or a pharmaceutically acceptable salt thereof; or an ester thereof.

Preferred compounds include those having the structure:

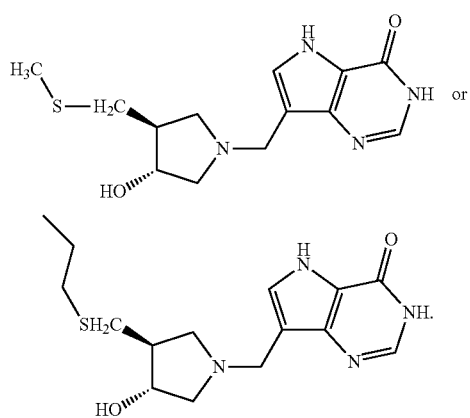

Examples of compounds of formula (IIIa) include:

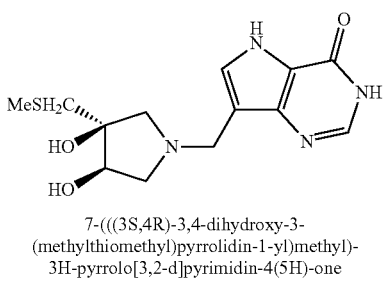

7-(((3S,4R)-3,4-dihydroxy-3-(methylthiomethyl)pyrrolidin-1-yl)methyl)-3H-pyrrolo[3,2-d]pyrimidin-4(5H)-one

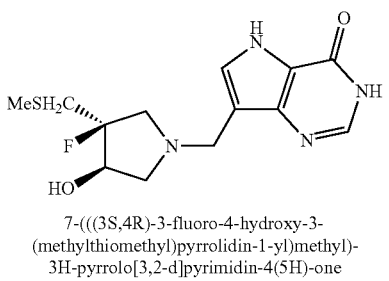

7-(((3S,4R)-3-fluoro-4-hydroxy-3-(methylthiomethyl)pyrrolidin-1-yl)methyl)-3H-pyrrolo[3,2-d]pyrimidin-4(5H)-one

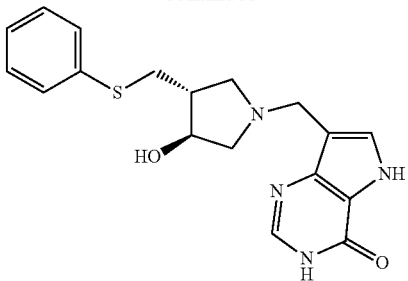

7-(((3S,4R)-3-hydroxy-4-(phenylthiomethyl)pyrrolidin-1-yl)methyl)-3H-pyrrolo[3,2-d]pyrimidin-4(5H)-one

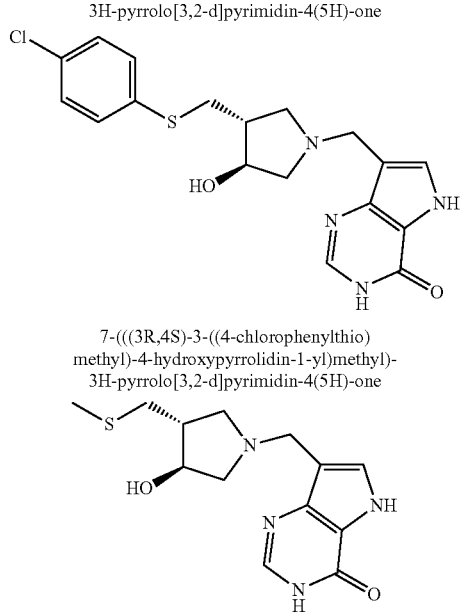

7-(((3R,4S)-3-((4-chlorophenylthio)methyl)-4-hydroxypyrrolidin-1-yl)methyl)-3H-pyrrolo[3,2-d]pyrimidin-4(5H)-one 7-(((3S,4R)-3-hydroxy-4-(methylthiomethyl)pyrrolidin-1-yl)methyl)-3H-pyrrolo[3,2-d]pyrimidin-4(5H)-one

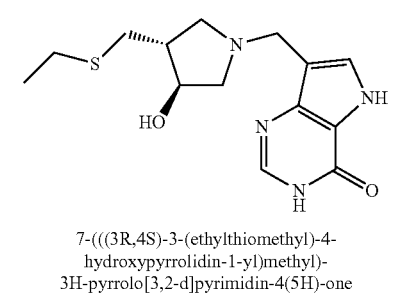

7-(((3R,4S)-3-(ethylthiomethyl)-4-hydroxypyrrolidin-1-yl)methyl)-3H-pyrrolo[3,2-d]pyrimidin-4(5H)-one

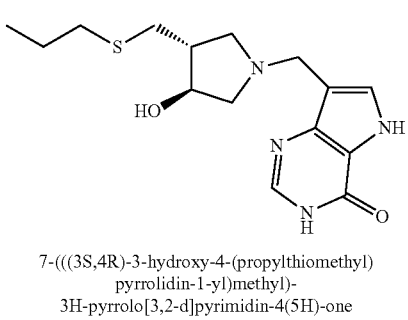

7-(((3S,4R)-3-hydroxy-4-(propylthiomethyl)pyrrolidin-1-yl)methyl)-3H-pyrrolo[3,2-d]pyrimidin-4(5H)-one

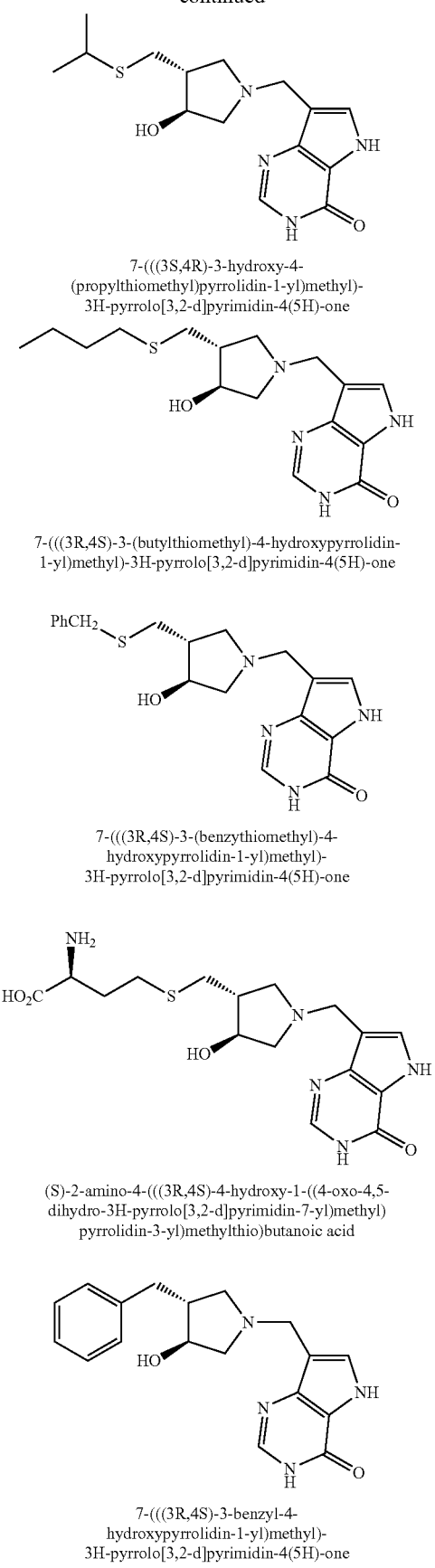

7-(((3S,4R)-3-hydroxy-4-(propylthiomethyl)pyrrolidin-1-yl)methyl)-3H-pyrrolo[3,2-d]pyrimidin-4(5H)-one 7-(((3R,4S)-3-(butylthiomethyl)-4-hydroxypyrrolidin-1-yl)methyl)-3H-pyrrolo[3,2-d]pyrimidin-4(5H)-one 7-(((3R,4S)-3-(benzythiomethyl)-4-hydroxypyrrolidin-1-yl)methyl)-3H-pyrrolo[3,2-d]pyrimidin-4(5H)-one (S)-2-amino-4-(((3R,4S)-4-hydroxy-1-((4-oxo-4,5-dihydro-3H-pyrrolo[3,2-d]pyrimidin-7-yl)methyl)pyrrolidin-3-yl)methylthio)butanoic acid 7-(((3R,4S)-3-benzyl-4-hydroxypyrrolidin-1-yl)methyl)-3H-pyrrolo[3,2-d]pyrimidin-4(5H)-one

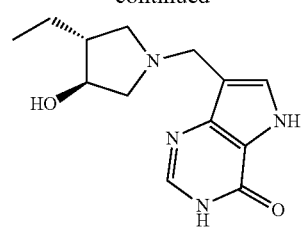

7-(((3S,4R)-3-hydroxy-4-propylpyrrolidin-1-yl)methyl)-3H-pyrrolo[3,2-d]pyrimidin-4(5H)-one

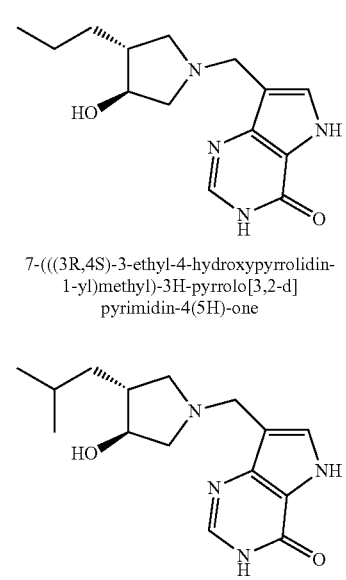

7-(((3R,4S)-3-ethyl-4-hydroxypyrrolidin-1-yl)methyl)-3H-pyrrolo[3,2-d]pyrimidin-4(5H)-one 7-(((3S,4R)-3-hydroxy-4-isobutylpyrrolidin-1-yl)methyl)-3H-pyrrolo[3,2-d]pyrimidin-4(5H)-one

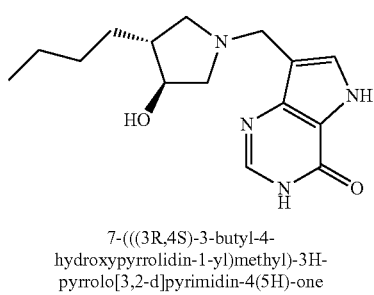

7-(((3R,4S)-3-butyl-4-hydroxypyrrolidin-1-yl)methyl)-3H-pyrrolo[3,2-d]pyrimidin-4(5H)-one

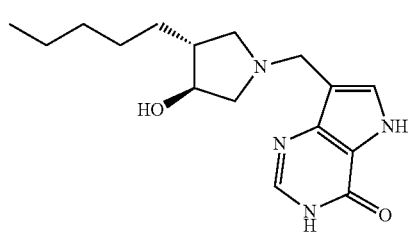

7-(((3S,4R)-3-hydroxy-4-pentylpyrrolidin-1-yl)methyl)-3H-pyrrolo[3,2-d]pyrimidin-4(5H)-one

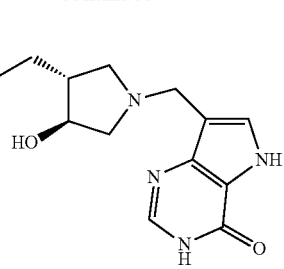

7-(((3R,4R)-3-hydroxy-4-isopentylpyrrolidin-1-yl)methyl)-3H-pyrrolo[3,2-d]pyrimidin-4(5H)-one

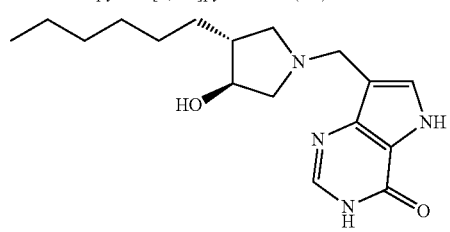

7-(((3R,4S)-3-hexyl-4-hydroxylpyrrolidin-1-yl)methyl)-3H-pyrrolo[3,2-d]pyrimidin-4(5H)-one

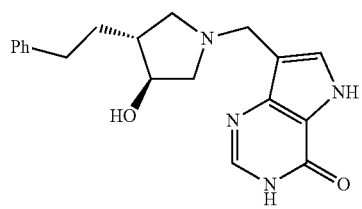

7-(((3S,4R)-3-hydroxy-4-phenethylpyrrolidin-1-yl)methyl)-3H-pyrrolo[3,2-d]pyrimidin-4(5H)-one

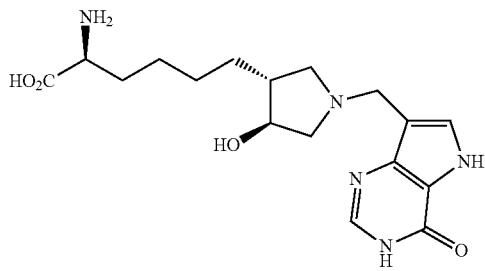

(S)-2-amino-6-((3R,4S)-4-hydroxy-1-((4-oxo-4,5-dihydro-3H-pyrrolo[3,2-d]pyrimidin-7-yl)methyl)pyrrolidin-3-yl)hexanoic acid

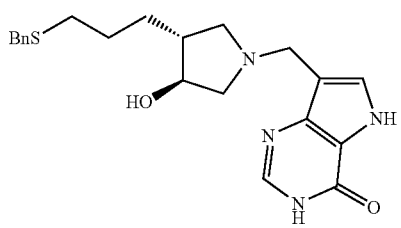

7-(((3R,4S)-3-(3-(benzylthio)propyl)-4-hydroxypyrrolidin-1-yl)methyl)-3H-pyrrolo[3,2-d]pyrimidin-4(5H)-one

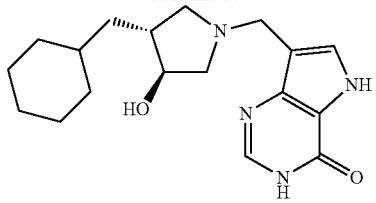

7-(((3R,4S)-3-(cyclohexylmethyl)-4-hydroxypyrrolidin-1-yl)methyl)-3H-pyrrolo[3,2-d]pyrimidin-4(5H)-one or a tautomer thereof; or a pharmaceutically acceptable salt thereof; or an ester thereof.

In another embodiment, as described in PCT International Patent Application Publication No. WO 2008/030119, the contents of which are herein incorporated by reference, the MTP inhibitor comprises a compound having formula (VI):

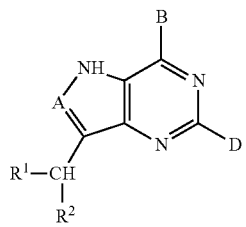

(VI)

wherein $R^1$ is H or $NR^3R^4$; $R^2$ is H or an alkyl, alkenyl, alkynyl, aralkyl, aralkenyl, aralkynyl, or aryl group, each of which is optionally substituted with one or more hydroxy, alkoxy, thiol, alkylthio, arylthio, aralkylthio, halogen, carboxylic acid, carboxylate alkyl ester, nitro, or $NR^3R^4$ groups, where each alkylthio, arylthio and aralkylthio group is optionally substituted with one or more alkyl, halogen, amino, hydroxy, or alkoxy groups; provided that when $R^1$ is H, $R^2$ is an alkyl, alkenyl, alkynyl, aralkyl, aralkenyl, aralkynyl, or aryl group which is substituted with at least one $NR^3R^4$ group, and optionally substituted with one or more hydroxy, alkoxy, thiol, alkylthio, arylthio, aralkylthio, halogen, carboxylic acid, carboxylate alkyl ester or nitro group; $R^3$ and $R^4$, independently of each other, are H or an alkyl, alkenyl, alkynyl, aralkyl, aralkenyl, aralkynyl, or aryl group, each of which is optionally substituted with one or more hydroxy, alkoxy, thiol, alkylthio, arylthio, aralkylthio, halogen, carboxylic acid, carboxylate alkyl ester, nitro, or $NR^3R^4$ groups, where each alkylthio, arylthio and aralkylthio group is optionally substituted with one or more alkyl, halogen, amino, hydroxy, or alkoxy groups; A is N or CH; B is OH; and D is H, OH, $NH_2$, or $SCH_3$; or a tautomer thereof, or a pharmaceutically acceptable salt thereof, or an ester prodrug form thereof.

Preferably, $R^1$ is $NR^3R^4$ and $R^2$ is H. It is further preferred that $R^1$ is $NR^3R^4$ and one of $R^3$ and $R^4$ is H, a lower alkyl group, e.g. a methyl group, or an aralkyl group, e.g. a benzyl group. Preferably $R^1$ is $NR^3R^4$ and one of $R^3$ and $R^4$ is H.

Preferably $R^3$ or $R^4$ is alkyl substituted by one or more hydroxy groups and/or one or more optionally substituted thiol, alkylthio, arylthio, or aralkylthio groups. For example, $R^3$ or $R^4$ may be, methylthioethyl, methylthiopropyl, methylthiohydroxypropyl, methylthiobutyl, methylthiohydroxybutyl, methylthiodihydroxybutyl, methylthiopentyl, methylthiohydroxypentyl, methylthiodihydroxypentyl, or methylthiotrihydroxypentyl.

Preferably $R^1$ is $NR^3R^4$ and one of $R^3$ and $R^4$ is H and the other is selected from the group consisting of methylthioethyl, methylthiopropyl, methylthiohydroxypropyl, methylthiobutyl, methylthiohydroxybutyl, methylthiodihydroxybutyl, methylthiopentyl, methylthiohydroxypentyl, methylthiodihydroxypentyl, and methylthiotrihydroxypentyl.

In addition, preferably $R^2$ is an optionally substituted alkyl group, more preferably an optionally substituted $C_1$-$C_5$ alkyl group, for example, hydroxymethyl, hydroxyethyl, hydroxypropyl, dihydroxypropyl, hydroxybutyl, dihydroxybutyl, trihyroxybutyl, hydroxypentyl, dihydroxypentyl, trihydroxypentyl, methylthiomethyl, methylthioethyl, methylthiopropyl, methylthiohydroxypropyl, methylthiobutyl, methylthiohydroxybutyl, methylthiodihydroxybutyl, methylthiopentyl, methylthiohydroxypentyl, methylthiodihydroxypentyl, or methylthiotrihydroxypentyl.

Preferably A is CH. It is further preferred that D is H.

Preferred compounds include those having the formula (VIa):

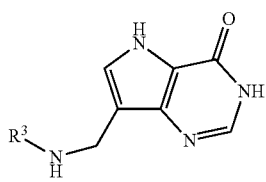

(VIa)

wherein $R^3$ is an alkyl, alkenyl, alkynyl, aralkyl, aralkenyl, aralkynyl, or aryl group, each of which is optionally substituted with one or more hydroxy, alkoxy, thiol, alkylthio, arylthio, aralkylthio, halogen, carboxylic acid, carboxylate alkyl ester, or nitro group, where each alkylthio, arylthio and aralkylthio group is optionally substituted with one or more alkyl, halogen, amino, hydroxy, or alkoxy groups; or a tautomer thereof, or a pharmaceutically acceptable salt thereof, or an ester prodrug form thereof.

Other preferred compounds include those having the formula (VIb):

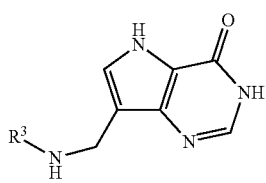

(VIb)

wherein $R^3$ is an alkyl, alkenyl, alkynyl, aralkyl, aralkenyl, aralkynyl, or aryl group, each of which is substituted with at least one alkoxy, thiol, alkylthio, arylthio, or aralkylthio group and optionally substituted with one or more hydroxy, halogen, carboxylic acid, carboxylate alkyl ester, or nitro group, where each alkylthio, arylthio and aralkylthio group is optionally substituted with one or more alkyl, halogen, amino, hydroxy, or alkoxy groups; or a tautomer thereof, or a pharmaceutically acceptable salt thereof, or an ester prodrug form thereof.

Preferably $R^3$ in the above formulae (VIa) and (VIb) is selected from the group consisting of, methylthioethyl, methylthiopropyl, methylthiohydroxypropyl, methylthiobutyl, methylthiohydroxybutyl, methylthiodihydroxybutyl, methylthiopentyl, methylthiohydroxypentyl, methylthiodihydroxypentyl, or methylthiotrihydroxypentyl.

Examples of compounds of formula (VI), as described in WO 2008/030119, include:

2-amino-7-(2,3-dihydroxy-1-(2-(methylthio)ethylamino)propyl)-3H-pyrrolo[3,2-d]pyrimidin-4(5H)-one;

7-(2,3-dihydroxy-1-(2-(methylthio)ethylamino)propyl)-3H-pyrrolo[3,2-d]pyrimidin-4(5H)-one;

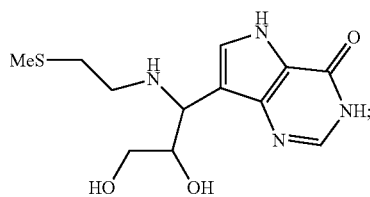 [SMILES: CSCCNC(c1c[nH]c2c(=O)[nH]cnc12)C(O)CO]

2-amino-7-(1-amino-2,3-dihydroxy-5-(methylthio)pentyl)-3H-pyrrolo[3,2-d]pyrimidin-4(5H)-one;

7-(1-amino-2,3-dihydroxy-5-(methylthio)pentyl)-3H-pyrrolo[3,2-d]pyrimidin-4(5H)-one;

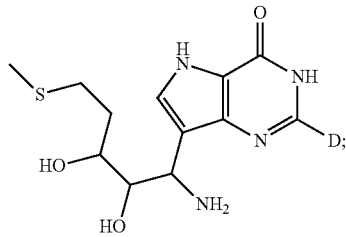

2-amino-7-(2-hydroxy-1-(1-hydroxy-3-(methylthio)propan-2-ylamino)ethyl)-3H-pyrrolo[3,2-d]pyrimidin-4(5H)-one;

7-(2-hydroxy-1-(1-hydroxy-3-(methylthio)propan-2-ylamino)ethyl)-3H-pyrrolo[3,2-d]pyrimidin-4(5H)-one;

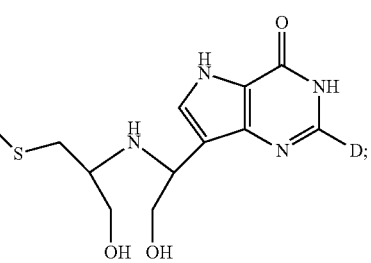

2-amino-7-((3,4-dihydroxy-1-(methylthio)butan-2-ylamino)methyl)-3H-pyrrolo[3,2-d]pyrimidin-4(5H)-one;

7-((3,4-dihydroxy-1-(methylthio)butan-2-ylamino)methyl)-3H-pyrrolo[3,2-d]pyrimidin-4(5H)-one (each enantiomer);

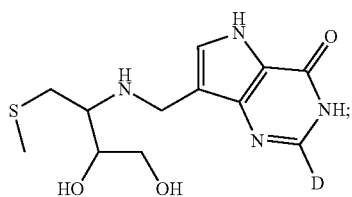 [SMILES: [2H]c1nc2c(CNC(CSC)C(O)CO)c[nH]c2c(=O)[nH]1]

2-amino-7-(((2-hydroxy-4-(methylthio)butyl)(methyl)amino)methyl)-3H-pyrrolo[3,2-d]pyrimidin-4(5H)-one;

7-(((2-hydroxy-4-(methylthio)butyl)(methyl)amino)methyl)-3H-pyrrolo[3,2-d]pyrimidin-4(5H)-one;

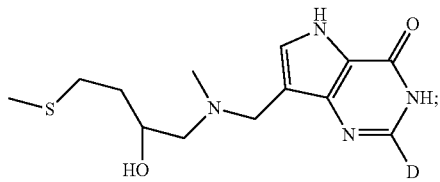 [SMILES: [2H]c1nc2c(CN(C)CC(O)CCSC)c[nH]c2c(=O)[nH]1]

2-amino-7-((2-hydroxy-4-(methylthio)butylamino)methyl)-3H-pyrrolo[3,2-d]pyrimidin-4(5H)-one;

7-((2-hydroxy-4-(methylthio)butylamino)methyl)-3H-pyrrolo[3,2-d]pyrimidin-4(5H)-one;

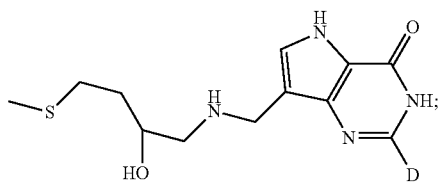 [SMILES: [2H]c1nc2c(CNCC(O)CCSC)c[nH]c2c(=O)[nH]1]

2-amino-7-((3,4-dihydroxy-2-(methylthiomethyl)butylamino)methyl)-3H-pyrrolo[3,2-d]pyrimidin-4(5H)-one;

7-((3,4-dihydroxy-2-(methylthiomethyl)butylamino)methyl)-3H-pyrrolo[3,2-d]pyrimidin-4(5H)-one (DL-erythro, DL-threo);

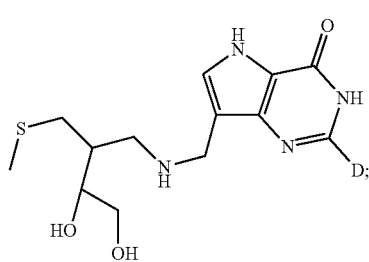

2-amino-7-((3-hydroxy-2-(methylthiomethyl)propylamino)methyl)-3H-pyrrolo[3,2-d]pyrimidin-4(5H)-one;

7-((3-hydroxy-2-(methylthiomethyl)propylamino)methyl)-3H-pyrrolo[3,2-d]pyrimidin-4(5H)-one;

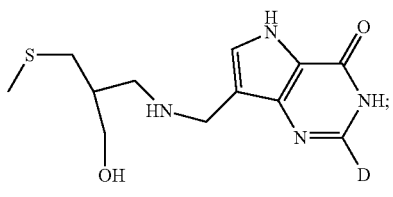 [SMILES: [2H]c1nc2c(CNCC(CO)CSC)c[nH]c2c(=O)[nH]1]

7-(((3-hydroxy-2-(methylthiomethyl)propyl)(methyl)amino)methyl)-3H-pyrrolo[3,2-d]pyrimidin-4(5H)-one;

2-amino-7-(((3-hydroxy-2-(methylthiomethyl)propyl)(methyl)amino)methyl)-3H-pyrrolo[3,2-d]pyrimidin-4(5H)-one;

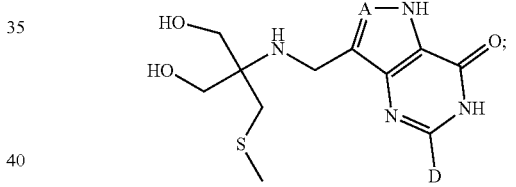

7-((1,3-dihydroxy-2-(methylthiomethyl)propan-2-ylamino)methyl)-3H-pyrrolo[3,2-d]pyrimidin-4(5H)-one;

2-amino-7-((1,3-dihydroxy-2-(methylthiomethyl)propan-2-ylamino)methyl)-3H-pyrrolo[3,2-d]pyrimidin-4(5H)-one;

5-amino-3-((1,3-dihydroxy-2-(methylthiomethyl)propan-2-ylamino)methyl)-1H-pyrazolo[4,3-d]pyrimidin-7(6H)-one;

7-((benzyl((2R,3R)-3,4-dihydroxy-2-(methylthiomethyl)butyl)amino)methyl)-3H-pyrrolo[3,2-d]pyrimidin-4(5H)-one;

7-((benzyl((2S,3S)-3,4-dihydroxy-2-(methylthiomethyl)butyl)amino)methyl)-3H-pyrrolo[3,2-d]pyrimidin-4(5H)-one;

7-((benzyl((2R,3S)-3,4-dihydroxy-2-(methylthiomethyl)butyl)amino)methyl)-3H-pyrrolo[3,2-d]pyrimidin-4(5H)-one;

7-((benzyl((2S,3R)-3,4-dihydroxy-2-(methylthiomethyl)butyl)amino)methyl)-3H-pyrrolo[3,2-d]pyrimidin-4(5H)-one;

(Racemic mixture of above two as DL-erythro);

2-amino-7-((benzyl((2R,3R)-3,4-dihydroxy-2-(methylthiomethyl)butyl)amino)methyl)-3H-pyrrolo[3,2-d]pyrimidin-4(5H)-one;

2-amino-7-((benzyl((2S,3S)-3,4-dihydroxy-2-(methylthiomethyl)butyl)amino)methyl)-3H-pyrrolo[3,2-d]pyrimidin-4(5H)-one;

2-amino-7-((benzyl((2R,3S)-3,4-dihydroxy-2-(methylthiomethyl)butyl)amino)methyl)-3H-pyrrolo[3,2-d]pyrimidin-4(5H)-one;

2-amino-7-((benzyl((2S,3R)-3,4-dihydroxy-2-(methylthiomethyl)butyl)amino)methyl)-3H-pyrrolo[3,2-d]pyrimidin-4(5H)-one;

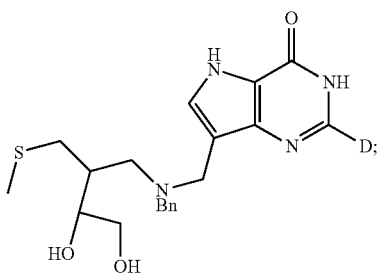

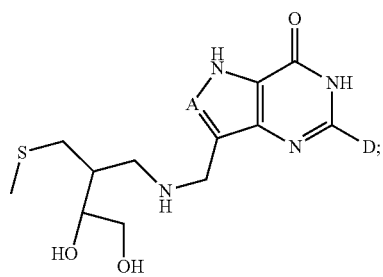

7-(((2R,3R)-2,3-dihydroxy-4-(methylthio)butylamino)methyl)-3H-pyrrolo[3,2-d]pyrimidin-4(5H)-one;

7-(((2S,3S)-2,3-dihydroxy-4-(methylthio)butylamino)methyl)-3H-pyrrolo[3,2-d]pyrimidin-4(5H)-one;

7-(((2R,3S)-2,3-dihydroxy-4-(methylthio)butylamino)methyl)-3H-pyrrolo[3,2-d]pyrimidin-4(5H)-one;

7-(((2S,3R)-2,3-dihydroxy-4-(methylthio)butylamino)methyl)-3H-pyrrolo[3,2-d]pyrimidin-4(5H)-one;

(Racemic mixture of above two as DL-threo);

2-amino-7-(((2R,3R)-2,3-dihydroxy-4-(methylthio)butylamino)methyl)-3H-pyrrolo[3,2-d]pyrimidin-4(5H)-one;

2-amino-7-(((2S,3S)-2,3-dihydroxy-4-(methylthio)butylamino)methyl)-3H-pyrrolo[3,2-d]pyrimidin-4(5H)-one;

2-amino-7-(((2R,3S)-2,3-dihydroxy-4-(methylthio)butylamino)methyl)-3H-pyrrolo[3,2-d]pyrimidin-4(5H)-one;

2-amino-7-(((2S,3R)-2,3-dihydroxy-4-(methylthio)butylamino)methyl)-3H-pyrrolo[3,2-d]pyrimidin-4(5H)-one;

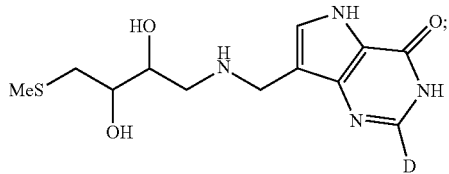 [SMILES: [2H]c1nc2c(CNCC(O)C(O)CSC)c[nH]c2c(=O)[nH]1]

7-(((2R,3R)-3,4-dihydroxy-1-(methylthio)butan-2-ylamino)methyl)-3H-pyrrolo[3,2-d]pyrimidin-4(5H)-one;

7-(((2S,3S)-3,4-dihydroxy-1-(methylthio)butan-2-ylamino)methyl)-3H-pyrrolo[3,2-d]pyrimidin-4(5H)-one;

7-(((2R,3S)-3,4-dihydroxy-1-(methylthio)butan-2-ylamino)methyl)-3H-pyrrolo[3,2-d]pyrimidin-4(5H)-one;

7-(((2S,3R)-3,4-dihydroxy-1-(methylthio)butan-2-ylamino)methyl)-3H-pyrrolo[3,2-d]pyrimidin-4(5H)-one;

2-amino-7-(((2R,3R)-3,4-dihydroxy-1-(methylthio)butan-2-ylamino)methyl)-3H-pyrrolo[3,2-d]pyrimidin-4(5H)-one;

2-amino-7-(((2S,3S)-3,4-dihydroxy-1-(methylthio)butan-2-ylamino)methyl)-3H-pyrrolo[3,2-d]pyrimidin-4(5H)-one;

2-amino-7-(((2R,3S)-3,4-dihydroxy-1-(methylthio)butan-2-ylamino)methyl)-3H-pyrrolo[3,2-d]pyrimidin-4(5H)-one;

2-amino-7-(((2S,3R)-3,4-dihydroxy-1-(methylthio)butan-2-ylamino)methyl)-3H-pyrrolo[3,2-d]pyrimidin-4(5H)-one;

3-(((2R,3R)-3,4-dihydroxy-1-(methylthio)butan-2-ylamino)methyl)-1H-pyrazolo[4,3-d]pyrimidin-7(6H)-one;

3-(((2S,3S)-3,4-dihydroxy-1-(methylthio)butan-2-ylamino)methyl)-1H-pyrazolo[4,3-d]pyrimidin-7(6H)-one;

3-(((2R,3S)-3,4-dihydroxy-1-(methylthio)butan-2-ylamino)methyl)-1H-pyrazolo[4,3-d]pyrimidin-7(6H)-one;

3-(((2S,3R)-3,4-dihydroxy-1-(methylthio)butan-2-ylamino)methyl)-1H-pyrazolo[4,3-d]pyrimidin-7(6H)-one;

3-(((2R,3R)-3,4-dihydroxy-2-(methylthiomethyl)butylamino)methyl)-1H-pyrazolo[4,3-d]pyrimidin-7(6H)-one;

3-(((2S,3S)-3,4-dihydroxy-2-(methylthiomethyl)butylamino)methyl)-1H-pyrazolo[4,3-d]pyrimidin-7(6H)-one;

3-(((2R,3S)-3,4-dihydroxy-2-(methylthiomethyl)butylamino)methyl)-1H-pyrazolo[4,3-d]pyrimidin-7(6H)-one;

3-(((2S,3R)-3,4-dihydroxy-2-(methylthiomethyl)butylamino)methyl)-1H-pyrazolo[4,3-d]pyrimidin-7(6H)-one;

2-amino-7-(((2R,3R)-3,4-dihydroxy-2-(methylthiomethyl)butylamino)methyl)-3H-pyrrolo[3,2-d]pyrimidin-4(5H)-one;

2-amino-7-(((2S,3S)-3,4-dihydroxy-2-(methylthiomethyl)butylamino)methyl)-3H-pyrrolo[3,2-d]pyrimidin-4(5H)-one;

2-amino-7-(((2R,3S)-3,4-dihydroxy-2-(methylthiomethyl)butylamino)methyl)-3H-pyrrolo[3,2-d]pyrimidin-4(5H)-one;

2-amino-7-(((2S,3R)-3,4-dihydroxy-2-(methylthiomethyl)butylamino)methyl)-3H-pyrrolo[3,2-d]pyrimidin-4(5H)-one;

7-(((2R,3R)-3,4-dihydroxy-2-(methylthiomethyl)butylamino)methyl)-3H-pyrrolo[3,2-d]pyrimidin-4(5H)-one;

7-(((2S,3S)-3,4-dihydroxy-2-(methylthiomethyl)butylamino)methyl)-3H-pyrrolo[3,2-d]pyrimidin-4(5H)-one;

7-(((2R,3S)-3,4-dihydroxy-2-(methylthiomethyl)butylamino)methyl)-3H-pyrrolo[3,2-d]pyrimidin-4(5H)-one;

7-(((2S,3R)-3,4-dihydroxy-2-(methylthiomethyl)butylamino)methyl)-3H-pyrrolo[3,2-d]pyrimidin-4(5H)-one;

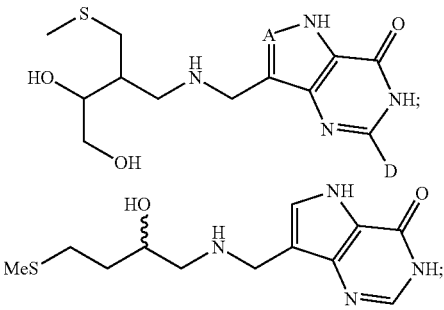

(RS)-7-((2-hydroxy-4-(methylthio)butylamino)methyl)-3H-pyrrolo[3,2-d]pyrimidin-4(5H)-one

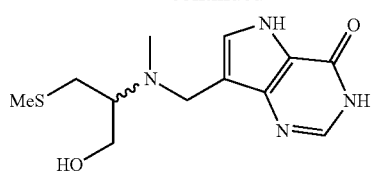

(RS)-7-(((1-hydroxy-3-(methylthio)
propan-2-yl)(methyl)amino)methyl)-3H-
pyrrolo[3,2-d]pyrimidin-4(5H)-one   and

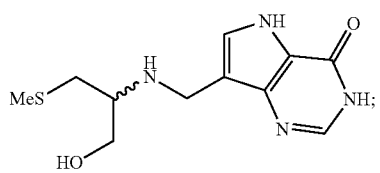

(RS)-7-(((1-hydroxy-3-(methylthio)
propan-2-ylamino)methyl)-3H-pyrrolo
[3,2-d]pyrimidin-4(5H)-one or a tautomer thereof; or a pharmaceutically acceptable salt thereof; or an ester thereof.

Additional examples of compounds of formula (VI) include:

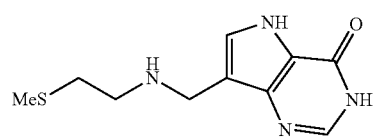

7-((2-(methylthio)ethylamino)methyl)-
3H-pyrrolo[3,2-d]pyrimidin-4(5H)-one

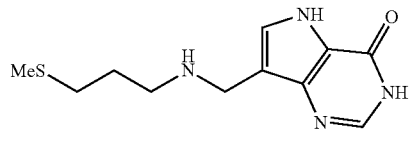

7-((3-(methylthio)propylamino)methyl)-
3H-pyrrolo[3,2-d]pyrimidin-4(5H)-one

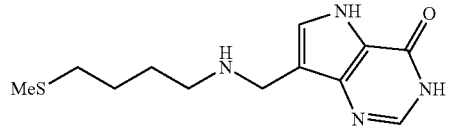

7-((4-(methylthio)butylamino)methyl)-
3H-pyrrolo[3,2-d]pyrimidin-4(5H)-one

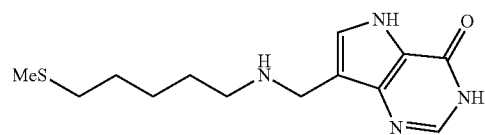

7-((5-(methylthio)pentylamino)methyl)-
3H-pyrrolo[3,2-d]pyrimidin-4(5H)-one

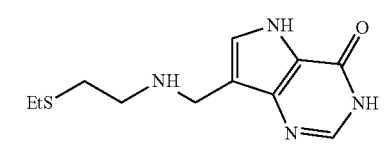

7-((2-(ethylthio)ethylamino)methyl)-
3H-pyrrolo[3,2-d]pyrimidin-4(5H)-one

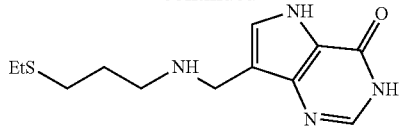

7-((3-(ethylthio)propylamino)methyl)-
3H-pyrrolo[3,2-d]pyrimidin-4(5H)-one

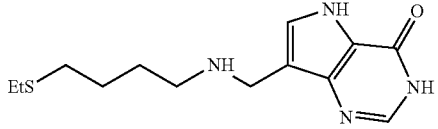

7-((4-(ethylthio)butylamino)methyl)-
3H-pyrrolo[3,2-d]pyrimidin-4(5H)-one

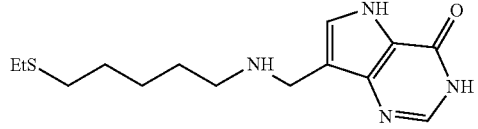

7-((5-(ethylthio)pentylamino)methyl)-
3H-pyrrolo[3,2-d]pyrimidin-4(5H)-one

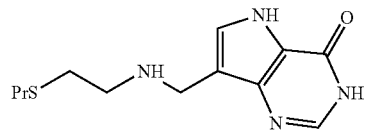

7-((2-(propylthio)ethylamino)methyl)-
3H-pyrrolo[3,2-d]pyrimidin-4(5H)-one

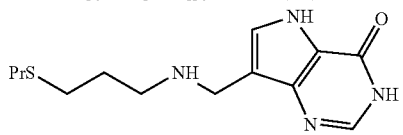

7-((3-(propylthio)propylamino)methyl)-
3H-pyrrolo[3,2-d]pyrimidin-4(5H)-one

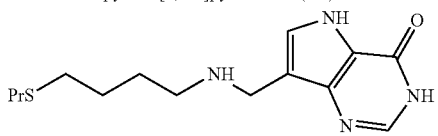

7-((4-(propylthio)butylamino)methyl)-
3H-pyrrolo[3,2-d]pyrimidin-4(5H)-one

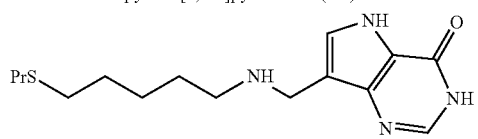

7-((5-(propylthio)pentylamino)methyl)-
3H-pyrrolo[3,2-d]pyrimidin-4(5H)-one

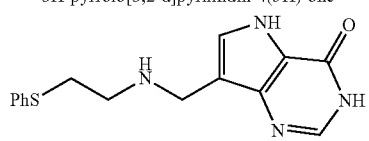

7-((2-(phenylthio)ethylamino)methyl)-
3H-pyrrolo[3,2-d]pyrimidin-4(5H)-one

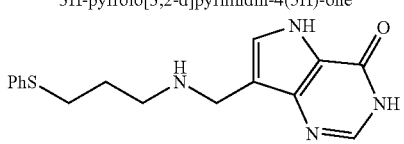

7-((3-(phenylthio)propylamino)methyl)-
3H-pyrrolo[3,2-d]pyrimidin-4(5H)-one

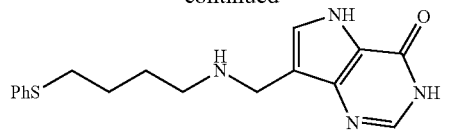

7-((4-(phenylthio)butylamino)methyl)-
3H-pyrrolo[3,2-d]pyrimidin-4(5H)-one

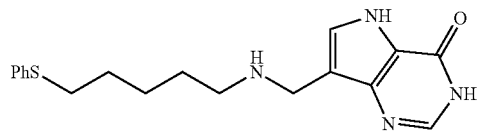

7-((5-(phenylthio)pentylamino)methyl)-
3H-pyrrolo[3,2-d]pyrimidin-4(5H)-one

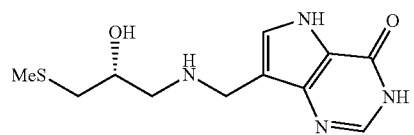

(R)-7-((2-hydroxy-3-(methylthio)propylamino)
methyl)-3H-pyrrolo[3,2-d]pyrimidin-4(5H)-one

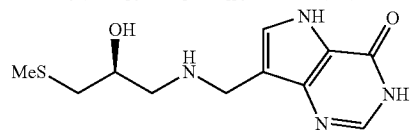

(S)-7-((2-hydroxy-3-(methylthio)propylamino)
methyl)-3H-pyrrolo[3,2-d]pyrimidin-4(5H)-one

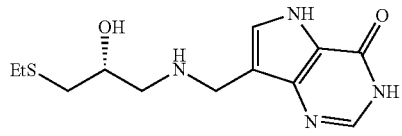

(R)-7-((3-(ethylthio)-2-hydroxypropylamino)
methyl)-3H-pyrrolo[3,2-d]pyrimidin-4(5H)-one

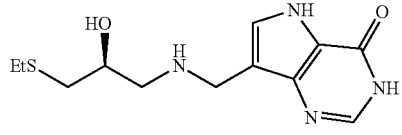

(S)-7-((3-(ethylthio)-2-hydroxypropylamino)
methyl)-3H-pyrrolo[3,2-d]pyrimidin-4(5H)-one

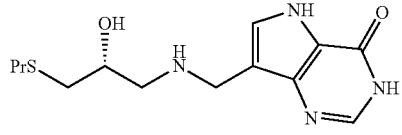

(R)-7-((2-hydroxy-3-(propylthio)propylamino)
methyl)-3H-pyrrolo[3,2-d]pyrimidin-4(5H)-one

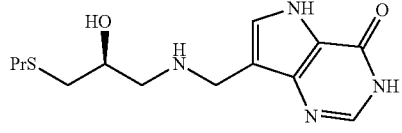

(S)-7-((2-hydroxy-3-(propylthio)propylamino)
methyl)-3H-pyrrolo[3,2-d]pyrimidin-4(5H)-one

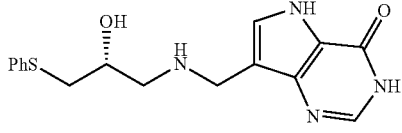

(R)-7-((2-hydroxy-3-(phenylthio)propylamino)
methyl)-3H-pyrrolo[3,2-d]pyrimidin-4(5H)-one

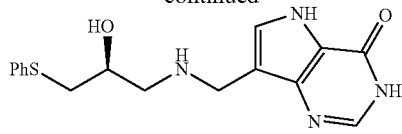

(S)-7-((2-hydroxy-3-phenylthio)propylamino)
methyl)-3H-pyrrolo[3,2-d]pyrimidin-4(5H)-one

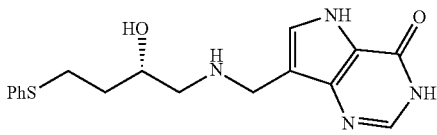

(S)-7-((2-hydroxy-4-(phenylthio)butylamino)
methyl)-3H-pyrrolo[3,2-d]pyrimidin-4(5H)-one

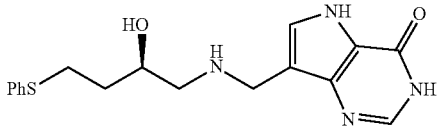

(R)-7-((2-hydroxy-4-(phenylthio)butylamino)
methyl)-3H-pyrrolo[3,2-d]pyrimidin-4(5H)-one

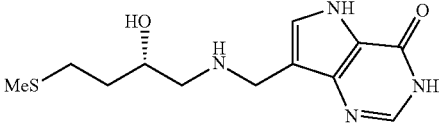

(S)-7-((2-hydroxy-4-(methylthio)butylamino)
methyl)-3H-pyrrolo[3,2-d]pyrimidin-4(5H)-one

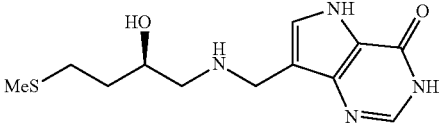

(R)-7-((2-hydroxy-4-(methylthio)butylamino)
methyl)-3H-pyrrolo[3,2-d]pyrimidin-4(5H)-one

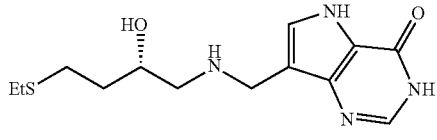

(S)-7-((4-ethylthio)-2-hydroxybutylamino)
methyl)-3H-pyrrolo[3,2-d]pyrimidin-4(5H)-one

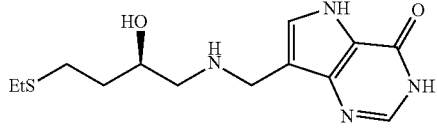

(R)-7-((4-ethylthio)-2-hydroxybutylamino)
methyl)-3H-pyrrolo[3,2-d]pyrimidin-4(5H)-one

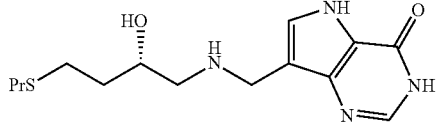

(S)-7-((2-hydroxy-4-(propylthio)butylamino)
methyl)-3H-pyrrolo[3,2-d]pyrimidin-4(5H)-one

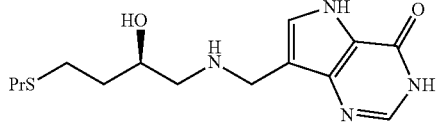

(R)-7-((2-hydroxy-4-(propylthio)butylamino)
methyl)-3H-pyrrolo[3,2-d]pyrimidin-4(5H)-one -continued

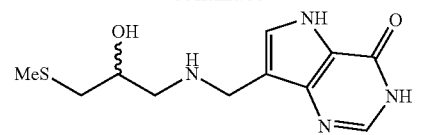

(RS)-7-((2-hydroxy-3-(methylthio)propylamino)
methyl)-3H-pyrrolo[3,2-d]pyrimidin-4(5H)-one

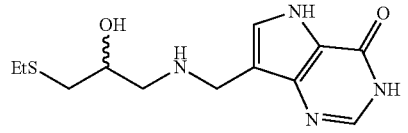

(RS)-7-((3-ethylthio-2-(hydroxypropylamino)
methyl)-3H-pyrrolo[3,2-d]pyrimidin-4(5H)-one

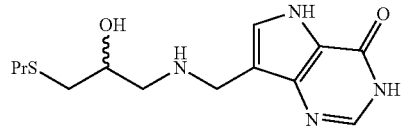

(RS)-7-((2-hydroxy-3-(propylthio)propylamino)
methyl)-3H-pyrrolo[3,2-d]pyrimidin-4(5H)-one

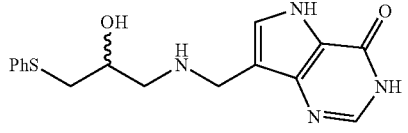

(RS)-7-((2-hydroxy-3-(phenylthio)propylamino)
methyl)-3H-pyrrolo[3,2-d]pyrimidin-4(5H)-one

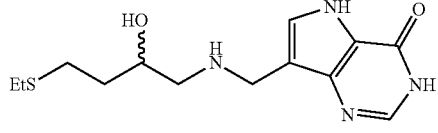

(RS)-7-((4-ethylthio-2-hydroxybutylamino)
methyl)-3H-pyrrolo[3,2-d]pyrimidin-4(5H)-one

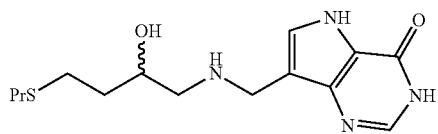

(RS)-7-((2-hydroxy-4-(propylthio)butylamino)
methyl)-3H-pyrrolo[3,2-d]pyrimidin-4(5H)-one

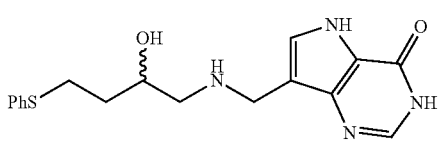

(RS)-7-((2-hydroxy-4-(phenylthio)butylamino)
methyl)-3H-pyrrolo[3,2-d]pyrimidin-4(5H)-one

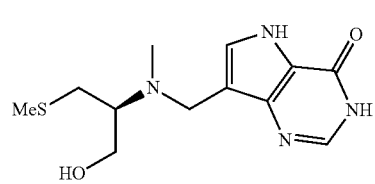

(S)-7-(((1-hydroxy-3-(methylthio)
propan-2-yl)(methyl)amino)methyl)-3H-
pyrrolo[3,2-d]pyrimidin-4(5H)-one -continued

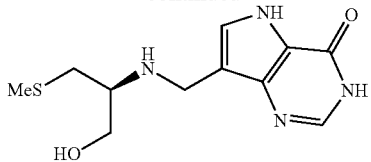

(S)-7-(((1-hydroxy-3-(methylthio)
propan-2-ylamino)methyl)-3H-
pyrrolo[3,2-d]pyrimidin-4(5H)-one

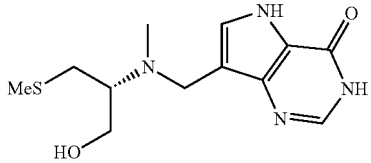

(R)-7-(((1-hydroxy-3-(methylthio)
propan-2-yl)(methyl)amino)methyl)-
3H-pyrrolo[3,2-d]pyrimidin-4(5H)-one

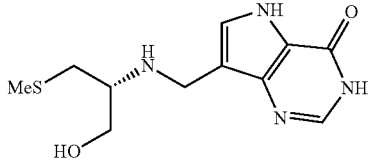

(R)-7-(((1-hydroxy-3-(methylthio)
propan-2-ylamino)methyl)-3H-
pyrrolo[3,2-d]pyrimidin-4(5H)-one

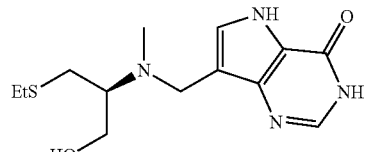

(S)-7-(((1-(ethylthio)-3-hydroxypropan-
2-yl)(methyl)amino)methyl)-3H-
pyrrolo[3,2-d]pyrimidin-4(5H)-one

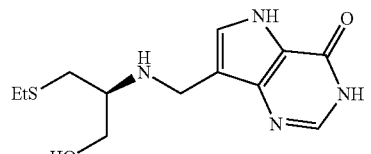

(S)-7-((1-(ethylthio)-3-hydroxypropan-
2-ylamino)methyl)-3H-pyrrolo
[3,2-d]pyrimidin-4(5H)-one

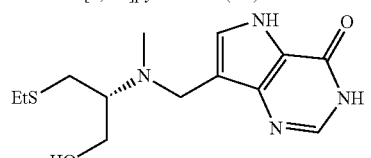

(R)-7-(((1-(ethylthio)-3-hydroxypropan-
2-yl)(methyl)amino)methyl)-3H-
pyrrolo[3,2-d]pyrimidin-4(5H)-one

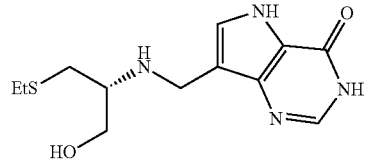

(R)-7-((1-(ethylthio)-3-hydroxypropan-
2-ylamino)methyl)-3H-pyrrolo
[3,2-d]pyrimidin-4(5H)-one

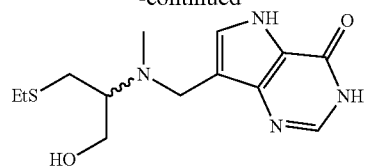

(RS)-7-(((1-(ethylthio)-3-hydroxypropan-
2-yl)(methyl)amino)methyl)-3H-
pyrrolo[3,2-d]pyrimidin-4(5H)-one

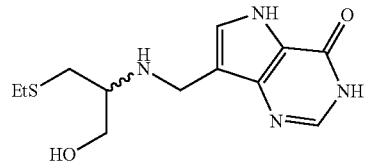

(RS)-7-((1-(ethylthio)-3-hydroxypropan-
2-ylamino)methyl)-3H-pyrrolo
[3,2-d]pyrimidin-4(5H)-one

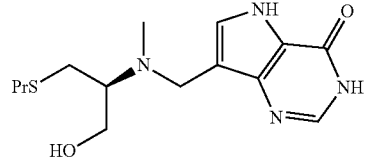

(S)-7-(((1-hydroxy-3-(propylthio)
propan-2-yl)(methyl)amino)methyl)-
3H-pyrrolo[3,2-d]pyrimidin-4(5H)-one

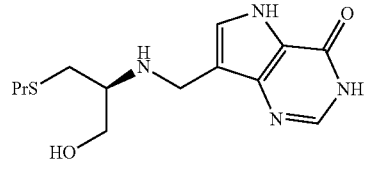

(S)-7-((1-hydroxy-3-(propylthio)
propan-2-ylamino)methyl)-3H-
pyrrolo[3,2-d]pyrimidin-4(5H)-one

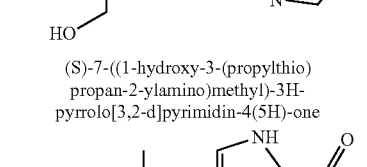

(R)-7-(((1-hydroxy-3-(propylthio)
propan-2-yl)(methyl)amino)methyl)-
pyrrolo[3,2-d]pyrimidin-4(5H)-one

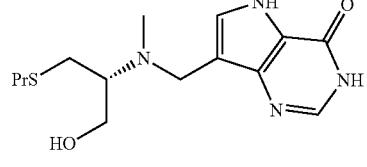

(R)-7-((1-hydroxy-3-(propylthio)
propan-2-ylamino)methyl)-3H-
pyrrolo[3,2-d]pyrimidin-4(5H)-one

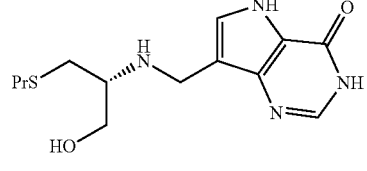

(RS)-7-(((1-hydroxy-3-(propylthio)
propan-2-yl)(methyl)amino)methyl)-3H-
pyrrolo[3,2-d]pyrimidin-4(5H)-one

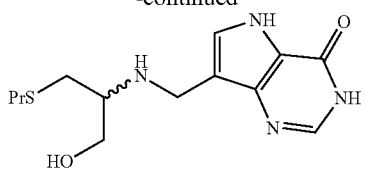

(RS)-7-((1-(hydroxy)-3-(propylthio)
propan-2-ylamino)methyl)-3H-
pyrrolo[3,2-d]pyrimidin-4(5H)-one

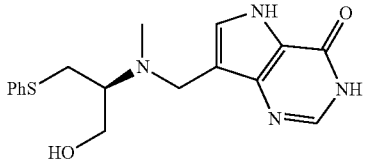

(S)-7-(((1-(hydroxy)-3-(phenylthio)
propan-2-yl)(methyl)amino)methyl)-
3H-pyrrolo[3,2-d]pyrimidin-4(5H)-one

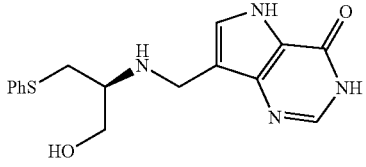

(S)-7-((1-(hydroxy)-3-(phenylthio)
propan-2-ylamino)methyl)-3H-
pyrrolo[3,2-d]pyrimidin-4(5H)-one

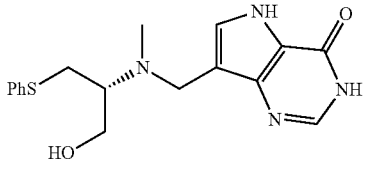

(R)-7-(((1-(hydroxy)-3-(phenylthio)
propan-2-yl)(methyl)amino)methyl)-
pyrrolo[3,2-d]pyrimidin-4(5H)-one

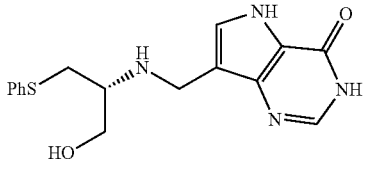

(R)-7-((1-(hydroxy)-3-(phenylthio)
propan-2-ylamino)methyl)-3H-
pyrrolo[3,2-d]pyrimidin-4(5H)-one

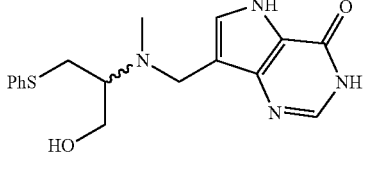

(RS)-7-(((1-(hydroxy)-3-(phenylthio)
propan-2-yl)(methyl)amino)methyl)-3H-
pyrrolo[3,2-d]pyrimidin-4(5H)-one

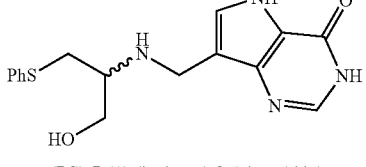

(RS)-7-((1-(hydroxy)-3-(phenylthio)
propan-2-ylamino)methyl)-3H-
pyrrolo[3,2-d]pyrimidin-4(5H)-one -continued

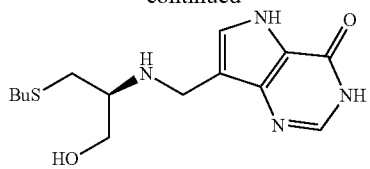

(S)-7-((1-(butylthio)-3-
hydroxypropan-2-ylamino)methyl)-
3H-pyrrolo[3,2-d]pyrimidin-4(5H)-one

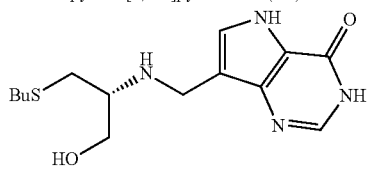

(R)-7-((1-(butylthio)-3-
hydroxypropan-2-ylamino)methyl)-
3H-pyrrolo[3,2-d]pyrimidin-4(5H)-one

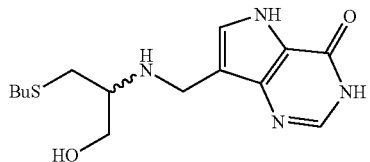

(RS)-7-((1-(butylthio)-3-
hydroxypropan-2-ylamino)methyl)-
3H-pyrrolo[3,2-d]pyrimidin-4(5H)-one

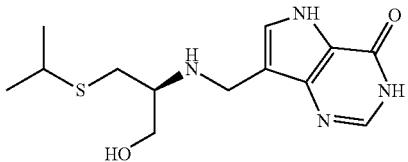

(S)-7-((1-hydroxy-3-(isopropylthio)-
propan-2-ylamino)methyl)-3H-
pyrrolo[3,2-d]pyrimidin-4(5H)-one

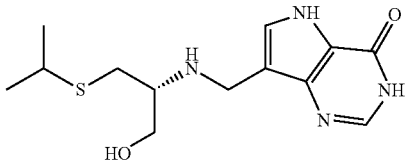

(R)-7-((1-hydroxy-3-(isopropylthio)-
propan-2-ylamino)methyl)-3H-
pyrrolo[3,2-d]pyrimidin-4(5H)-one

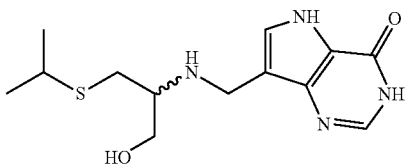

(RS)-7-((1-hydroxy-3-(isopropylthio)-
propan-2-ylamino)methyl)-3H-
pyrrolo[3,2-d]pyrimidin-4(5H)-one

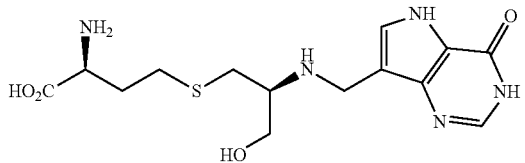

(S)-2-amino-4-((S)-3-hydroxy-2-((4-oxo-
4,5-dihydro-3H-pyrrolo[3,2-d]pyrimidin-7-
yl)methylamino)propylthio)butanoic acid -continued

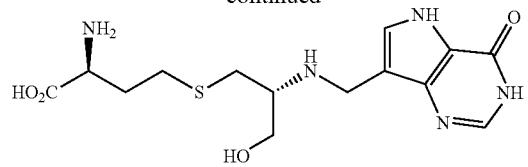

(S)-2-amino-4-((R)-3-hydroxy-2-((4-oxo-
4,5-dihydro-3H-pyrrolo[3,2-d]pyrimidin-7-
yl)methylamino)propylthio)butanoic acid

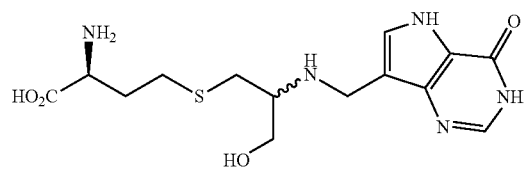

(S)-2-amino-4-((RS)-3-hydroxy-2-((4-oxo-
4,5-dihydro-3H-pyrrolo[3,2-d]pyrimidin-7-
yl)methylamino)propylthio)butanoic acid

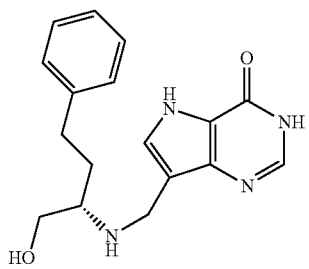

(S)-7-((1-hydroxy-4-phenylbutan-
2-ylamino)methyl)-3H-pyrrolo
[3,2-d]pyrimidin-4(5H)-one

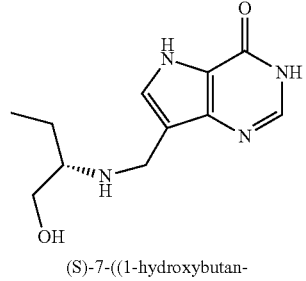

(S)-7-((1-hydroxybutan-
2-ylamino)methyl)-3H-pyrrolo
[3,2-d]pyrimidin-4(5H)-one

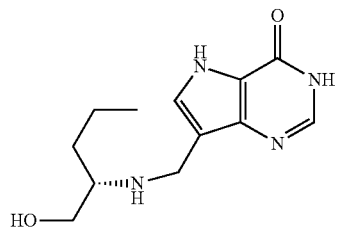

(S)-7-((1-hydroxypentan-
2-ylamino)methyl)-3H-pyrrolo
[3,2-d]pyrimidin-4(5H)-one -continued

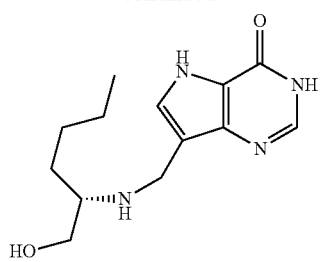

(S)-7-((1-hydroxyhexan-
2-ylamino)methyl)-3H-pyrrolo
[3,2-d]pyrimidin-4(5H)-one

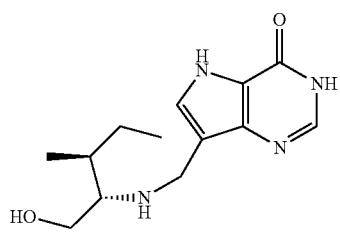

7-(((2S,3S)-1-hydroxy-3-methylpentan-
2-ylamino)methyl)-3H-pyrrolo
[3,2-d]pyrimidin-4(5H)-one

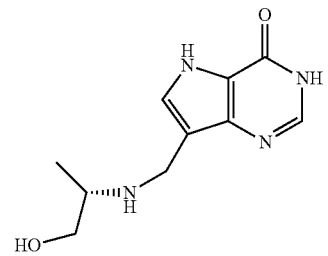

(S)-7-((1-hydroxypropan-2-
ylamino)methyl)-3H-pyrrolo
[3,2-d]pyrimidin-4(5H)-one

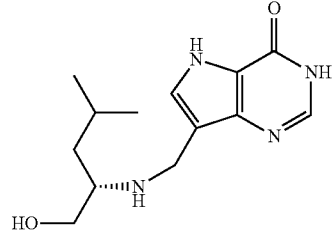

(S)-7-((1-hydroxy-4-methylpentan-
2-ylamino)methyl)-3H-pyrrolo
[3,2-d]pyrimidin-4(5H)-one

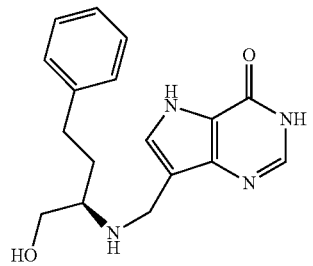

(R)-7-((1-hydroxy-4-phenylbutan-
2-ylamino)methyl)-3H-pyrrolo
[3,2-d]pyrimidin-4(5H)-one -continued

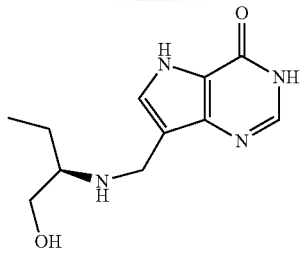

(R)-7-((1-hydroxybutan-
2-ylamino)methyl)-3H-pyrrolo
[3,2-d]pyrimidin-4(5H)-one

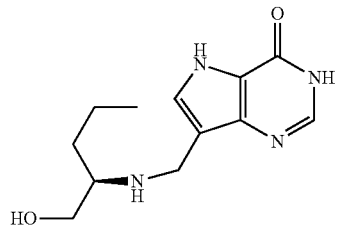

(R)-7-((1-hydroxypentan-
2-ylamino)methyl)-3H-pyrrolo
[3,2-d]pyrimidin-4(5H)-one

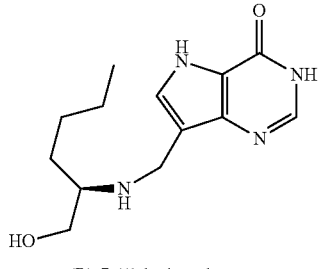

(R)-7-((1-hydroxyhexan-
2-ylamino)methyl)-3H-pyrrolo
[3,2-d]pyrimidin-4(5H)-one

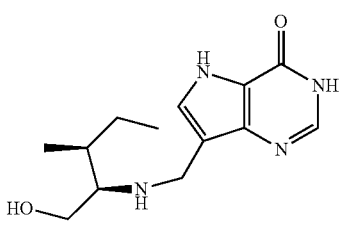

7-(((2R,3S)-1-hydroxy-3-methylpentan-
2-ylamino)methyl)-3H-pyrrolo
[3,2-d]pyrimidin-4(5H)-one

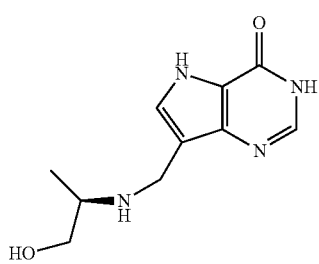

(R)-7-((1-hydroxypropan-2-
ylamino)methyl)-3H-pyrrolo
[3,2-d]pyrimidin-4(5H)-one

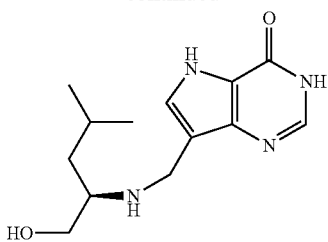

(R)-7-((1-hydroxy-4-methylpentan-2-ylamino)methyl)-3H-pyrrolo[3,2-d]pyrimidin-4(5H)-one

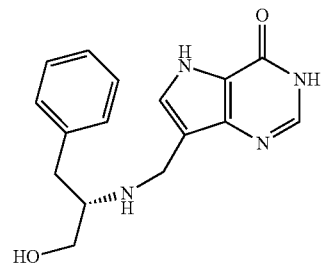

(S)-7-((1-hydroxy-3-phenylpropan-2-ylamino)methyl)-3H-pyrrolo[3,2-d]pyrimidin-4(5H)-one

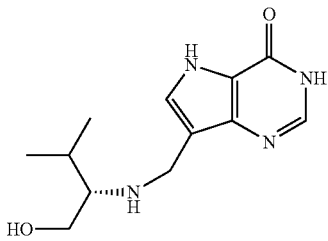

(S)-7-((1-hydroxy-3-methylbutan-2-ylamino)methyl)-3H-pyrrolo[3,2-d]pyrimidin-4(5H)-one

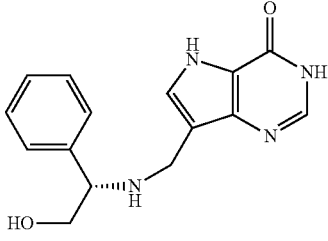

(S)-7-((2-hydroxy-1-phenyethylamino)methyl)-3H-pyrrolo[3,2-d]pyrimidin-4(5H)-one

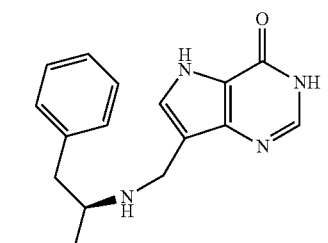

(R)-7-((1-hydroxy-3-phenylpropan-2-ylamino)methyl)-3H-pyrrolo[3,2-d]pyrimidin-4(5H)-one

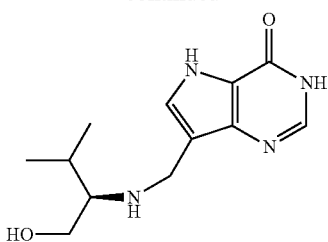

(R)-7-((1-hydroxy-3-methylbutan-2-ylamino)methyl)-3H-pyrrolo[3,2-d]pyrimidin-4(5H)-one

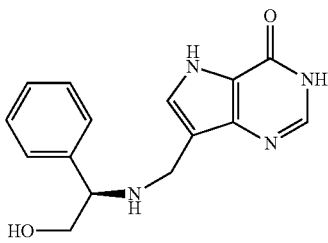

(R)-7-((2-hydroxy-1-phenylethylamino)methyl)-3H-pyrrolo[3,2-d]pyrimidin-4(5H)-one

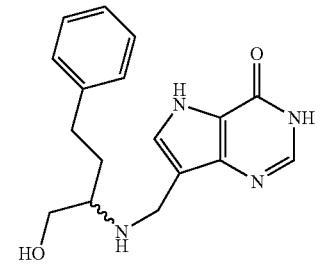

(RS)-7-((1-hydroxy-4-phenylbutan-2-ylamino)methyl)-3H-pyrrolo[3,2-d]pyrimidin-4(5H)-one

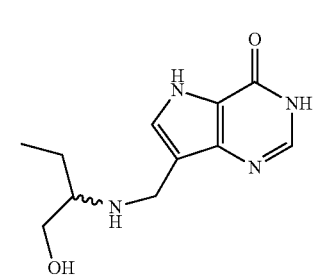

(RS)-7-((1-hydroxybutan-2-ylamino)methyl)-3H-pyrrolo[3,2-d]pyrimidin-4(5H)-one

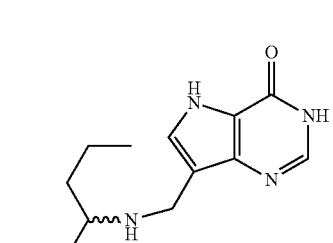

(RS)-7-((1-hydroxypentan-2-ylamino)methyl)-3H-pyrrolo[3,2-d]pyrimidin-4(5H)-one

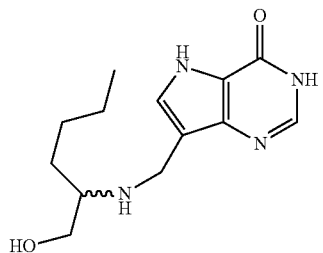

(RS)-7-((1-hydroxyhexan-
2-ylamino)methyl)-3H-pyrrolo
[3,2-d]pyrimidin-4(5H)-one

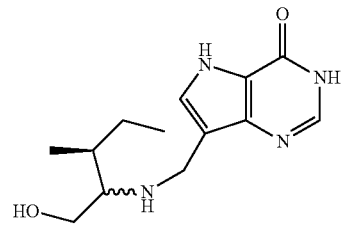

7-((2RS,3S)-1-hydroxy-3-
methylpentan-2-ylamino)methyl)-3H-
pyrrolo[3,2-d]pyrimidin-4(5H)-one

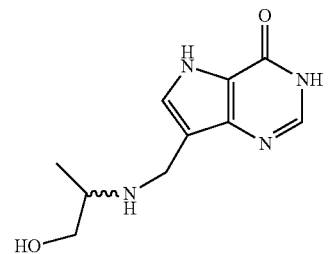

(RS)-7-((1-hydroxypropan-2-
ylamino)methyl)-3H-pyrrolo
[3,2-d]pyrimidin-4(5H)-one

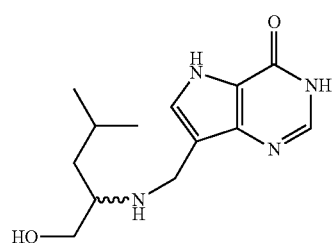

(RS)-7-((1-hydroxy-4-methylpentan-
2-ylamino)methyl)-3H-pyrrolo
[3,2-d]pyrimidin-4(5H)-one

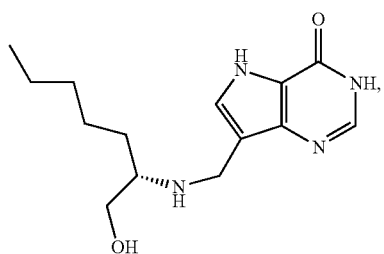

(S)-7-((1-hydroxyheptan-
2-ylamino)methyl)-3H-pyrrolo
[3,2-d]pyrimidin-4(5H)-one and

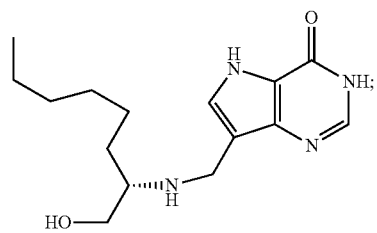

(S)-7-((1-hydroxyoctan-
2-ylamino)methyl)-3H-pyrrolo
[3,2-d]pyrimidin-4(5H)-one or a tautomer thereof; or a pharmaceutically acceptable salt thereof; or an ester thereof.

Preferred compounds include those having the structure:

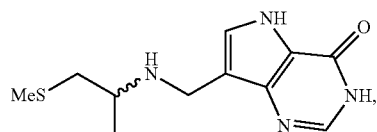

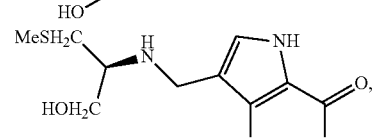

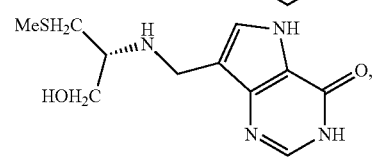

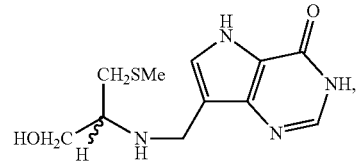

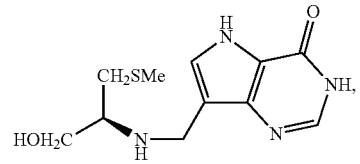

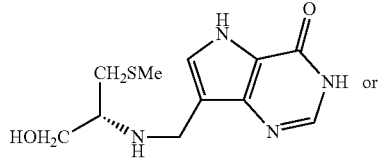

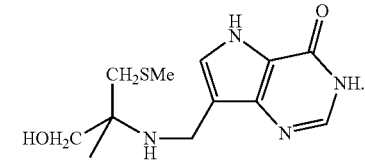

In another embodiment, the MTIP inhibitor comprises a compound having formula (VII):

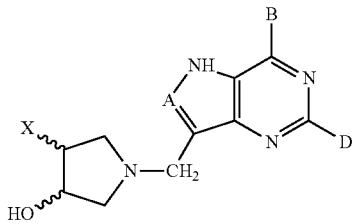

(VII)

wherein X is an alkyl, cycloalkyl, aralkyl, aralkenyl, alkenyl, alkynyl or aryl group, each of which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole and $NR^2R^3$ group, where each alkylthio, arylthio and aralkylthio group is optionally substituted with one or more alkyl, halogen, amino, hydroxy, or alkoxy groups; or X is $SR^1$; or X is $NR^2R^3$; $R^1$, $R^2$ and $R^3$ are independently selected from the group consisting of alkyl, alkenyl, alkynyl, aralkyl or aryl, each of which is optionally substituted with one or more substituents selected from the group consisting of hydroxy, alkoxy, thiol, alkylthio, arylthio, aralkylthio, halogen, carboxylic acid, carboxylate alkyl ester, nitro, cyano and $NR^2R^3$ group, where each alkylthio, arylthio and aralkylthio group is optionally substituted with one or more alkyl, halogen, amino, hydroxy, or alkoxy groups; A is N or CH; B is OH; D is H, OH, $NH_2$, or $SCH_3$; provided that X is not $CH_2Z$, where Z is selected from OH, hydrogen, halogen, $SQ^1$, $OQ^2$ and $Q^3$, where $Q^1$ is an optionally substituted alkyl, aralkyl or aryl group, $Q^2$ is an optionally substituted alkyl group and $Q^3$ is an optionally substituted alkyl group; or a tautomer thereof, or a pharmaceutically acceptable salt thereof, or an ester prodrug form thereof.

Preferred compounds include those of formula (VIIa):

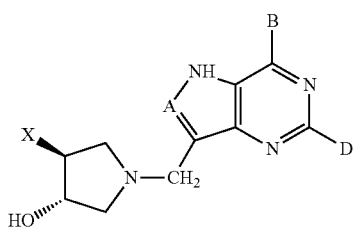

(VIIa)

wherein A, B, D and X are as defined above.

Alternatively, preferably the compound is a compound of formula (VIIb):

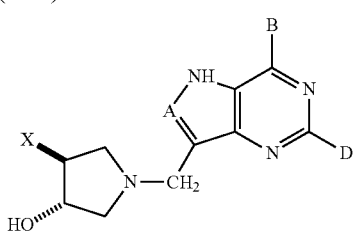

(VIIb)

wherein A, B, D and X are as defined above.

Preferably, in the above formulae (VII), (VIIa) and (VIIb), $Q^1$ is an optionally substituted alkyl, aralkyl or aryl group, $Q^2$ is an optionally substituted alkyl group and $Q^3$ is an optionally substituted alkyl group. For example, $Q^1$, $Q^2$ or $Q^1$ may be optionally substituted with one or more: halogens, e.g. chlorine or fluorine; alkyl groups, e.g. methyl or cyclohexylmethyl; COOH; or $NH_2$.

Preferably A is CH. It is further preferred that D is H.

Preferably, X is an alkenyl or alkynyl group each of which is optionally substituted with one or more substituents selected from the group consisting of hydroxy, alkoxy, thiol, alkylthio, arylthio, aralkylthio, halogen, carboxylic acid, carboxylate alkyl ester, nitro, or $NR^2R^3$ group, where each alkylthio, arylthio and aralkylthio group is optionally substituted with one or more alkyl, halogen, amino, hydroxy, or alkoxy groups. X may be, for example, a lower alkenyl group, e.g. a vinyl, allyl or prop-1-en-2-yl group. X may be, for example, a lower alkynyl group, e.g. an ethynyl group or a propyn-3-yl group.

Alternatively, preferably, X is an alkyl group which is optionally substituted with one or more substituents selected from the group consisting of hydroxy, alkoxy, thiol, alkylthio, arylthio, or aralkylthio, e.g. benzylthio, halogen, carboxylic acid, carboxylate alkyl ester, nitro or $NR^2R^3$ group, where each alkylthio, arylthio and aralkylthio group is optionally substituted with one or more alkyl, halogen, amino, hydroxy or alkoxy groups. X may be, for example, a lower alkyl group, e.g. ethyl, propyl, butyl, isobutyl, pent-3-yl or an alkyl group substituted with a cycloalkyl group, e.g. cyclohexyl group, e.g. X may be cyclohexanemethyl. Alternatively, X may be, for example, an alkyl group which is substituted with an aralkylthio group, e.g X may be 3-benzylthiopropyl group.

Alternatively, preferably, X is an alkyl group which is optionally substituted with one or more substituents selected from the group consisting of cycloalkyl, e.g. cycloalkyl in which one or more of the ring carbon atoms is substituted by a heteroatom chosen from nitrogen, oxygen or sulfur. In some examples, X may be cyclopropanemethyl, 2-tetrahydrofuranmethyl, 2-thietanemethyl, 3-piperidinemethyl, 2-pyrrolidinemethyl or 4-thiacyclohexanemethyl.

Alternatively, preferably, X is a cycloalkyl group which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole and $NR^2R^3$ group, where each alkylthio, arylthio and aralkylthio group is optionally substituted with one or more alkyl, halogen, amino, hydroxy or alkoxy groups. X may be, for example, a cyclopropyl, cyclobutyl, cyclopentyl, cyclohexyl or adamantyl group.

Alternatively, preferably, X may be a cycloalkyl group where one or more of the ring atoms is a heteroatom, e.g. a nitrogen, sulfur or oxygen atom. X may be, for example, 2-tetrahydrofuranyl, 2-tetrahydrothienyl, 1,2-dithian-3-yl, piperidin-3-yl, thietan-2yl, 2-pyrrolidinyl or 4-thiacyclohexyl.

Alternatively, preferably, X is an aryl group which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole and $NR^2R^3$ group, where each alkylthio, arylthio and aralkylthio group is optionally substituted with one or more alkyl, halogen, amino, hydroxy, or alkoxy groups. The aryl group may be a heteroaryl group, where one or more of the ring carbon atoms is a heteroatom, e.g. a nitrogen, sulfur or oxygen atom. X may be, for example, a phenyl group or an optionally substituted triazole group. Where X is an optionally substituted triazole group the triazole ring may optionally be substituted with one or more substituents selected from the group consisting of aryl group, e.g. phenyl; alkyl group, e.g. a lower alkyl group, e.g. a propyl group which may optionally be substituted with one or more substituents selected from aryl, hydroxyl, or alkoxy; aralkyl group, e.g. benzyl; or cycloalkyl group. Where X is an optionally substituted triazole group, the triazole ring may be attached to the pyrrolidine ring via either a triazole ring nitrogen or a triazole ring carbon atom.

Alternatively, preferably, X is $SR^1$, where $R^1$ is alkyl, alkenyl, alkynyl, aralkyl or aryl, each of which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole and $NR^2R^3$ group, where each alkylthio, arylthio and aralkylthio group is optionally substituted with one or more alkyl, halogen, amino, hydroxy or alkoxy groups. For example, X may be phenylthio, 4-chlorophenylthio, 4-fluorophenylthio, 3-fluorophenylthio, 4-methylphenylthio, ethylthio, propylthio, butylthio, pentylthio, 3-fluoropropylthio, 2,3-dihydroxypropylthio, 3-hydroxypropylthio, 2-hydroxyethylthio, allylthio or 4-chlorobutylthio.

Alternatively, preferably, X is $NR^2R^3$, where $R^2$ and $R^3$ are independently selected from alkyl, alkenyl, alkynyl, aralkyl or aryl, each of which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole and $NR^2R^3$ group, where each alkylthio, arylthio and aralkylthio group is optionally substituted with one or more alkyl, halogen, amino, hydroxy, or alkoxy groups. For example, X may be diethylamino, ethylamino, propylamino, butylamino, 2-hydroxyethylamino, 3-hydroxypropylamino, 2,3-dihydroxypropylamino, 3-fluoroethylamino, trifluoroethylamino, bis(2-hydroxyethyl)amino, 3-butenylamino, benzylamino, 4-fluorobenzylamino, 4-chlorobenzylamino, or N-methyl-benzylamino.

Examples of compounds of formula (VII) include:
(±)-trans-1-[(9-Deazahypoxanthin-9-yl)methyl]-3-hydroxy-4-phenylpyrrolidine;
(±)-trans-1-[(9-Deazahypoxanthin-9-yl)methyl]-3-hydroxy-4-vinylpyrrolidine;
(±)-trans-1-[(9-Deazahypoxanthin-9-yl)methyl]-4-ethynyl-3-hydroxypyrrolidine;
(±)-trans-4-Allyl-1-[(9-deazahypoxanthin-yl)methyl]-3-hydroxypyrrolidine;
(±)-trans-4-Cyclopropyl-1-[(9-deazahypoxanthin-9-yl)methyl]-3-hydroxypyrrolidine;
(±)-trans-4-Cyclohexyl-1-[(9-deazahypoxanthin-9-yl)methyl]-3-hydroxypyrrolidine;
(±)-trans-4-Cyclohexylmethyl-1-[(9-deazahypoxanthin-9-yl)methyl]-3-hydroxypyrrolidine;
(±)-trans-1-[(9-Deazahypoxanthin-9-yl)methyl]-3-hydroxy-4-(prop-1-en-2-yl)-pyrrolidine;
(±)-trans-4-Butyl-1-[(9-Deazahypoxanthin-9-yl)methyl]-3-hydroxypyrrolidine;
(±)-trans-1-[(9-Deazahypoxanthin-9-yl)methyl]-3-hydroxy-4-(pent-3-yl)-pyrrolidine;
(±)-trans-4-Cyclopentyl-1-[9-deazahypoxanthin-9-yl)methyl]-3-hydroxypyrrolidine;
(±)-trans-1-[(9-Deazahypoxanthin-9-yl)methyl]-3-hydroxy-4-(1H-1,2,3-triazol-1-yl)pyrrolidine;
(±)-trans-4-(1-Benzyl-1H-1,2,3-triazol-4-yl)-1-[(9-deazahypoxanthin-9-yl)methyl]-3-hydroxypyrrolidine;
(±)-trans-4-(3-Benzylthiopropyl)-1-[9-deazahypoxanthin-9-yl)methyl]-3-hydroxypyrrolidine;
(±)-cis-1-[(9-Deazahypoxanthin-9-yl)methyl]-4-ethyl-3-hydroxypyrrolidine;
(3R,4S)-1-[(9-Deazahypoxanthin-9-yl)methyl]-3-hydroxy-4-phenylpyrrolidine;
(3R,4S)-1-[(9-Deazahypoxanthin-9-yl)methyl]-3-hydroxy-4-vinylpyrrolidine;
(3R,4S)-1-[(9-Deazahypoxanthin-9-yl)methyl]-4-ethynyl-3-hydroxy-pyrrolidine;
(3R,4S)-4-Allyl-1-[9-deazahypoxanthin-9-yl)methyl]-3-hydroxypyrrolidine;
(3R,4S)-4-Cyclopropyl-1-[(9-deazahypoxanthin-9-yl)methyl]-3-hydroxypyrrolidine;
(3R,4S)-4-Cyclohexyl-1-[9-deazahypoxanthin-9-yl)methyl]-3-hydroxypyrrolidine;
(3R,4S)-1-[(9-Deazahypoxanthin-9-yl)methyl]-3-hydroxy-4-(prop-1-en-2-yl)-pyrrolidine;
(3R,4S)-1-[(9-Deazahypoxanthin-9-yl)methyl]-3-hydroxy-4-(pent-3-yl)-pyrrolidine;
(3R,4S)-4-Cyclopentyl-1-[9-deazahypoxanthin-9-yl)methyl]-3-hydroxypyrrolidine;
(3S,4S)-1-[(9-Deazahypoxanthin-9-yl)methyl]-3-hydroxy-4-(1H-1,2,3-triazol-1-yl)pyrrolidine;
(3R,4R)-4-(1-Benzyl-1H-1,2,3-triazol-4-yl)-1-[(9-deazahypoxanthin-9-yl)methyl]-3-hydroxypyrrolidine;
(±)-trans-1-[(9-Deazahypoxanthin-9-yl)methyl]-3-hydroxy-4-(2-methylpropyl)pyrrolidine;
(±)-trans-4-Butyl-1-[(9-deazahypoxanthin-9-yl)methyl]-3-hydroxypyrrolidine;
(±)-trans-1-[(9-Deazahypoxanthin-9-yl)methyl]-3-hydroxy-4-(thiazol-2-yl)-pyrrolidine;
(3R,4S)-1-[(9-Deazahypoxanthin-9-yl)methyl]-3-hydroxy-4-(thiazol-2-yl)-pyrrolidine;
(±)-trans-1-[(9-Deazahypoxanthin-9-yl)methyl]-3-hydroxy-4-(tetrazol-5-yl)-pyrrolidine;
(3R,4R)-1-[(9-Deazahypoxanthin-9-yl)methyl]-3-hydroxy-4-(tetrazol-5-yl)-pyrrolidine; and
(3S,4R)-1-[(9-Deaza-adenin-9-yl)methyl]-4-ethyl-3-hydroxypyrrolidine;
or a tautomer thereof, or a pharmaceutically acceptable salt thereof, or an ester thereof.

Preferably, the MTIP inhibitor has an IC50 value greater than or equal to 50 nanomolar for human purine nucleoside phosphorylase (PNP), as determined by the method described in Bantia, et al., Immunopharmacology 35, p. 54, paragraph 2.1 (1996) (52). Preferably, the MTIP inhibitor has an IC50 value greater than or equal to 50 nanomolar for 5'-methylthioadenosine nucleosidase (MTAN). Preferably, the MTIP inhibitor has an IC50 value greater than or equal to 50 nanomolar for 5'-methylthioadenosine phosphorylase (MTAP). "IC50" means the molar concentration of an inhibitor needed to reduce the rate of product formation by 50% from the uninhibited reaction in an assay mixture containing a target enzyme.

The active compounds may be administered to a subject, such as a human, by a variety of routes, including orally, parenterally, by inhalation spray, topically, rectally, nasally, buccally or via an implanted reservoir. The specific dosage required for any particular patient will depend upon a variety of factors, including the patient's age and body weight.

For oral administration the compounds can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried cornstarch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant.

The compounds may also be administered topically. Carriers for topical administration of the compounds of include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

The compounds can be administered to plants, for example, by spraying the plant surfaces with the compound and a carrier of the type normally used in agricultural applications, such as, for example, water or an oil. Typical concentrations can be, for example, 1-100 grams of inhibitor per 1000 gallons of plant spray.

The present invention also provides for the use of a subgrowth inhibiting amount of an MTIP inhibitor for treating bacterial infections in a subject. The present invention further provides for the use of a subgrowth inhibiting amount of an MTIP inhibitor for the preparation of a composition for treating bacterial infections in a subject.

The invention also provides a method for determining whether or not a compound is a candidate for treating an infection caused by bacteria that use 5'-methylthioinosine phosphorylase (MTIP) in a quorum sensing pathway, the method comprising determining whether or not the compound inhibits MTIP, wherein a compound that inhibits MTIP is a candidate for treating an infection caused by bacteria that use MTIP in a quorum sensing pathway and wherein a compound that does not inhibit MTIP is not a candidate for treating an infection caused by bacteria that use MTIP in a quorum sensing pathway.

Preferably, the MTIP inhibitor has an IC50 value less than 50 nanomolar for MTIP. Preferably, the MTIP inhibitor has an IC50 value greater than or equal to 50 nanomolar for human purine nucleoside phosphorylase (PNP), as determined by the method described in Bantia, et al., Immunopharmacology 35, p. 54, paragraph 2.1 (1996) (52). Preferably, the MTIP inhibitor has an IC50 value greater than or equal to 50 nanomolar for 5'-methylthioadenosine nucleosidase (MTAN). Preferably, the MTIP inhibitor has an IC50 value greater than or equal to 50 nanomolar for 5'-methylthioadenosine phosphorylase (MTAP). "IC50" means the molar concentration of an inhibitor needed to reduce the rate of product formation by 50% from the uninhibited reaction in an assay mixture containing a target enzyme.

An "inhibitor" is a substance that when added to an assay mixture for a target enzyme causes a decrease in the rate of product formation by interaction with the enzyme.

The bacteria can be, for example, *Pseudomonas aeruginosa*, *Pseudomonas syringae* or *Xanthomonas campestris*.

Enzymatic assays can be carried out, for example, as described herein in Experimental Details.

The invention also provides a chemical compound of formula (I)

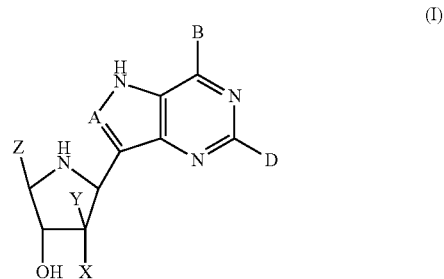

wherein A is CH or N; B is OH; D is chosen from H, OH, $NH_2$, or $SCH_3$; X is OH; Y is H; and Z is Q, where Q is a methyl group which is substituted with one or more substituents selected from the group consisting of methoxy, amino and carboxy, or Q is an optionally substituted, alkenyl, aralkyl, aralkenyl, aryl group or $C_2$-$C_{10}$ alkyl group, each of which is optionally substituted with one or more substituents selected from hydroxy, halogen, methoxy, amino, carboxy, or straight- or branched-chain $C_1$-$C_6$ alkyl; or a tautomer thereof; or a pharmaceutically acceptable salt thereof; or an ester thereof.

Preferably, D is H. It is also preferred that A is CH. It is further preferred that D is H and A is CH.

Preferably, Q is an optionally substituted alkyl group, e.g. a $C_2$-$C_6$ alkyl group such as an ethyl, propyl or butyl group. It is also preferred that Q is an alkyl group substituted with one or more amino groups. Preferably Q is an alkyl group substituted with one or more amino and one or more carboxy groups, e.g. —$(CH_2)_4CH(NH_2)COOH$.

Alternatively, preferably, Q is an optionally substituted aralkyl group, e.g. a phenylethyl or benzyl group. In still other preferred embodiments, Q is an optionally substituted aralkenyl group, e.g. a phenylethenyl group, e.g. a cis-phenylethenyl group or a trans-phenylethenyl group.

Preferably, the compound has an IC50 value greater than or equal to 50 nanomolar for human purine nucleoside phosphorylase (PNP), as determined by the method described in Bantia, et al., Immunopharmacology 35, p. 54, paragraph 2.1 (1996) (52). Preferably, the compound has an IC50 value greater than or equal to 50 nanomolar for 5'-methylthioadenosine nucleosidase (MTAN). Preferably, the compound has an IC50 value greater than or equal to 50 nanomolar for 5'-methylthioadenosine phosphorylase (MTAP).

The invention also provides a compound selected from the group consisting of
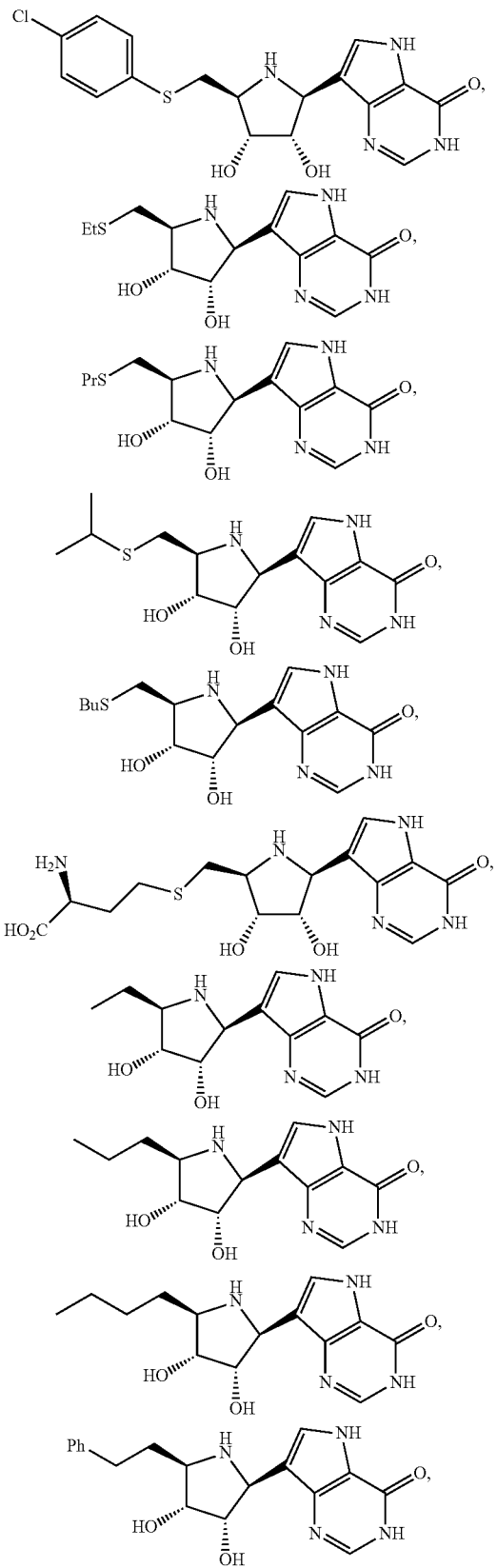
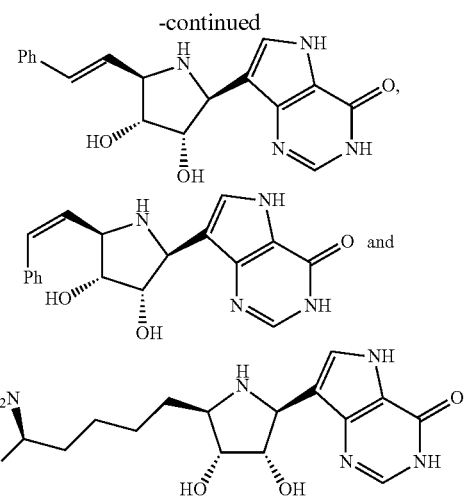
or a tautomer thereof; or a pharmaceutically acceptable salt thereof; or an ester thereof.
The invention further provides a compound selected from the group consisting of
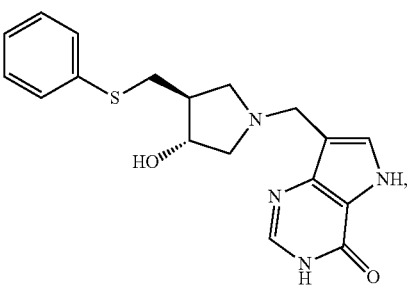
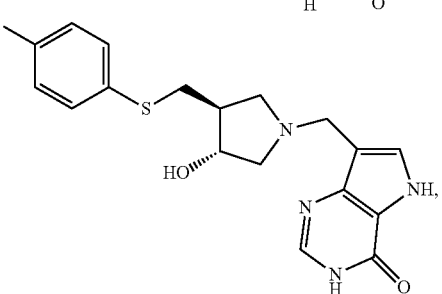
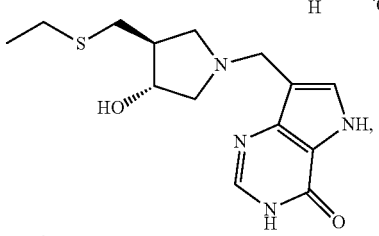
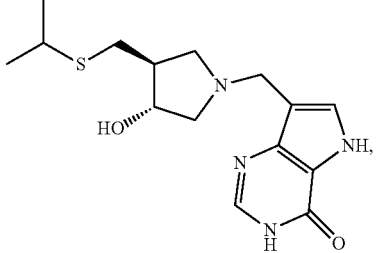

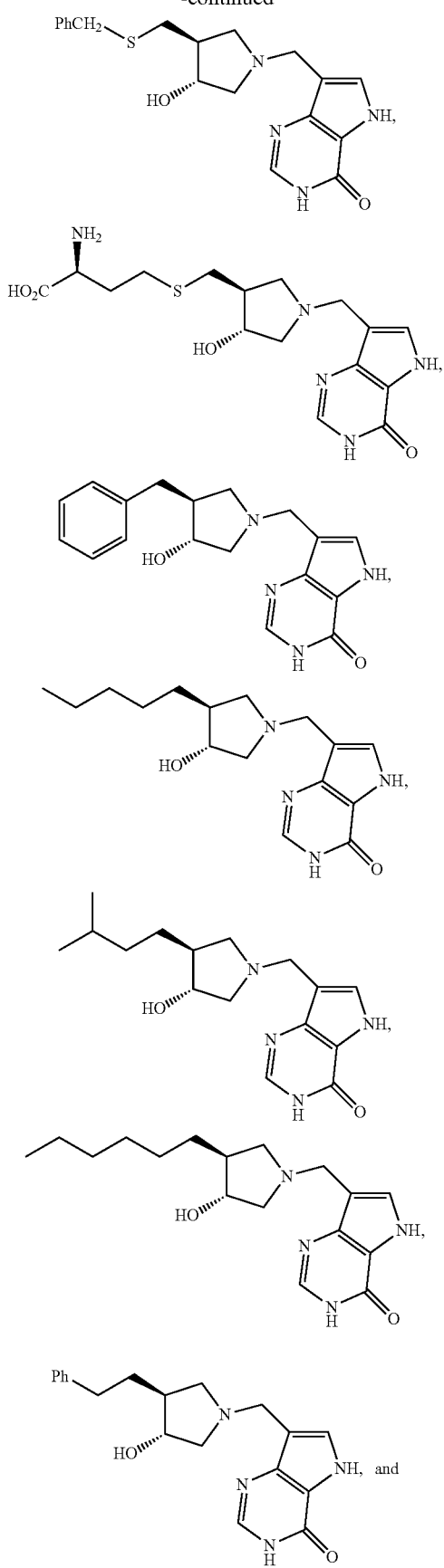
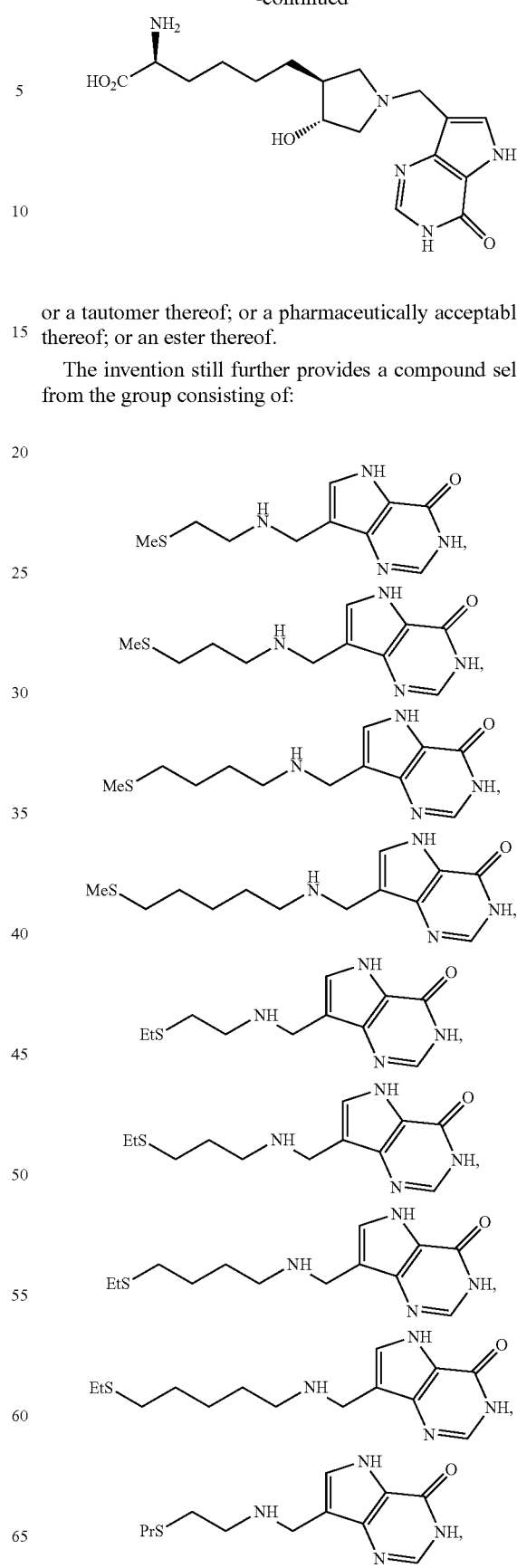
or a tautomer thereof; or a pharmaceutically acceptable salt thereof; or an ester thereof.
The invention still further provides a compound selected from the group consisting of:

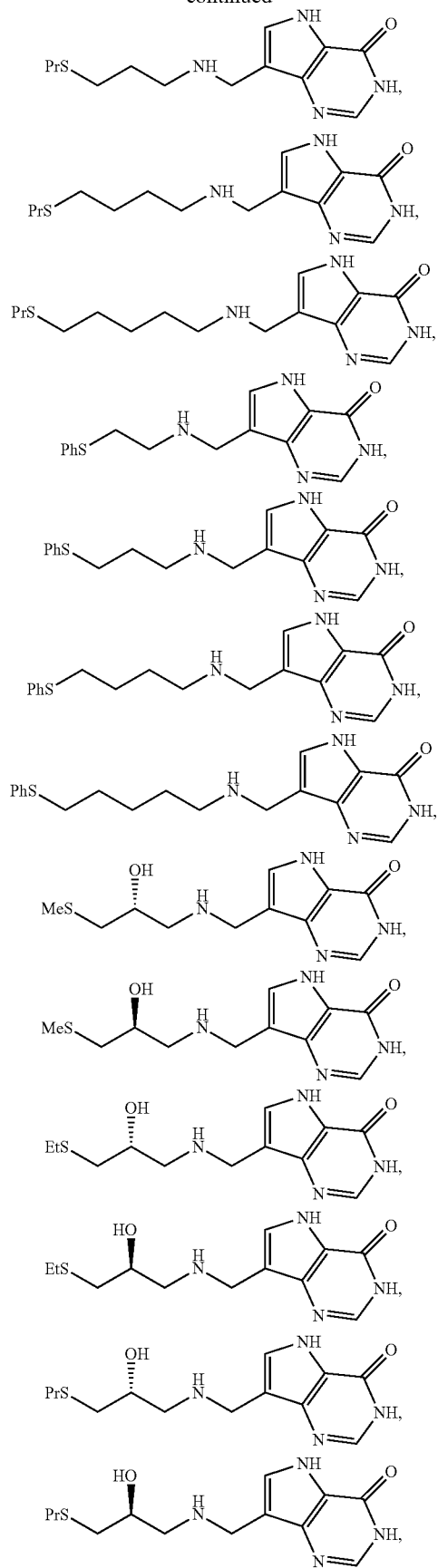
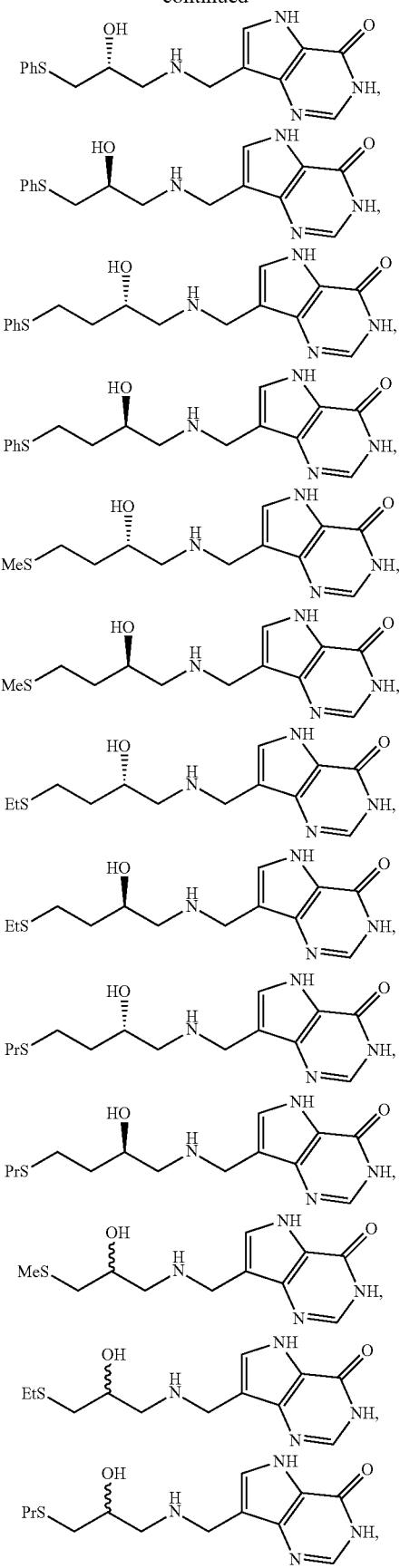

57
-continued
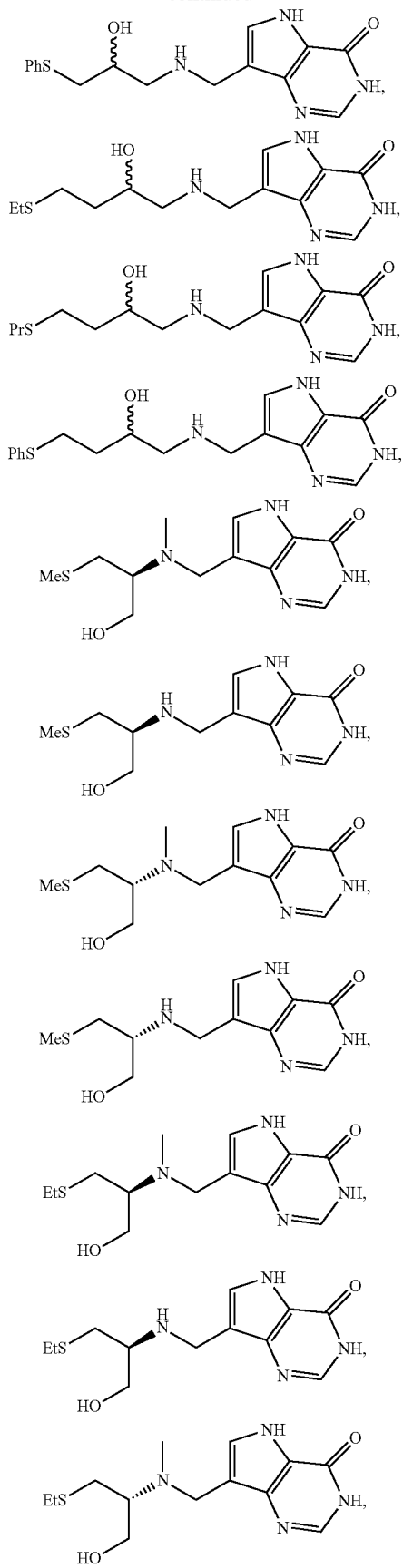
58
-continued
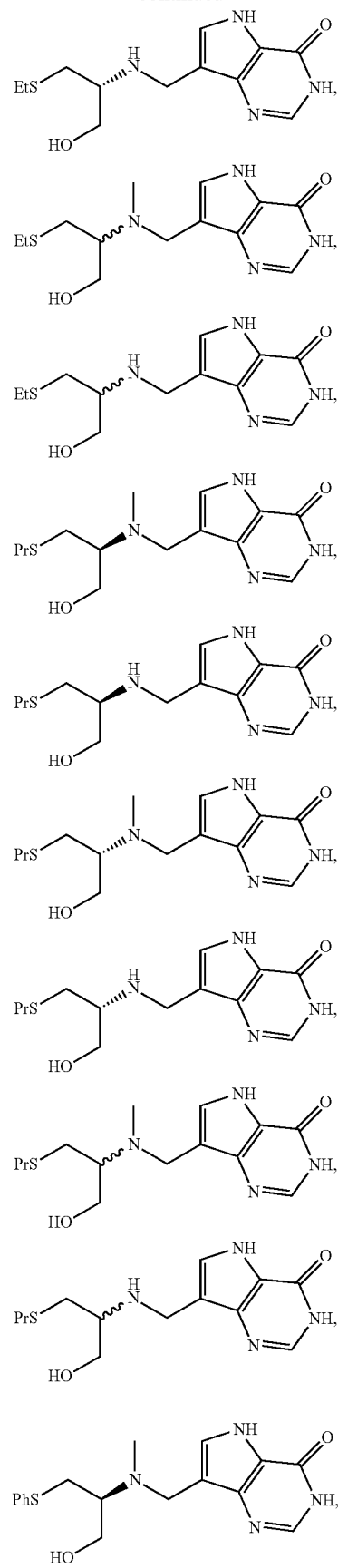

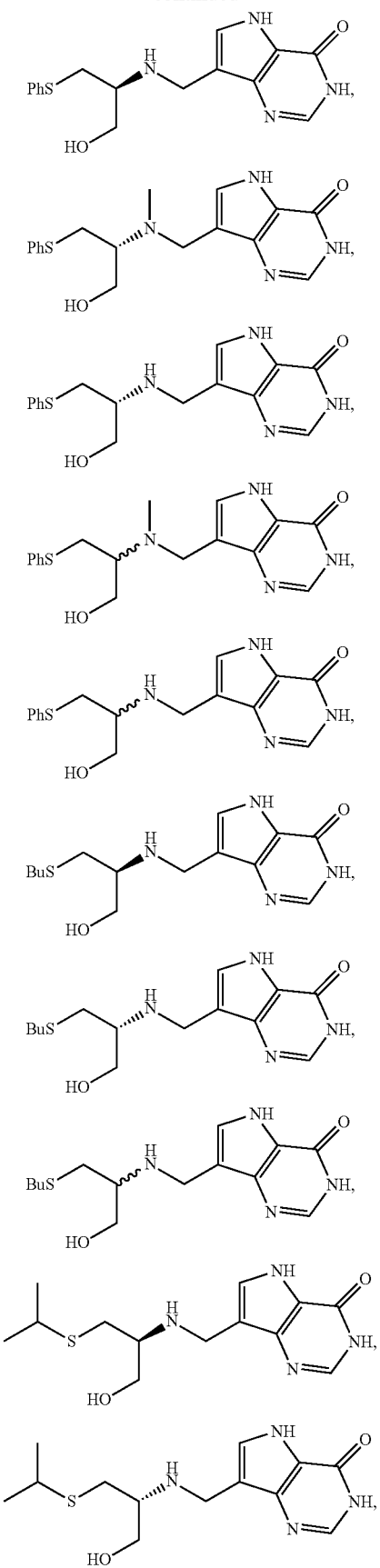
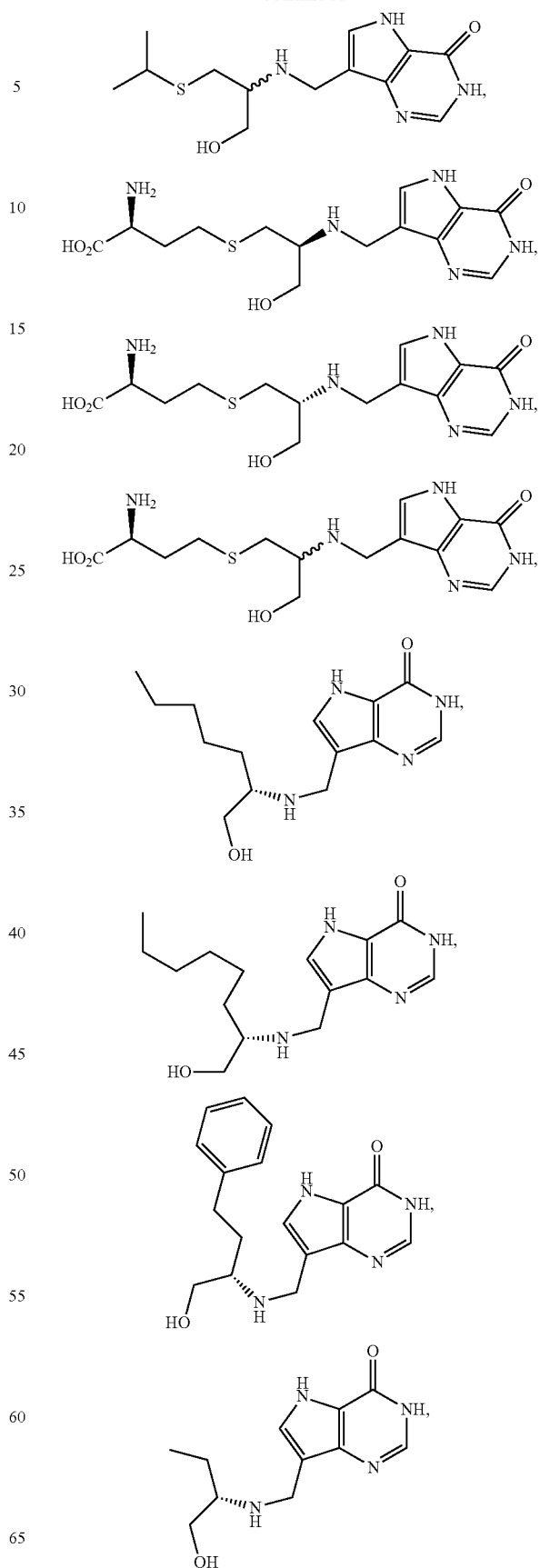

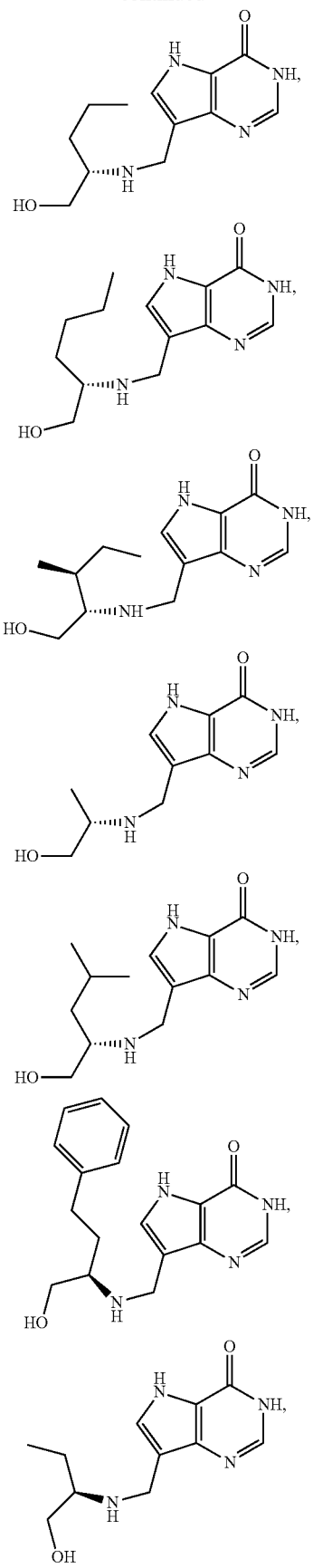
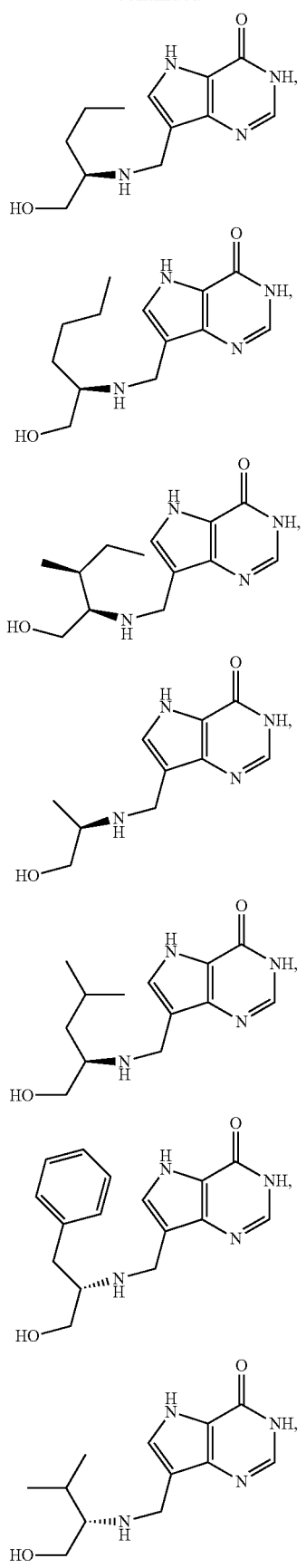

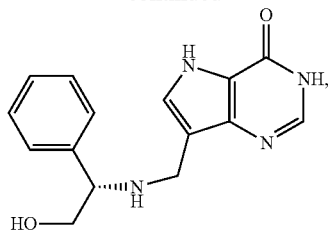
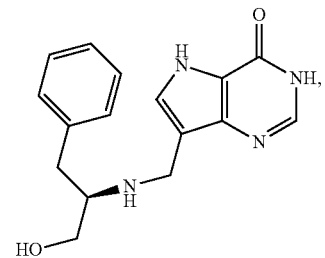
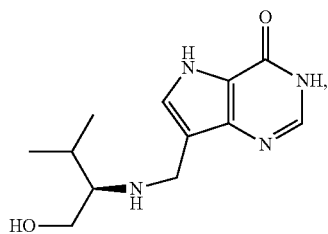
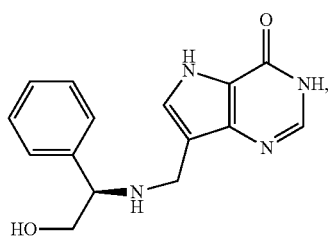
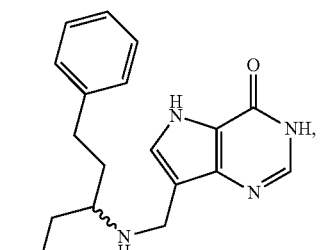
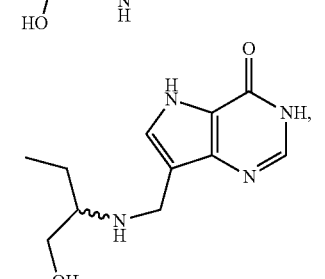
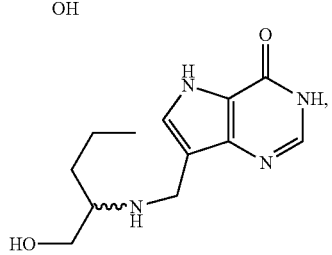

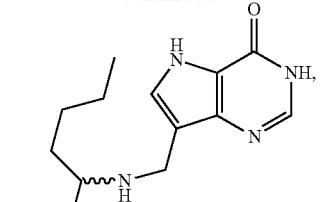
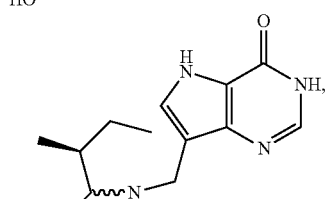
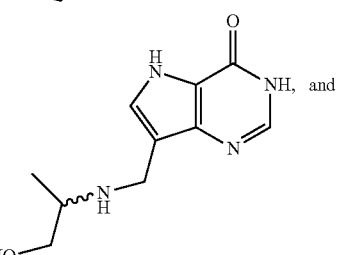, and
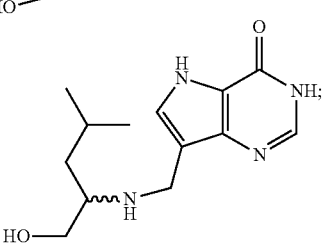

or a tautomer thereof; or a pharmaceutically acceptable salt thereof; or an ester thereof.

The invention also provides a pharmaceutical composition comprising any one or more of the compounds disclosed herein and a pharmaceutically acceptable salt.

The term "pharmaceutically acceptable salt" is intended to apply to non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

The invention also provides a pharmaceutical composition or an agrochemical composition comprising one or more of the compounds disclosed herein and a pharmaceutically or agrochemically acceptable carrier. The compound can be present in a concentration that is a sub-bacterial-growth inhibiting amount of a 5'-methylthioinosine phosphorylase (MTIP) inhibitor.

The invention also provides a pharmaceutical composition or an agrochemical composition comprising any one or more of the compounds disclosed herein and one or more additional compounds, such as 5'-methylthio-inosine or 5'-methylthioadenosine.

The invention also provides methods for treating infections caused by bacteria that use 5'-methylthioinosine phosphorylase (MTIP) in a quorum sensing pathway comprising coadministering to a subject having the infection a sub-growth inhibiting amount of a 5'-methylthioinosine phosphorylase (MTIP) inhibitor, and 5'-methylthioinosine and/or 5'-methylthioadenosine.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

*P. aeruginosa* is an unusual bacterium as it possesses a putative 5'-methylthioadenosine phosphorylase (MTAP: PA3004 gene) instead of MTAN. MTAP is rare in bacteria and common in mammals, while MTAN is not found in mammals. The action of MTAP on MTA would be functionally similar to that of MTAN by relieving MTA product inhibition of AHL synthase and SAM recycling in *P. aeruginosa* (18). The PA3004 gene in *P. aeruginosa* PAO1 was originally annotated from sequence homology, followed by metabolic studies in PA3004 mutants that mistakenly supported the MTAP assignment (19, 20). The present study establishes the PA3004 encoded protein to be 5'-methylthioinosine phosphorylase (MTIP) rather than MTA phosphorylase (MTAP). Examination of MTA metabolism in *P. aeruginosa* using [8-$^{14}$C]MTA confirmed that the pathway involves MTIP. Transition state analogue inhibitors with picomolar $K_i$ values for PaMTIP are described.

Materials and Methods

Chemicals.

MT-ImmH, PhT-ImmH, and MT-DADMe-ImmH were synthesized by the Carbohydrate Chemistry Team of Industrial Research Ltd, Lower Hutt, New Zealand (FIG. 1). [8-$^{14}$C]MTA was synthesized as described previously (21). All other chemicals and reagents were obtained from Sigma or Fisher Scientific, and were of reagent grade.

Plasmid Construction.

A synthetic gene was designed based on the predicated protein sequence of NP_251694.1 in NCBI, annotated as MTAP of *Pseudomonas aeruginosa* PAO1. The synthetic gene was obtained in a pJexpress414 expression vector from DNA2.0 Inc. This construct encodes an additional 14 amino acids at the N-terminus which includes a His$_6$ tag and a TEV cleavage site.

Enzyme Purification and Preparation.

BL21-CodonPlus(DE3)-RIPL *E. coli* were transformed with the above plasmid and grown overnight at 37° C. in 50 mL of LB medium with 100 µg/mL Ampicillin. The culture was transferred into 1 L of LB/Ampicillin medium and growth continued at 37° C. to an O.D.$_{600}$ of 0.7. Expression was induced by addition of 1 mM IPTG. After 4 hours at 37° C., the cells were harvested by centrifugation at 4500 g for 30 min. The cell pellet was suspended in 20 mL of 15 mM imidazole, 300 mM NaCl, and 50 mM phosphate, pH 8.0 (lysis buffer), with 2 tablets of EDTA-free protease inhibitor (from Roche Diagnostics) and lysozyme (from chicken egg) added to the mixture. Cells were disrupted twice with a French Press and centrifuged at 20,000 g for 30 min. The supernatant was loaded onto a 4 mL column of Ni-NTA Superflow resin previously equilibrated with 5 columns of lysis buffer. The column was washed with 5 volumes of 80 mM imidazole, 300 mM NaCl, and 50 mM phosphate, pH 8.0 (wash buffer), and enzyme was eluted with 3 volumes of 250 mM imidazole, 300 mM NaCl, and 50 mM phosphate, pH 8.0 (elution buffer). The purified enzyme (>95% purity on the basis of SDS-PAGE) was dialyzed against 50 mM Hepes, pH 7.4 and concentrated to 8 mg/ml. Enzyme was stored at −80° C. The extinction coefficient of target protein is 20.4 mM$^{-1}$cm$^{-1}$ at 280 nm, determined by ProtParam program from ExPASy.

Enzymatic Assays.

Product formation was monitored by conversion of hypoxanthine to uric acid by xanthine oxidase (22). The extinction coefficient of this assay was 12.9 mM$^{-1}$cm$^{-1}$ at 293 nm. Enzyme activity with adenosine or MTA as substrates was determined by conversion of adenine to 2,8-dihydroxyadenine using the same coupling enzyme (23). Its extinction coefficient at 293 nm was 15.2 mM$^{-1}$cm$^{-1}$. Reactions were carried out at 25° C. in 1 cm cuvettes, 1 mL volumes of 100 mM Hepes, pH 7.4, 100 mM phosphate, pH 7.4, variable concentrations of nucleoside substrate, 0.5 unit of xanthine oxidase, 5 mM DTT, and appropriate amounts of purified MTIP. Reactions were initiated by addition of enzyme and the initial rates were monitored with a CARY 300 UV-Visable spectrophotometer. Control rates (no PaMTIP) were subtracted from initial rates. $K_m$ and $k_{cat}$ values for PaMTIP were obtained by fitting initial rates to the Michaelis-Menten equation using GraFit 5 (Erithacus Software). Phosphate was found to be near saturation when present at 100 mM.

Inhibition Assays.

Assays for slow-onset inhibitors were carried out by adding 1 nM PaMTIP into reaction mixtures at 25° C. containing 100 mM Hepes, pH 7.4, 100 mM phosphate, pH 7.4, 2 mM MTI, 5 mM DTT, 0.5 unit of xanthine oxidase and variable inhibitor concentration. Inhibitors were present at >10 times the enzyme concentration, required to simplify data analysis (24). Assays for MTA inhibition used 200 µM MTI. Controls having no enzyme and no inhibitor were included in all of the inhibition assays. Inhibition constants were obtained by fitting initial rates with variable inhibitor concentrations to equation (1) using GraFit 5 (Erithacus Software):

$$\frac{v_i}{v_o} = \frac{[S]}{K_m + [S] + \frac{K_m[I]}{K_i}} \quad (1)$$

where $v_i$ is the initial rate in the presence of inhibitor, $v_o$ is the initial rate in the absence of inhibitor, $K_m$ is the Michaelis constant for MTI, [S] and [I] are MTI and inhibitor concentrations, respectively, and $K_i$ is the inhibition constant. Slow-onset inhibitors display a second phase of tighter binding after reaching a thermodynamic equilibrium with the enzyme. The equilibrium constant for the second binding phase is indicated as $K_i^*$. This constant was obtained by fitting initial final rates and inhibitor concentrations to equation (1) using GraFit 5 (22).

Protein Crystallization and Data Collection.

Recombinant PaMTIP (9 mg/ml) in 50 mM HEPES, pH 7.4 crystallized in 30% polyethylene glycol monomethyl ether 2000, and 0.1 M potassium thiocyanate in the presence of 5 mM MTI and 5 mM sulfate by sitting-drop vapor diffusion. Crystals were transferred to a fresh drop of crystallization solution supplemented with 20% glycerol and flash-cooled in liquid nitrogen. X-ray diffraction data were collected at Beamline X29A, Brookhaven National Laboratory and processed with the HKL2000 program suite (Table 1).

Structure Determination and Refinement.

The crystal structure of PaMTIP was determined by molecular replacement with Molrep using the published structure of *Sulfolobus tokodaii* MTAP (PDB:1V4N) as the search model (25). A model without catalytic site ligands was built by Phenix (26), followed by iterative rounds of manual model building and refinement in COOT and REFMAC5 (27, 28). Although PaMTIP was co-crystallized in the presence of sulfate and MTI to mimic the Michaelis complex of PaMTIP, based on ligand-omitted $F_o$-$F_c$ maps (contoured at 3σ) electron density was consistent with the presence of only a purine ring in the active site. PaMTIP was later confirmed to hydrolyze MTI under these conditions. Hypoxanthine was modeled in the active site of PaMTIP (Table 1).

MTA Catabolism Using [8-$^{14}$C]MTA.

*P. aeruginosa* PAO1 (ATCC number: 15692) was grown at 37° C. in LB medium for 16 hours. Cells were collected by centrifugation at 16100 g and washed twice with 100 mM phosphate, pH 7.4. Washed cells were lysed using BugBuster (Novagen). Cleared lysate (53 µL) was incubated with [8-$^{14}$C]MTA (10 µL containing approximately 0.1 µCi $^{14}$C) in 100 mM phosphate, pH 7.4, for 10 and 25 min. Reaction mixtures were quenched with perchloric acid (1.8 M final concentration) and neutralized with potassium hydroxide. Precipitates were removed by centrifugation and carrier hypoxanthine, adenine, MTI, and MTA were added to the cleared supernatant. Metabolites were resolved on a $C_{18}$ Luna HPLC column (Phenomenex) with a gradient of 5-52.8% acetonitrile in 20 mM ammonium acetate, pH 5.2. UV absorbance was detected at 260 nm and the retention times were 5.1 min for hypoxanthine, 7.5 min for adenine, 20.4 min for MTI, and 21.9 min for MTA. Fractions were collected in scintillation vials, dried, reconstituted in 200 µL deionized water prior to addition of 10 mL ULTIMA GOLD LSC-Cocktail and $^{14}$C was counted for three cycles at 20 minutes per cycle using a Tri-Carb 2910TR liquid scintillation analyzer. Control experiments replaced cell lysate by lysis buffer in reaction mixtures.

Results and Discussion

Annotation of PA3004 as a MTAP.

The PA3004 gene of *P. aeruginosa* PAO1 encodes a protein (NCBI ID of NP_251694.1) annotated as a "probable nucleoside phosphorylase" in PseudoCAP (29). It was later proposed to be an MTAP based on catabolism studies in mutant strains of *P. aeruginosa* (19, 20). PAO503 is a *P. aeruginosa* methionine-auxotroph. A new strain (PAO6422) was created by inactivating the PA3004 gene of PAO503. While PAO503 was complemented for growth on minimum medium with methionine, homocysteine or MTA, PAO6422 responded to methionine and homocysteine but was not complemented by MTA (20). These results supported an MTAP activity for the PA3004 encoded protein. The results also support a pathway of MTA→MTI→hypoxanthine+MTR-1-P→methionine, but this was not considered.

PA3004 Encodes a MTI Phosphorylase.

Here, the recombinant protein from PA3004 was purified and tested for substrate specificity (Table 2). The recombinant protein could not utilize MTA in the presence or absence of phosphate. The most favorable reaction was phosphorolysis of MTI with a $k_{cat}$ of 4.8 s$^{-1}$, of 2.6 µM ($k_{cat}/K_m$ of 1.8×10$^6$ M$^{-1}$s$^{-1}$). Enzyme was less active with inosine with a $k_{cat}$ of 0.57 s$^{-1}$ and a $K_m$ of 90 µM ($k_{cat}/K_m$ of 6.3×10$^3$ M$^{-1}$s$^{-1}$) and depended on phosphate for significant activity. The methylthio-group of MTI is important for both substrate binding and catalysis. Adenosine is a weak substrate with a $k_{cat}$ of 0.0549 s$^{-1}$ and a of 23 µM ($k_{cat}/K_m$ of 2.4×10$^3$ M$^{-1}$s$^{-1}$). Thus the protein encoded by PA3004 is a relatively specific MTI phosphorylase. The catalytic efficiency ($k_{cat}/K_m$) for MTI is 290 times larger than for inosine, the second best substrate. For comparison, the MTI phosphorylase activity of PfPNP (see below) has a $k_{cat}/K_m$ of 9.4×10$^4$ M$^{-1}$s$^{-1}$ for MTI and a $k_{cat}/K_m$ of 3.6×10$^5$ M$^{-1}$s$^{-1}$ for inosine.

MTI phosphorylase activity has been documented in *Caldariella acidophilan* MTAP, human MTAP, human PNP, and *P. falciparum* PNP, but in these, MTI is a relatively poor substrate (30-33). MTIP of *P. aeruginosa* is the only reported MTIP with high specificity for MTI. MTA is not a substrate (less than the detection level of 10$^{-4}$ $k_{cat}$) but is a competitive inhibitor of MTI, with a K, value of 70 µM, three times greater than the of adenosine. Thus, MTA binds to the active site of the enzyme but is not catalytically competent.

Recombinant MTIP was expressed with a 14 amino acid extension at the N-terminus Incubation with TEV protease removed 13 of these, leaving one additional glycine at the N-terminus. This construct exhibited identical substrate specificity as the original recombinant protein. The crystal structure (see below) shows the N-terminal extension to be remote from the active site. Unchanged substrate specificity with or without the 13 amino acid extension supports activity of the native enzyme to be PaMTIP.

Crystal Structure of PaMTIP:Hypoxanthine.

The crystal structure of PaMTIP in complex with hypoxanthine was determined to 2.0 Å resolution with two homotrimers in the asymmetric unit. Residues 2 to 54 and 60 to 243 of each PaMTIP monomer are ordered in the electron density map. The N terminal His$_6$ tag and TEV protease site are disordered and distant from the active site. The PaMTIP monomer exhibits an α/β-fold consisting of a 7-stranded β-sheet and 5 α-helices. The active sites of PaMTIP are located near the interfaces formed between monomers in the trimer. Each trimeric PaMTIP forms three active sites. Although PaMTIP was co-crystallized with MTI and sulfate (5 mM) to mimic the Michaelis complex, the ligand-omitted difference Fourier map showed only the presence of hypoxanthine. Kinetic experiments demonstrated slow hydrolysis of MTI (3.8×10$^{-5}$ s$^{-1}$) to generate hypoxanthine and 5-methylthioribose. Crystallization attempts with apo-PaMTIP or with PaMTIP in complex with hypoxanthine and phosphate failed to yield crystals. In the crystal structure, hypoxanthine is wedged between the backbone of a 5-stranded β sheet and the side chains of Leu180 and Met190. Structure-based sequence alignment revealed that Met190 is conserved and Leu180 is replaced by Phe in human PNP and human MTAP (FIG. 2). Hypoxanthine N7 and O6 form hydrogen bond with the side chain of Asn223 in PaMTIP and N1 forms a hydrogen bond with the side chain of Asp 181.

Comparison with Other Purine N-Ribosylphosphorylases.

PaMTIP, PNPs and MTAPs have similar functions in the phosphorolysis of nucleosides, but show different substrate specificities. The structural architecture of PaMTIP is similar to the four MTAPs and seven trimeric PNPs in the Protein Data Bank (r.m.s.d is in the range of 0.8 to 1.2 Å for the monomers). Structure-based sequence alignments with PaMTIP show a 28-40% identity with the four MTAPs and 20-32% with the seven trimeric PNPs (FIG. 2). However, PaMTIP shows no significant similarity in amino acid sequence or quaternary structures with the hexameric PNPs including that from *Plasmodium* species. Because of this structural difference, *Plasmodium* PNPs are not included in the following analysis even though most *P. falciparum* PNPs also catalyze the phosphorolysis of MTI (34). The active sites of PaMTIP can be compared to those of PNP and MTAP by considering three distinct regions corresponding to the purine-, (methylthio)ribose- and phosphate-binding sites. The Glu201 and Asn243 (human PNP numbering) are conserved in the purine binding site of PaMTIP and PNPs (FIG. 2), and have an important role in 6-oxopurine specificity by hydrogen bonding to N1, O6 and N7 of the 6-oxopurine (35). Human PNP exhibits a 350,000-fold catalytic preference for 6-oxopurines compared to 6-aminopurines (36). The Asn243Asp mutant and Glu201Gln:Asn243Asp double mutant in human PNP is known to shift the substrate preference in favor of adenosine, a 6-aminopurine substrate (36). In contrast, MTAPs prefer 6-aminopurine (31). Human MTAP Ser178 (via a water molecule), Asp220 and Asp222 are conserved for the MTAPs, forming hydrogen bonds to N1, O6 and N7 of 6-aminopurine, respectively (37).

Human PNP is efficient for phosphorolysis of purine nucleosides with a 5'-hydroxyl group but not for purine nucleosides with a 5'-methylthio group. The conserved His257 and Phe159 (from the adjacent monomer) of human PNP are important in binding the 5'-hydroxyl group, whereas in MTAP and PaMTIP, a small hydrophobic amino acid corresponding to His257 and a His corresponding to Phe159 (human PNP numbering), provides space to accommodate the 5'-methylthio group. Consistent with these observations, the His257Gly mutant of human PNP binds 5'-methylthio-inhibitors tighter than the corresponding 5'-hydroxyl-inhibitors (38). Superposition of the liganded human MTAP and PNP structures reveals a 1 Å shift of phosphate toward the purine in human MTAP. Phosphate forms favorable hydrogen bonds with the 2'- and 3'-hydroxyl groups of (5'-methylthio) ribose, and thereby anchors (5'-methylthio)ribose to the active site. The spatial shift of the phosphate of human MTAP relative to that of human PNP places the 5'-methylthioribose closer to the purine binding site and this shift provides more room to accommodate the 5'-methylthio group in the active site of human MTAP. Structure-based sequence alignment shows that PaMTIP and MTAP share key residues in the phosphate and (methylthio)ribose-binding sites; however, PaMTIP has a purine binding site more similar to the PNPs, consistent with its preference for 6-oxypurines.

*P. aeruginosa* Catabolism [8-$^{14}$C]MTA.

Substrate specificity and structural data of PA3004 support a physiological function as MTIP. But this role requires production of MTI in *P. aeruginosa*; however, there is no previous report of MTI as a metabolite in *P. aeruginosa* and the published genetic approach supported MTAP activity (20). Catabolism of [8-$^{14}$C]MTA in lysates of *P. aeruginosa* was followed by analysis of hypoxanthine, adenine, MTI, and MTA. If MTA is first deaminated to MTI followed by PaMTIP action, the sequential conversion to [8-$^{14}$C]MTI and hypoxanthine would occur without adenine formation. After 10 min with lysate, 77% of the MTA was converted to MTI (52%) and hypoxanthine (25%) without significant formation of adenine (FIG. 3). As 98% of the total $^{14}$C-label was recovered, the results establish MTA conversion to MTI and hypoxanthine but not to adenine. At 25 min incubation, over 97% of the [8-$^{14}$C]MTA was recovered as MTI (45%) and hypoxanthine (53%). Continuous conversion of MTA→MTI→hypoxanthine without significant MTAP or MTAN activity is supported by these results, highlighting the requirement for an MTA deaminase to catalyze the conversion of MTA to MTI. There is no significant MTA phosphorylase or MTA nucleosidase activity in *P. aeruginosa* abstracts.

MTI Formation in *P. falciparum*.

A similar pathway of MTA catabolism is found in *Plasmodium* species (34). The adenosine deaminase of *P. falciparum* (PfADA) deaminates adenosine and MTA as substrates with similar $k_{cat}/K_m$ values (6.2×10$^4$ and 8.8×10$^4$, M$^{-1}$s$^{-1}$ respectively) (34). Its purine nucleoside phosphorylase (PJPNP) also degrades inosine and MTI to hypoxanthine with similar catalytic efficiency (3.6×10$^5$ and 9.4×10$^4$, M$^{-1}$s$^{-1}$ respectively) (33). Human PNP is a poor catalyst for MTI phosphorolysis and mammalian ADA does not deaminate MTA (34). The substrate specificities of the *P. falciparum* enzymes permit conversion of MTA to hypoxanthine via MTI. This process was reconstituted in vitro with purified PfADA and PfPNP (34). Metabolic and genomic studies have thus established that neither *P. aeruginosa* nor *P. falciparum* encode MTAN or MTAP activities.

MTI in Other Organisms.

Although MTI has been used as an MTA analogue, its function as a metabolite has been documented only in *Plasmodium* (30, 31, 39-42). Metabolism studies on *Saccharomyces cereviceae* suggested in vivo conversion of MTA to MTI, but the corresponding enzyme(s) and fate of MTI have not been determined (43). In humans, MTAP catalyzes the conversion of MTA to adenine and 5-methylthioribose-α-D-1-phosphate. And no other fate is known for MTA although it appears in human urine (44). Excess MTA added to cultured human cells is known to form some MTI through the reverse reaction of PNP using hypoxanthine and MTR-1-P, but it is not physiologically significant (45-46). The physiological fate of [8-$^{14}$C]MTI in *P. falciparum* has been established by following its incorporation into nucleic acids, where it was shown to be equivalent to inosine as a nucleic acid precursor (34).

The surprising discovery of MTIP catalytic activity in *Psuedomonas aeruginosa* led to a search of the genome data bases for other microbial species that could be treated in the same manner as *P. aeruginosa* (Table 4). Of particular interest are *Pseudomonas syringae* and *Xanthomonas campestris*, which are important plant pathogens. *P. syringae* produces ice nucleation-active (Ina) proteins that cause water to freeze at fairly high temperatures resulting in surface frost damage to plants (51). It has been estimated that frost accounts for approximately $1 billion in crop damage each year in the United States alone. *Xanthomonas campestris* causes a variety of plant diseases.

Picomolar Inhibitors of PaMTIP.

Figure 1:
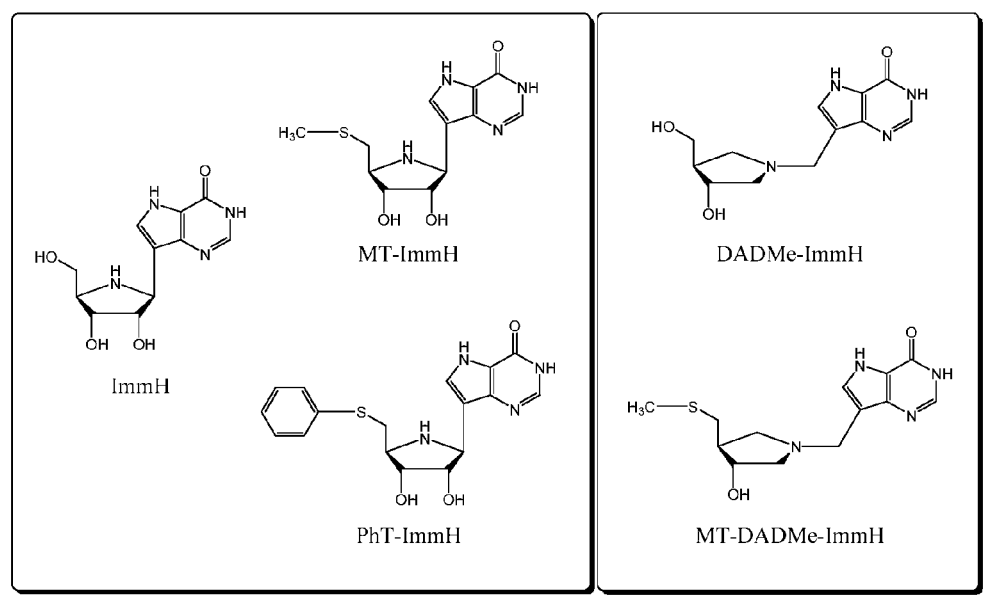
FIG. 1. Early and late transition-state mimics as inhibitors for PaMTIP and PfPNP.

Immucillins are transition-state analogues developed for N-ribosyl transferases that have ribocation character in their transition states (47) ImmH is a first generation Immucillin, representing early transition states exemplified by bovine PNP (FIG. 1). DADMe-ImmH is a second generation Immucillin and mimics the fully dissociated transition states of human and *P. falciparum* PNPs (48). 5'-Alkylthio- and arylthio-derivatives of two generations of Immucillins (MT-ImmH, PhT-ImmH, and MT-DADMe-ImmH) have been synthesized to target the transition-state features of PfPNP with MTI as the substrate (34). The inhibitors exhibited slow-onset inhibition of PaMTIP, suggesting a slow conversion of initial enzyme-inhibitor complex to a more stable conformation.

MT-ImmH inhibited PaMTIP with a $K_i^*$ value of 76 pM, binding 4-fold more tightly than MT-DADMe-ImmH, suggesting that the first generation Immucillins more closely resemble the transition state (Table 3). PhT-ImmH was the most tightly bound inhibitor with a $K_i^*$ value of 35 pM and demonstrating the importance of hydrophobic interactions at the 5'-position. Increasing the lipophilicity at the equivalent position in the second generation inhibitors by extending the alkyl chain length in going from MT-DADMe-ImmH to PrT-DADMe-ImmH similarly enhanced potency, in this instance by a factor of 4, confirming that both first and second generation Immucillins can provide highly effective inhibitors. Introduction of the 4'-C-hydroxy group (4'-HO-MT-DADMe-ImmH) provides a nanomolar inhibitor of PaMTIP. The acyclic Immucillin, MT-SerMe-ImmH, inhibited PaMTIP with a Ki* value of 96 pM, confirming that this class of Immucillin is also able to inhibit MTIP enzymes effectively. The MT-TrisMe-ImmH analogue, has a Ki value of 19 nM. The $K_{MTI}/K_i$ values were 34,000 for MT-ImmH, 7,600 for MT-DADMe-ImmH, and 74,000 for PhT-ImmH, emphasizing the potency of these transition state analogue inhibitors. Inhibitor specificity can be compared to that for PfPNP, which catalyzes the same reaction. Thus, MT-ImmH, PhT-ImmH, and MT-DADMe-ImmH bind more weakly to PfPNP with dissociation constants of 2.7 nM, 150 nM, and 0.9 nM, respectively (Table 3) (33, 49). Binding of the bulky, hydrophobic 5'-PhT-group is preferred by PaMTIP where $K_i^*=35$ pM. This inhibitor induces slow-onset, tight-binding inhibition. In contrast, the same inhibitor has $K_i=150$ nM with PfPNP, where it binds 4,300-fold more weakly and does not induce slow-onset inhibition. The $K_i^*$ values for certain MTIP inhibitors are indicated below.

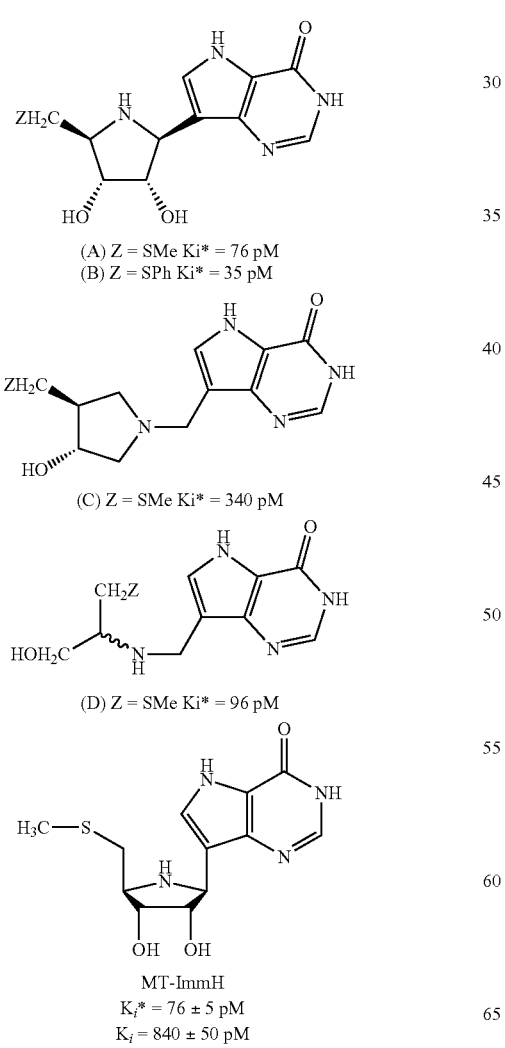

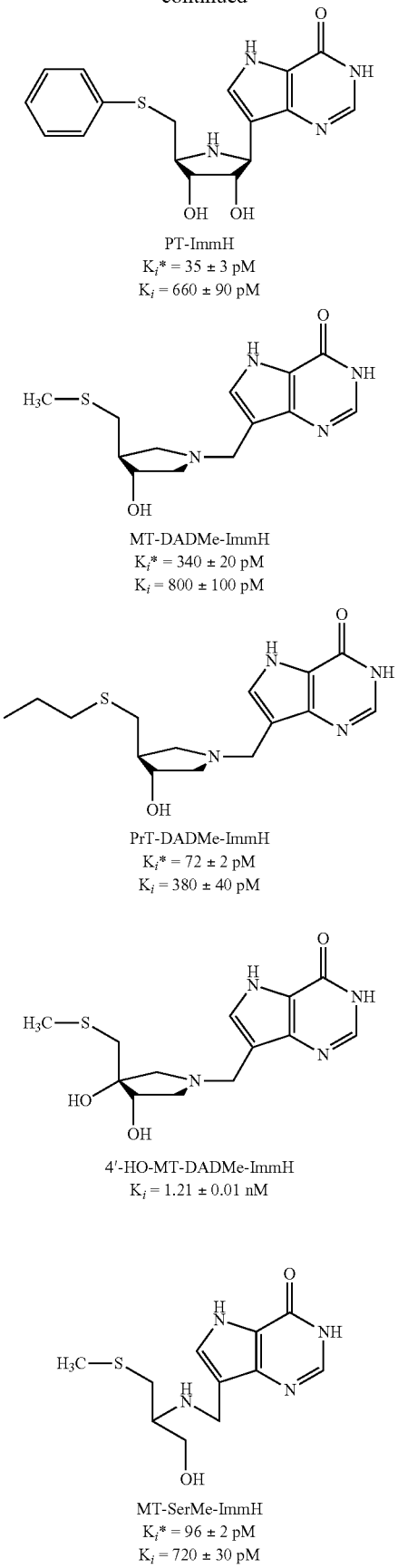

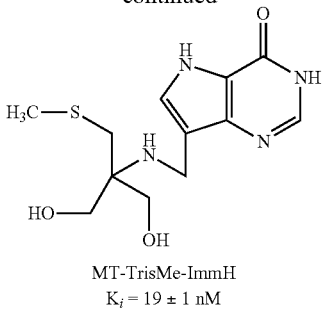

MT-TrisMe-ImmH
$K_i = 19 \pm 1$ nM

The Nature of the PaMTIP Transition State.

PfPNP has a fully-dissociated ribocation transition state with approximately 3 Å between the C1' ribocation and N9 and a similar separation between C1' and the attacking phosphate oxygen. Thus, it prefers to bind MT-DADMe-ImmH rather than MT-ImmH (50). PaMTIP shows the opposite pattern, consistent with an early, dissociative transition state.

Implications for Quorum Sensing.

Inhibition studies of PaMTIP have identified inhibitors with $K_i^*$ values in the picomolar range. These are candidates for blocking PaMTIP activities. In most bacteria, MTAN inhibition blocks quorum sensing, but the lack of MTAN in *P. aeruginosa* indicates that PaMTIP becomes an equivalent target. This study has revealed the pathway of MTA metabolism in *P. aeruginosa* and provided new tools to explore this unusual bacterial pathway.

TABLE 1

Data collection and refinement statistics.

| Data collection | |
| --- | --- |
| PDB | 3OZB |
| Space group | $P4_12_12$ |
| Cell dimension | |
| a, b, c (Å) | 99.5, 99.5, 334.9 |
| α, β, γ (°) | 90.0, 90.0, 90.0 |
| Resolutions (Å) | 20.0-2.8 |
|  | (2.9-2.8) |
| $R_{sym}$ (%) | 17.2 (95.5) |
| I/σI | 9.6 (1.9) |
| Completeness (%) | 100.0 (100.0) |
| Redundancy | 7.0 (7.2) |
| Refinement | |
| Resolution (Å) | 20.00-2.0 |
| No. reflections | 39915 |

TABLE 1-continued

Data collection and refinement statistics.

| | |
| --- | --- |
| $R_{work}/R_{free}$ (%) | 20.1/26.2 |
| B-factors (Å$^2$) | |
| Protein | |
| (main chain) | 39.9 |
| (side chain) | 40.9 |
| Water | 25.2 |
| Ligand | 46.0 |
| No. of Atoms | |
| Protein | 10800 |
| Water | 68 |
| Ligand | 60 |
| R.m.s deviations | |
| Bond lengths (Å) | 0.012 |
| Bond angles (°) | 1.46 |
| Ramanchran analysis | |
| allowed region | 99.3% |
| disallowed region | 0.7% |

Numbers in parentheses are for the highest-resolution shell. One crystal was used for each data set.

TABLE 2

Substrate specificity of PaMTIP.

| Substrate | $k_{cat}$ (s$^{-1}$) | $K_m$ (µM) | $k_{cat}/K_m$ (× 10$^3$ M$^{-1}$s$^{-1}$) |
| --- | --- | --- | --- |
| MTI | 4.8 ± 0.2 | 2.6 ± 0.4 | 1800 ± 300 |
| MTA[a] | N/A | 70 ± 20 | N/A |
| inosine | 0.57 ± 0.04 | 90 ± 20 | 6 ± 1$_{[300]}$[b] |
| adenosine | 0.0549 ± 0.0005 | 23 ± 1 | 2.4 ± 0.1$_{[750]}$[b] |

[a]MTA is not a substrate of PaMTIP. $K_i$ is used instead of $K_m$ for MTA.
[b]Numbers in [ ] are fold decreases of $K_{cat}/K_m$ in comparion with those of MTI.
[c]Values are ± S.E.

TABLE 3

Summary of Ki values for PaMTIP and PfPNP.

| | PaMTIP | | pfPNP[a] | |
| --- | --- | --- | --- | --- |
| Inhibitors | $K_i$ (pM) | $K_i^*$ (pM) | $K_i$ (pM) | $K_i^*$ (pM) |
| MT-ImmH | 840 ± 50 | 76 ± 5 | 22000 ± 3000 | 2700 ± 400 |
| PhT-ImmH | 660 ± 90 | 35 ± 3 | 150000 ± 8000 | ND |
| MT-DADMe-ImmH | 800 ± 100 | 340 ± 20 | 11000 ± 4000 | 900 ± 100 |

[a]Inhibition constants of PfPNP were from Lewandowicz et al. (49).
[b]Values are ± S.E.

TABLE 4

Microbial species searched for possible MTIP catalytic activity.

| Feature ID | Locus_Tag | Description | Species |
| --- | --- | --- | --- |
| 31909191 | VBIAciFer109666_1307 | MTAP | *Acidaminococcus fermentans* DSM 20731 |
| 24310952 | VBIAciSp85863_0249 | MTAP | *Acidaminococcus* sp. D21 |
| 20652065 | VBIAciFer29821_0353 | MTAP | *Acidithiobacillus ferrooxidans* ATCC 23270 |
| 20658606 | VBIAciFer6930_0524 | MTAP | *Acidithiobacillus ferrooxidans* ATCC 53993 |
| 20839765 | VBIAlcBor124741_1073 | MTAP | *Alcanivorax borkumensis* SK2 |
| 24415594 | VBIAlcSp134196_0029 | MTAP | *Alcanivorax* sp. DG881 |
| 24433023 | VBIAliAci16525_1025 | MTAP | *Alicyclobacillus acidocaldarius* LAA1 |
| 20846714 | VBIAliAci73240_1597 | MTAP | *Alicyclobacillus acidocaldarius* subsp. *acidocaldarius* DSM 446 |
| 20861899 | VBIAlkEhr114327_1328 | MTAP | *Alkalilimnicola ehrlichii* MLHE-1 |
| 31920755 | VBIAllVin64954_0500 | MTAP | *Allochromatium vinosum* DSM 180 |

TABLE 4-continued

Microbial species searched for possible MTIP catalytic activity.

| Feature ID | Locus_Tag | Description | Species |
|---|---|---|---|
| 20881494 | VBIAmmDeg104956_0971 | MTAP | *Ammonifex degensii* KC4 |
| 20958662 | VBIAquAeo85532_0465 | MTAP | *Aquifex aeolicus* VF5 |
| 20973491 | VBIAroAro98752_3663 | MTAP | *Aromatoleum aromaticum* EbN1 |
| 21012394 | VBIAzoSp26047_2034 | MTAP | *Azoarcus* sp. BH72 |
| 21029193 | VBIAzoVin72790_1379 | MTAP | *Azotobacter vinelandii* DJ |
| 27182875 | VBIBerMar44794_0658 | MTAP | *Bermanella marisrubri* |
| 30885632 | VBIBetPro60814_0744 | MTAP | beta proteobacterium KB13 |
| 21263520 | VBICanAcc132554_3989 | MTAP | *Candidatus Accumulibacter phosphatis* clade IIA str. UW-1 |
| 31968053 | VBICanDes92303_0674 | MTAP | *Candidatus Desulforudis* audaxviator MP104C |
| 30383843 | VBICarPac114674_0689 | MTAP | *Carboxydibrachium pacificum* DSM 12653 |
| 21276013 | VBICarHyd26463_1381 | MTAP | *Carboxydothermus hydrogenoformans* Z-2901 |
| 21442613 | VBIChrVio67196_3821 | MTAP | *Chromobacterium violaceum* ATCC 12472 |
| 27118095 | VBICloBac45081_0978 | MTAP | *Clostridiales bacterium* 1 7 47FAA |
| 29068547 | VBIConLit32816_3743 | MTAP | *Congregibacter litoralis* KT71 |
| 21474258 | VBICopPro72829_0673 | MTAP | *Coprothermobacter proteolyticus* DSM 5265 |
| 21602118 | VBIDecAro89105_1723 | MTAP | *Dechloromonas aromatica* RCB |
| 35334867 | VBIDefDes107323_0476 | MTAP | *Deferribacter desulfuricans* SSM1 |
| 21665529 | VBIDesHaf15223_3920 | MTAP | *Desulfitobacterium hafniense* DCB-2 |
| 21673960 | VBIDesHaf65307_2915 | MTAP | *Desulfitobacterium hafniense* Y51 |
| 21719077 | VBIDesAce42372_1190 | MTAP | *Desulfotomaculum acetoxidans* DSM 771 |
| 21730383 | VBIDesRed82656_2261 | MTAP | *Desulfotomaculum reducens* MI-1 |
| 26640796 | VBIDetAlk125442_2011 | MTAP | *Dethiobacter alkaliphilus* AHT 1 |
| 36975078 | VBIDiaInv115189_0190 | MTAP | *Dialister invisus* DSM 15470 |
| 21806196 | VBIDicThe33784_0766 | MTAP | *Dictyoglomus thermophilum* H-6-12 |
| 21810560 | VBIDicTur93964_0965 | MTAP | *Dictyoglomus turgidum* DSM 6724 |
| 25910268 | VBIGamPro11258_1251 | MTAP | gamma proteobacterium HTCC5015 |
| 36991798 | VBIGamPro33483_0733 | MTAP | gamma proteobacterium NOR5-3 |
| 22086164 | VBIHahChe29232_2456 | MTAP | *Hahella chejuensis* KCTC 2396 |
| 22096829 | VBIHalHal112047_1253 | MTAP | *Halorhodospira halophila* SL1 |
| 32206686 | VBIHalNea120669_1410 | MTAP | *Halothiobacillus neapolitanus* c2 |
| 22108421 | VBIHelMod36755_1971 | MTAP | *Heliobacterium modesticaldum* Ice1 |
| 22119229 | VBIHerAur93466_1152 | MENA | *Herpetosiphon aurantiacus* ATCC 23779 |
| 38514308 | VBIHydSp35543_1620 | MTAP | *Hydrogenivirga* sp. 128-5-R1-1 |
| 32212773 | VBIHydThe36152_1917 | MTAP | *Hydrogenobacter thermophilus* TK-6 |
| 36565664 | VBIHydSp5595_0540 | MTAP | *Hydrogenobaculum* sp. SN |
| 22134890 | VBIHydSp64203_0132 | MTAP | *Hydrogenobaculum* sp. Y04AAS1 |
| 27563531 | VBIJanSp77695_2689 | MTAP | *Janibacter* sp. HTCC2649 |
| 27466181 | VBILimSp111806_2854 | MTAP | *Limnobacter* sp. MED105 |
| 30256927 | VBILutNit9412_3599 | MTAP | *Lutiella nitroferrum* 2002 |
| 22430377 | VBIMagSp23654_1940 | MTAP | *Magnetococcus* sp. MC-1 |
| 25938712 | VBIMarGam125067_3745 | MTAP | marine gamma proteobacterium HTCC2143 |
| 30952185 | VBIMarGam120175_0624 | MTAP | marine gamma proteobacterium HTCC2148 |
| 22459174 | VBIMarAqu65105_2345 | MTAP | *Marinobacter aquaeolei* VT8 |
| 30999028 | VBIMarSp19762_0602 | MTAP | *Marinobacter* sp. ELB17 |
| 36495797 | VBIMegGen154667_0818 | MTAP | *Megasphaera genomo* sp. type 1 str. 28L |
| 32268663 | VBIMetFla97085_1558 | MTAP | *Methylobacillus flagellatus* KT |
| 22607820 | VBIMetCap22254_2017 | MTAP | *Methylococcus capsulatus* str. Bath |
| 26225373 | VBIMetThi34374_0895 | MTAP | *Methylophaga thiooxidans* DMS010 |
| 26231633 | VBIMetBac29390_0798 | MTAP | *Methylophilales bacterium* HTCC2181 |
| 22612561 | VBIMetMob89187_1188 | MTAP | *Methylotenera mobilis* JLW8 |
| 38199151 | VBIMetSp140979_1406 | MTAP | *Methylotenera* sp. 301 |
| 22617878 | VBIMetSp110381_1427 | MTAP | *Methylovorus* sp. SIP3-4 |
| 22638531 | VBIMooThe6753_0754 | MTAP | *Moorella thermoacetica* ATCC 39073 |
| 25483803 | VBINitMob112042_0928 | MTAP | *Nitrococcus mobilis* Nb-231 |
| 35395780 | VBINitHal115488_3010 | MTAP | *Nitrosococcus halophilus* Nc4 |
| 25494267 | VBINitOce87996_2021 | MTAP | *Nitrosococcus oceani* AFC27 |
| 22704664 | VBINitOce57959_0576 | MTAP | *Nitrosococcus oceani* ATCC 19707 |
| 22714750 | VBINitEur56163_1967 | MTAP | *Nitrosomonas europaea* ATCC 19718 |
| 22719073 | VBINitEut7577_1203 | MTAP | *Nitrosomonas eutropha* C91 |
| 25500690 | VBINitSp88817_2664 | MTAP | *Nitrosomonas* sp. AL212 |
| 22724352 | VBINitMul110821_0751 | MTAP | *Nitrosospira multiformis* ATCC 25196 |
| 23779746 | VBISymThe116959_0804 | MENA | *Symbiobacterium thermophilum* IAM 14863 |
| 22910709 | VBIPelThe8413_1946 | MTAP | *Pelotomaculum thermopropionicum* SI |
| 22915331 | VBIPerMar119911_0973 | MTAP | *Persephonella marina* EX-H1 |
| 25555006 | VBIPseAer126331_1953 | MTAP | *Pseudomonas aeruginosa* 2192 |
| 25567207 | VBIPseAer51129_2865 | MTAP | *Pseudomonas aeruginosa* C3719 |
| 19813767 | VBIPseAer113719_2130 | MTAP | *Pseudomonas aeruginosa* LESB58 |
| 19826092 | VBIPseAer80442_2070 | MTAP | *Pseudomonas aeruginosa* PA7 |
| 37796667 | VBIPseAer119691_1964 | MTAP | *Pseudomonas aeruginosa* PAb1 |
| 25582692 | VBIPseAer78937_3783 | MTAP | *Pseudomonas aeruginosa* PACS2 |
| 19840565 | VBIPseAer58763_3152 | MTAP | *Pseudomonas aeruginosa* PAO1 |
| 19850174 | VBIPseAer79785_2046 | MTAP | *Pseudomonas aeruginosa* UCBPP-PA14 |
| 19889839 | VBIPseFlu44242_3864 | MTAP | *Pseudomonas fluorescens* Pf0-1 |
| 19909669 | VBIPseMen131592_1613 | MTAP | *Pseudomonas mendocina* ymp |

TABLE 4-continued

Microbial species searched for possible MTIP catalytic activity.

| Feature ID | Locus_Tag | Description | Species |
|---|---|---|---|
| 37952625 | VBIPseSav158853_3365 | MTAP | *Pseudomonas savastanoi* pv. *savastanoi* NCPPB 3335 |
| 19963943 | VBIPseStu31643_1746 | MTAP | *Pseudomonas stutzeri* A1501 |
| 25590088 | VBIPseSyr138828_1392 | MTAP | *Pseudomonas syringae* pv. *aesculi* str. 2250 |
| 19975790 | VBIPseSyr78478_3367 | MTAP | *Pseudomonas syringae* pv. *phaseolicola* 1448A |
| 19987196 | VBIPseSyr42314_3354 | MTAP | *Pseudomonas syringae* pv. *syringae* B728a |
| 25607361 | VBIPseSyr86336_4594 | MTAP | *Pseudomonas syringae* pv. *syringae* FF5 |
| 25614561 | VBIPseSyr56650_2715 | MTAP | *Pseudomonas syringae* pv. *tabaci* ATCC 11528 |
| 19998439 | VBIPseSyr93040_3591 | MTAP | *Pseudomonas syringae* pv. *tomato* str. DC3000 |
| 25625381 | VBIPseSyr88081_2476 | MTAP | *Pseudomonas syringae* pv. *tomato* T1 |
| 28431114 | VBIReiBla99298_1448 | MTAP | *Reinekea blandensis* MED297 |
| 23402541 | VBISacDeg56404_1951 | MTAP | *Saccharophagus degradans* 2-40 |
| 35400680 | VBISidLit69165_1281 | MTAP | *Sideroxydans lithotrophicus* ES-1 |
| 23702535 | VBISteMal45202_3320 | MTAP | *Stenotrophomonas maltophilia* K279a |
| 23710908 | VBISteMal40512_2988 | MTAP | *Stenotrophomonas maltophilia* R551-3 |
| 30945052 | VBISteSp70125_0969 | MTAP | *Stenotrophomonas* sp. SKA14 |
| 23764404 | VBISulAzo123226_1591 | MTAP | *Sulfurihydrogenibium azorense* Az-Fu1 |
| 23767117 | VBISulSp94719_1189 | MTAP | *Sulfurihydrogenibium* sp. YO3AOP1 |
| 28316110 | VBISulYel28410_0490 | MTAP | *Sulfurihydrogenibium yellowstonense* SS-5 |
| 23781549 | VBISymThe116959_1695 | MTAP | *Symbiobacterium thermophilum* IAM 14863 |
| 23856307 | VBISynWol51738_0821 | MTAP | *Syntrophomonas wolfei* subsp. *wolfei* str. Goettingen |
| 38269016 | VBISynLip21176_1328 | MTAP | *Syntrophothermus lipocalidus* DSM 12680 |
| 23865162 | VBISynAci70500_2363 | MTAP | *Syntrophus aciditrophicus* SB |
| 23880636 | VBIThaSp83776_2179 | MTAP | *Thauera* sp. MZ1T |
| 38275831 | VBITheSp141296_2211 | MTAP | *Thermincola* sp. JR |
| 29924698 | VBITheBro57020_1537 | MTAP | *Thermoanaerobacter brockii* subsp. *finnii* Ako-1 |
| 30825907 | VBITheEth125011_1168 | MTAP | *Thermoanaerobacter ethanolicus* CCSD1 |
| 32497914 | VBITheIta22270_1468 | MTAP | *Thermoanaerobacter italicus* Ab9 |
| 38281044 | VBITheMat18_1480 | MTAP | *Thermoanaerobacter mathranii* subsp. *mathranii* str. A3 |
| 23886420 | VBIThePse6203_0923 | MTAP | *Thermoanaerobacter pseudethanolicus* ATCC 33223 |
| 31262795 | VBITheSp37765_1746 | MTAP | *Thermoanaerobacter* sp. X513 |
| 23893440 | VBITheSp86957_1944 | MTAP | *Thermoanaerobacter* sp. X514 |
| 30832536 | VBITheSp21349_1908 | MTAP | *Thermoanaerobacter* sp. X561 |
| 23897876 | VBITheTen82880_1587 | MTAP | *Thermoanaerobacter tengcongensis* MB4 |
| 32508736 | VBITheAlb52854_1221 | MTAP | *Thermocrinis albus* DSM 14484 |
| 23908977 | VBITheYel104483_0962 | MTAP | *Thermodesulfovibrio yellowstonii* DSM 11347 |
| 30839490 | VBITheCar126673_2743 | MTAP | *Thermosinus carboxydivorans* Nor1 |
| 23963030 | VBIThiSp19295_1753 | MTAP | *Thioalkalivibrio* sp. HL-EbGR7 |
| 32526054 | VBIThiSp13812_1233 | MTAP | *Thioalkalivibrio* sp. K90mix |
| 23967725 | VBIThiDen82923_0777 | MTAP | *Thiobacillus denitrificans* ATCC 25259 |
| 29650470 | VBIVeiDis1254_0157 | MTAP | *Veillonella dispar* ATCC 17748 |
| 36458212 | VBIVeiPar156829_1474 | MTAP | *Veillonella parvula* ATCC 17745 |
| 32531194 | VBIVeiPar80537_0927 | MTAP | *Veillonella parvula* DSM 2008 |
| 36275462 | VBIVeiSp18830_0337 | MTAP | *Veillonella* sp. 3 1 44 |
| 36279337 | VBIVeiSp6271_0334 | MTAP | *Veillonella* sp. 6 1 27 |
| 32547531 | VBIXanAlb89132_2491 | MTAP | *Xanthomonas albilineans* |
| 24054663 | VBIXanAxo33670_1412 | MTAP | *Xanthomonas axonopodis* pv. *citri* str. 306 |
| 24067511 | VBIXanCam24967_3134 | MTAP | *Xanthomonas campestris* pv. *campestris* str. 8004 |
| 24073319 | VBIXanCam115730_1376 | MTAP | *Xanthomonas campestris* pv. *campestris* str. ATCC 33913 |
| 24085960 | VBIXanCam108527_3058 | MTAP | *Xanthomonas campestris* pv. *campestris* str. B100 |
| 25699756 | VBIXanCam81519_3238 | MTAP | *Xanthomonas campestris* pv. *musacearum* NCPPB4381 |
| 26313008 | VBIXanCam29727_1092 | MTAP | *Xanthomonas campestris* pv. *vasculorum* NCPPB702 |
| 24092240 | VBIXanCam71633_1615 | MTAP | *Xanthomonas campestris* pv. *vesicatoria* str. 85-10 |
| 35684919 | VBIXanFus21887_3741 | MTAP | *Xanthomonas fuscans* subsp. *aurantifolii* str. ICPB 10535 |
| 35674697 | VBIXanFus92710_3232 | MTAP | *Xanthomonas fuscans* subsp. *aurantifolii* str. ICPB 11122 |
| 24102870 | VBIXanOry111333_2072 | MTAP | *Xanthomonas oryzae* pv. *oryzae* KACC10331 |
| 24113099 | VBIXanOry49434_1979 | MTAP | *Xanthomonas oryzae* pv. *oryzae* MAFF 311018 |
| 24125601 | VBIXanOry73153_3157 | MTAP | *Xanthomonas oryzae* pv. *oryzae* PXO99A |
| 26326018 | VBIXanOry69950_3062 | MTAP | *Xanthomonas oryzae* pv. *oryzicola* BLS256 |
| 24134970 | VBIXylFas578_2504 | MTAP | *Xylella fastidiosa* 9a5c |
| 26340625 | VBIXylFas50652_2177 | MTAP | *Xylella fastidiosa* Dixon |
| 24139674 | VBIXylFas124301_1785 | MTAP | *Xylella fastidiosa* M12 |
| 24145269 | VBIXylFas85937_1803 | MTAP | *Xylella fastidiosa* M23 |
| 26353973 | VBIXylFas52623_5708 | MTAP | *Xylella fastidiosa* subsp. *sandyi* Ann-1 |

TABLE 4-continued

Microbial species searched for possible MTIP catalytic activity.

| Feature ID | Locus_Tag | Description | Species |
|---|---|---|---|
| 26344082 | VBIXylFas52623_0929 | MTAP | *Xylella fastidiosa* subsp. *sandyi* Ann-1 |
| 24150927 | VBIXylFas71109_1769 | MTAP | *Xylella fastidiosa* Temecula1 |

MTAP = 5'-methylthioadenosine phosphorylase;
MENA = Menaquinone via futalosine step 4, possible alternative.

Description of Chemical Compounds

In one embodiment, as described in part in U.S. Pat. No. 5,985,848 and in PCT International Patent Application Publication No. WO 99/19338, the contents of which are herein incorporated by reference, the MTIP inhibitor comprises a compound having formula (I):

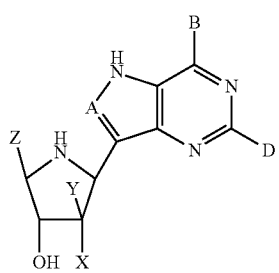

(I)

wherein A is CH or N; B is OH; D is chosen from H, OH, $NH_2$, or $SCH_3$; and X and Y are independently selected from H, OH or halogen, except that when one of X and Y is hydroxy or halogen, the other is hydrogen; Z is selected from $CH_2SQ$, $CH_2OQ$ or Q, where Q is an optionally substituted alkyl, aralkyl, aralkenyl or aryl group, each of which is optionally substituted with one or more substituents selected from hydroxy, halogen, methoxy, amino, carboxy, or straight- or branched-chain $C_1$-$C_6$ alkyl; provided that Z is not $CH_2OH$; or a tautomer thereof; or a pharmaceutically acceptable salt thereof; or an ester thereof.

Methods to make compounds of formula (I) can be found in WO 99/19338 and in U.S. Pat. No. 5,985,848.

Methods to make compounds of formula (I) in which X=OH and Y=H can be found in PCT International Patent Application Publication No. WO 00/061783 and in U.S. Pat. No. 6,693,193, the contents of which are herein incorporated by reference.

1,4-Dideoxy-1,4-imino-2,3-O-isopropylidene-D-ribitol can be converted into compounds of formula (I) below. Compounds of formula (I) can be converted into compounds of formula (I) by the methods provided in WO 00/061783 and in U.S. Pat. No. 6,693,193.

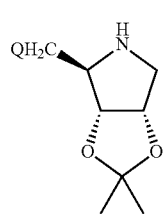

(i)

The compound of Formula (II) below can be converted into compounds of formula (I) where Z=Q by oxidation at C-5', Witting reaction with the resulting aldehyde, optionally hydrogenating the double bond so formed, then removing the protecting groups by acid hydrolysis or a combination of acid hydrogenolysis and acid hydrolysis. Compound (II) can be prepared by selectively removing the 5'-O-tert-butyldimethylsilyl protecting group of compound 40 in Evans et al, *J. Org. Chem.*, 66 (2001) 5723, e.g. by the use of tetrabutylammonium fluoride.

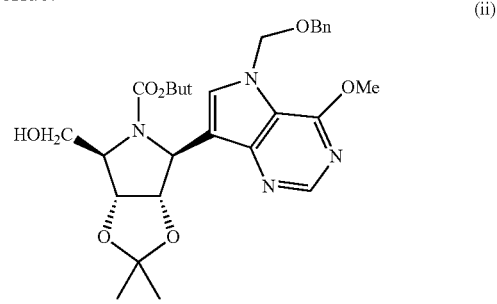

(ii)

A method to make the compound

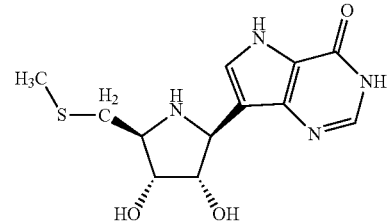 [SMILES: CSC[C@H]1N[C@@H](c2c[nH]c3c(=O)[nH]cnc23)[C@H](O)[C@@H]1O]

can be found in WO 99/19338 and in U.S. Pat. No. 5,985,848, where it was referred to as (1S)-1,4-dideoxy-1-C-(4-hydroxypyrrolo[3,2-d]pyrimidin-7-yl)-1,4-imino-5-methylthio-D-ribitol. Subsequently, the compound was reported as an inhibitor of the PNP of *Plasmodium falciparum* and its method of synthesis was described (W. Shi et al, *J. Biol. Chem.*, 279 (2004) 18103) (33).

The compound

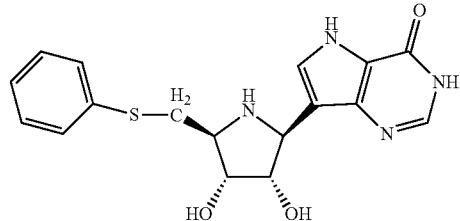 [SMILES: O=c1[nH]cnc2c([C@@H]3N[C@H](CSc4ccccc4)[C@@H](O)[C@H]3O)c[nH]c12]

is reported in connection with its inhibition of the human and *Plasmodium falciparum* PNP and a method of synthesis was described (A. Lewandowicz et al, *J. Biol. Chem.*, 280 (2005) 30320) (49).

The compound

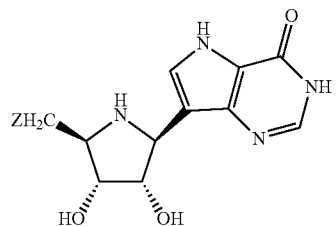

where Z=His disclosed in A. Lewandowicz et al, J. Biol. Chem., 280 (2005) 30320 (49) as an inhibitor of PNP.

In another embodiment, as described in U.S. Pat. No. 7,553,839 and in PCT International Patent Application Publication No. WO 04/018496, and in WO 2007/069924 the contents of which are herein incorporated by reference, the MTIP inhibitor comprises a compound having formula (III) or (IIIa):

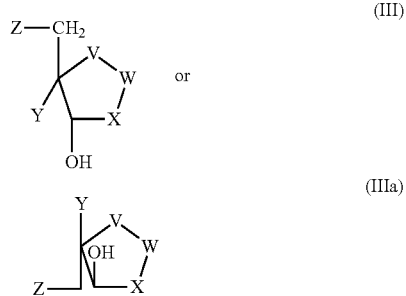

wherein V is $CH_2$ and W is $NR^1$; X is $CH_2$; Y is selected from hydrogen, halogen and hydroxyl; Z is selected from hydrogen, halogen, SQ, OQ and Q, where Q is an optionally substituted alkyl, aralkyl or aryl group, each of which is optionally substituted with one or more substituents selected from hydroxy, halogen, methoxy, amino, carboxy, or straight- or branched-chain $C_1$-$C_6$ alkyl; $R^1$ is a radical of the formula (IV)

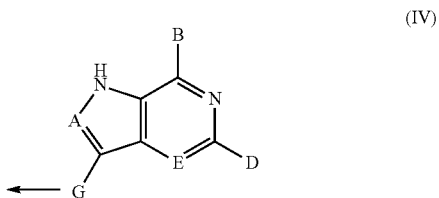

A is selected from N, CH and CR, where R is selected from halogen or optionally substituted alkyl, aralkyl or aryl group, each of which is optionally substituted with one or more substituents selected from hydroxy, halogen, methoxy, amino, carboxy, or straight- or branched-chain $C_1$-$C_6$ alkyl; B is OH; D is selected from OH, $NH_2$, $SCH_3$ and hydrogen; E is N; G is $CH_2$; or a tautomer thereof or a pharmaceutically acceptable salt thereof; or an ester thereof.

Methods to make compounds of formula (III) and (IIIa) are provided in U.S. Pat. No. 7,553,839 and in WO 04/018496, and in WO 2007/069924, and also in U.S. Pat. No. 7,655,795 and WO 2004/069856, the contents of all of which are herein incorporated by reference.

The compound

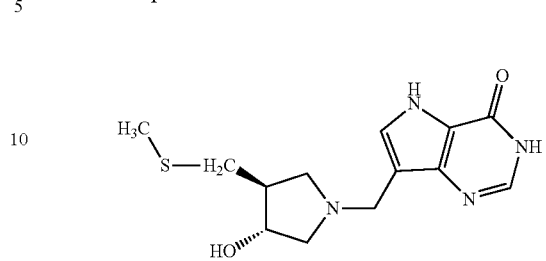

is disclosed in WO 2004/018496 and in U.S. Pat. No. 7,553,839 as "(3R,4S)-1-[(9-deazahypoxanthin-9-yl)methyl]-3-hydroxy-4-(methylthiomethyl)pyrrolidine", exemplified as compound 37 (Example 29) and shown to have PNP inhibitory properties. It is disclosed as (3R,4S)-1-[(9-deazahypoxanthin-9-yl)methyl]-3-hydroxy-4-(methylthiomethyl)-pyrrolidine in WO 2004/069856 and in U.S. Pat. No. 7,655,795 as a compound that can be prepared by the process disclosed and claimed therein. The compound is also reported as an inhibitor of human and *Plasmodium falciparum* PNP and a method of synthesis is described (A. Lewandowicz et al, *J. Biol. Chem.*, 280 (2005) 30320) (49).

The compound

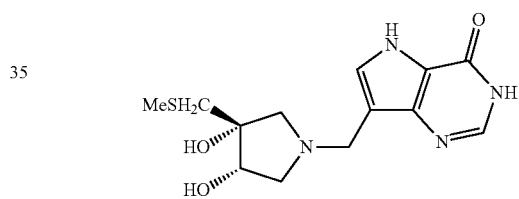

is disclosed in in WO 2004/018496 and in U.S. Pat. No. 7,553,839, as "(3S,4R)-1-[(9-deazahypoxanthin-9-yl)methyl]-3,4-dihydroxy-4-methylthiomethylpyrrolidine", exemplified as compound 33 (Example 28) and shown to have PNP inhibitory properties. This is an example where Y=OH. It is also reported in connection with its inhibition of the human and *Plasmodium falciparum* PNP and a method of synthesis is described (A. Lewandowicz et al, *J. Biol. Chem.*, 280 (2005) 30320) (49).

The compound

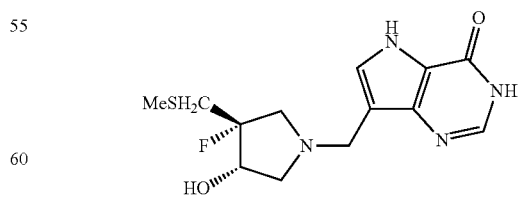

as a racemic mixture with its enantiomer is reported in connection with its inhibition of the human and mutated human PNP and a method of synthesis is described (A. Murkin et al, *Bioorg. Med. Chem. Lett.*, 18 (2008) 5900.

The compound

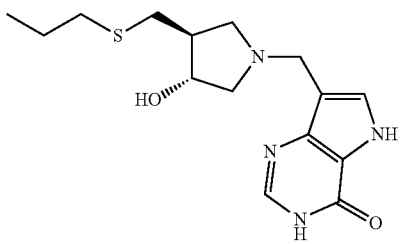 [SMILES: CCCSC[C@H]1CN(Cc2c[nH]c3c(=O)[nH]cnc23)C[C@@H]1O]

is disclosed in U.S. Pat. No. 7,655,795 and WO 2004/069856 as "(3R,4S)-1-[(9-deazahypoxanthin-9-yl]-3-hydroxy-4-(propylthiomethyl)-pyrrolidine" and exemplified as compound 24 in Example 1.20 as a compound that can be prepared by the process disclosed and claimed therein. It is reported in connection with its inhibition of human and *Plasmodium falciparum* PNP and a method of synthesis was described (A. Lewandowicz et al, *J. Biol. Chem.*, 280 (2005) 30320) (49).

The compound:

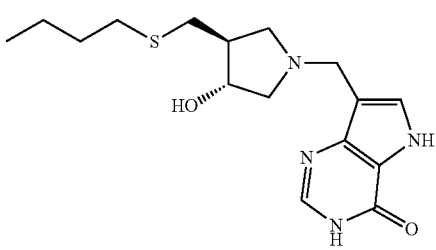 [SMILES: CCCCSC[C@H]1CN(Cc2c[nH]c3c(=O)[nH]cnc23)C[C@@H]1O]

is disclosed in U.S. Pat. No. 7,655,795 and WO 2004/069856 as "(3R,4S)-4-(butylthiomethyl)-1-[(9-deazahypoxanthin-9-yl)methyl]-3-hydroxy-pyrrolidine", and exemplified as compound 25 in Example 1.21.

The compound:

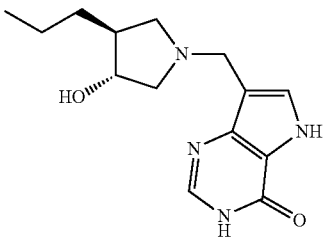 [SMILES: CCC[C@H]1CN(Cc2c[nH]c3c(=O)[nH]cnc23)C[C@@H]1O]

is disclosed as "(3R,4S)-1-[(9-Deazahypoxanthin-9-yl)methyl]-3-hydroxy-4-propyl-pyrrolidine", compound 28 in Example 1.24 of in U.S. Pat. No. 7,655,795 and WO 2004/069856.

This compound can also be prepared according to the following procedure:

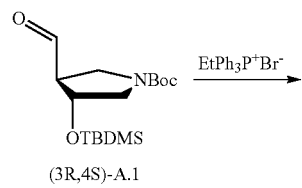

(3R,4S)-A.1

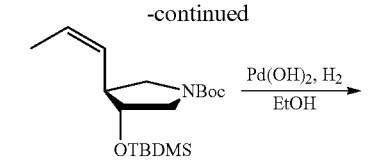

(3R,4S)-A.2

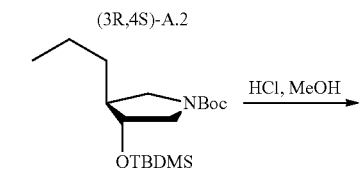

(3R,4S)-A.3

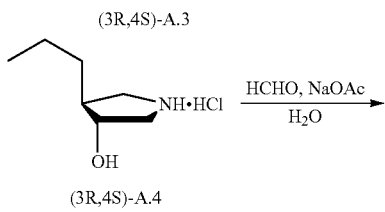

(3R,4S)-A.4

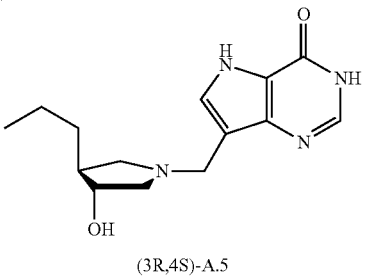

(3R,4S)-A.5

(3R,4S)-tert-Butyl 3-(tert-butyldimethylsilyloxy)-4-formylpyrrolidine-1-carboxylate (A.1)

This compound is prepared as described in Longshaw, Alistair I.; Adanitsch, Florian; Gutierrez, Jemy A.; Evans, Gary B.; Tyler, Peter C.; Schramm, Vern L. Design and Synthesis of Potent "Sulfur-Free" Transition State Analogue Inhibitors of 5'-Methylthioadenosine Nucleosidase and 5'-Methylthioadenosine Phosphorylase. Journal of Medicinal Chemistry (2010), 53(18), 6730-6746.

(3R,4S)-tert-Butyl 3-(tert-butyldimethylsilyloxy)-4-(propen-2-yl)pyrrolidine-1-carboxylate (A.2)

n-Butyllithium (1.95 mL, 2.7 mmol, 1.4 M solution in hexanes) was added drop-wise to a stirred suspension of ethyltriphenylphosphonium bromide (2.03 g, 5.5 mmol) in THF (10 mL) at 0° C. After 30 min a solution of A.1 (977 mg, 3.0 mmol) in THF (10 mL) was added. The reaction mixture was stirred overnight and allowed to warm to room temperature. The reaction was quenched with water (30 mL) and extracted with ethyl acetate (100 mL). The combined organic phases were washed with saturated aqueous sodium hydrogen carbonate solution (50 mL) and brine (50 mL) and then dried (MgSO$_4$), filtered and concentrated in vacuo. Flash chromatography of the residue (1:9, EtOAc:Petrol) afforded A.2 as a colorless oil (250 mg, 40%). $^1$H NMR (500 MHz, CDCl$_3$): δ=5.59 (m, 1H), 5.17 (m, 2H), 3.95 (m, 1H), 3.66-3.48 (m, 2H), 3.17-2.32 (m, 2H), 1.67 (d, J=6.6 Hz, 2H), 1.46 (s, 9H), 0.87 (s, 9H) and 0.04 ppm (s, 6H).

3-(tert-butyldimethylsilyloxy)-4-propylpyrrolidine-1-carboxylate (A.3)

Perlman's catalyst (75 mg, 0.9 mmol, 20 wt % on carbon) was added to a solution of A.2 (221 mg, 0.65 mmol) in ethanol (5 mL) under an argon atmosphere. The reaction mixture was placed under a hydrogen atmosphere and stirred overnight and then filtered through Celite® and concentrated under reduced pressure to afford the title compound A.3 (0.220 mg, 99%). NMR confirmed that no olefinic protons remained and that no further purification was necessary.

(3R,4S)-4-Propyl-3-hydroxypyrrolidine (A.4)

Concentrated HCl (1 ml, 12 mmol) was added to a solution of A.3 (0.22 g, 0.62 mmol) in methanol (5 ml) and concentrated in vacuo. The resulting residue was dissolved in additional concentrated HCl (1 ml, 12 mmol) and concentrated in vacuo. The residue was dissolved in water (10 ml) and washed with CHCl$_3$ (2×20 ml) and the water layer concentrated in vacuo to afford A.4. $^{13}$C NMR (125 MHz, D$_2$O): δ=73.4, 51.1, 48.9, 45.0, 32.6, 20.2 and 13.3 ppm.

(3R,4S)-1-[(9-Deazahypoxanthin-9-yl)methyl]-4-propyl-3-hydroxypyrrolidine (A.5)

9-Deazahypoxanthine (0.147 g, 1.09 mmol) was added to a solution of A.4 (0.090 g, 0.54 mmol) and sodium acetate (0.089 g, 1.09 mmol) in water (2 ml). After 5 min aqueous formaldehyde (0.084 ml, 1.087 mmol) was added and the resulting suspension warmed to 95° C. bath temperature and the resulting mixture stirred overnight. The reaction mixture was then cooled to room temperature and absorbed onto silica gel. The resulting residue was purified by chromatography eluting with 25% 7N NH3 in MeOH:CHCl$_3$ to afford A.5 (90 mg, 60%) as a white solid. $^{13}$C NMR (125 MHz, D$_2$O): δ=163.5, 151.7, 145.4, 127.7, 118.8, 109.7, 76.2, 59.9, 57.1, 47.3, 46.1, 34.6, 20.6, and 13.4 ppm.

The compound:

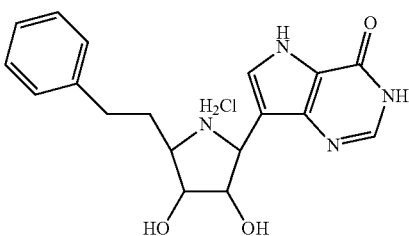

is prepared according to the following procedure:

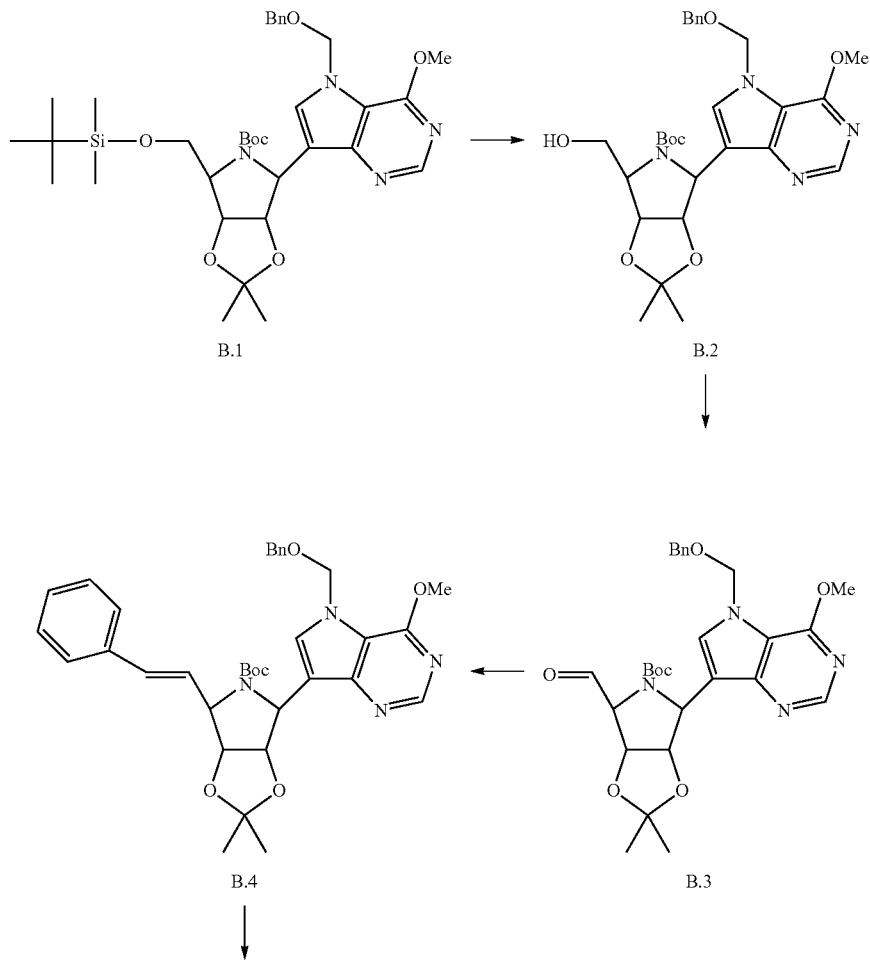

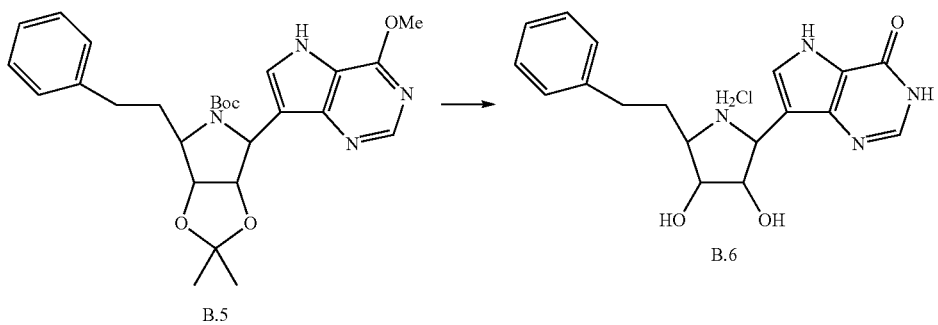

To a solution of B.1 (1.3 g, 1.985 mmol) in THF (30 mL) was added acetic acid (0.114 ml, 1.985 mmol) and then TBAF (tetrabutyl ammonium fluoride 1M THF) (1.730 ml, 5.96 mmol). The solution was stirred at ~50-60° C. for 16 h. After evaporation, toluene was added and the solution was washed water, dried (MgSO$_4$) and concentrated. Chromatography (25-50% EtOAc/Hex) gave B.2 as a foam (1.0 g, 1.85 mmol, 93%).

To a stirred solution of B.2 (100 mg, 185 μmol) in dry DCM (3 mL) was added Dess-Martin periodinane (157 mg, 370 μmol). After 16 h the mixture was concentrated to dryness. Chromatography (20-60% EtOAc/Hex) gave B.3 as a syrupy product (58 mg, 108 μmol, 58%).

A 1M solution of lithium bis(trimethylsilyl)amide in THF (204 μl, 204 μmol) was added to a suspension of benzyl triphenylphosphonium bromide (97 mg, 225 μmol) in dry THF (3 mL) at –75° C. and then the mixture was allowed to warm to 0° C. After 30 mins at 0° C. a solution of B.3 (55 mg, 102 μmol) in THF (1 mL) was added and then the mixture was stirred at RT. After 30 mins chloroform was added and the mixture was washed with water, dried (MgSO$_4$) and concentrated. Chromatography of the residue (15-40% EtOAc/Hex) gave B.4 as a syrup (59 mg 96 μmol, 94%).

To a solution of B.4 (55 mg, 90 μmol) in EtOH and some NH3/MeOH was added 10% Pd/C and the mixture was stirred under H2. After 2 days the mixture was filtered and the filtrate concentrated. Chromatography of the residue (20-60% EtOAc/Hex) gave B.5 as a syrup (25 mg, 50 μmol, 56%).

A solution of B.5 (25 mg, 50.5 μmol) in MeOH (4 mL) and conc aq HCl (4 mL) was heated under reflux for 3 h and then concentrated to dryness. The residue in water was lyophilized to a white powder of B.6 (18 mg, 48 μmol, 94%). $^1$H nmr (d$^4$MeOH with a little DCl/D$_2$O) δ 9.1 (1H, s), 8.1 (1H, s), 7.31 (4H, m), 7.20 (1H, m), 4.96 (1H, d), 4.73 (1H, dd), 4.30 (1H, t), 3.68 (1H, m), 2.84 (2H, m), 2.27 (2H, m). $^{13}$C nmr δ 152.5, 146.7, 141.7, 132.5, 131.9, 129.7, 127.4, 119.8, 106.5, 74.1, 73.8, 66.6, 57.3, 34.0, 33.5. HRMS calc for MH$^+$ C$_{18}$H$_{21}$N$_4$O$_3$ 341.1614. found 341.1618.

In another embodiment, as described in PCT International Patent Application Publication No. WO 2008/030119, the contents of which are herein incorporated by reference, the MTIP inhibitor comprises a compound having formula (VI):

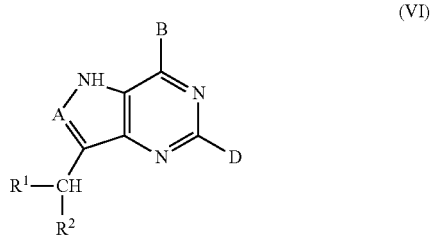

(VI)

wherein R$^1$ is H or NR$^3$R$^4$; R$^2$ is H or an alkyl, alkenyl, alkynyl, aralkyl, aralkenyl, aralkynyl, or aryl group, each of which is optionally substituted with one or more hydroxy, alkoxy, thiol, alkylthio, arylthio, aralkylthio, halogen, carboxylic acid, carboxylate alkyl ester, nitro, or NR$^3$R$^4$ groups, where each alkylthio, arylthio and aralkylthio group is optionally substituted with one or more alkyl, halogen, amino, hydroxy, or alkoxy groups; provided that when R$^1$ is H, R$^2$ is an alkyl, alkenyl, alkynyl, aralkyl, aralkenyl, aralkynyl, or aryl group which is substituted with at least one NR$^3$R$^4$ group, and optionally substituted with one or more hydroxy, alkoxy, thiol, alkylthio, arylthio, aralkylthio, halogen, carboxylic acid, carboxylate alkyl ester or nitro group; R$^3$ and R$^4$, independently of each other, are H or an alkyl, alkenyl, alkynyl, aralkyl, aralkenyl, aralkynyl, or aryl group, each of which is optionally substituted with one or more hydroxy, alkoxy, thiol, alkylthio, arylthio, aralkylthio, halogen, carboxylic acid, carboxylate alkyl ester, nitro, or NR$^3$R$^4$ groups, where each alkylthio, arylthio and aralkylthio group is optionally substituted with one or more alkyl, halogen, amino, hydroxy, or alkoxy groups; A is N or CH; B is OH; and D is H, OH, NH$_2$, or SCH$_3$; or a tautomer thereof, or a pharmaceutically acceptable salt thereof, or an ester prodrug form thereof.

Methods to make compounds of formula (VI) are provided in WO 08030119. Certain of the amino-alcohols required for use in the synthesis of the compounds of formula (VI) can be obtained through reduction of amino-acids to the corresponding amino-alcohols.

In another embodiment, the MTIP inhibitor comprises a compound having formula (VII):

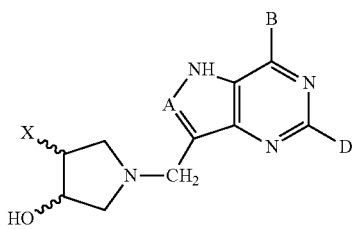

(VII)

wherein X is an alkyl, cycloalkyl, aralkyl, aralkenyl, alkenyl, alkynyl or aryl group, each of which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole and $NR^2R^3$ group, where each alkylthio, arylthio and aralkylthio group is optionally substituted with one or more alkyl, halogen, amino, hydroxy, or alkoxy groups; or X is $SR^1$; or X is $NR^2R^3$; $R^1$, $R^2$ and $R^3$ are independently selected from the group consisting of alkyl, alkenyl, alkynyl, aralkyl or aryl, each of which is optionally substituted with one or more substituents selected from the group consisting of hydroxy, alkoxy, thiol, alkylthio, arylthio, aralkylthio, halogen, carboxylic acid, carboxylate alkyl ester, nitro, cyano and $NR^2R^3$ group, where each alkylthio, arylthio and aralkylthio group is optionally substituted with one or more alkyl, halogen, amino, hydroxy, or alkoxy groups; A is N or CH; B is OH; D is H, OH, $NH_2$, or $SCH_3$; provided that X is not $CH_2Z$, where Z is selected from OH, hydrogen, halogen, $SQ^1$, $OQ^2$ and $Q^3$, where $Q^1$ is an optionally substituted alkyl, aralkyl or aryl group, $Q^2$ is an optionally substituted alkyl group and $Q^3$ is an optionally substituted alkyl group; or a tautomer thereof, or a pharmaceutically acceptable salt thereof, or an ester prodrug form thereof.

Methods to make compounds of formula (VII) are provided in U.S. Pat. No. 7,553,839 and in WO 04/018496, the contents of all of which are herein incorporated by reference, where a 3-hydroxypyrrolidine is coupled to 9-deaza9-formylpurine derivative by reductive amination, and in U.S. Pat. No. 7,655,795 and WO 2004/069856, the contents of all of which are herein incorporated by reference, where a 3-hydroxypyrrolidine is coupled to 9-deazapurine and formaldehyde in a Mannich reaction. Suitable 3-hydroxypyrrolidines may be prepared by methods detailed in PCT/NZ2010/000148 and in A. Longshaw et al., J. Med. Chem., 53 (2010) 6730.

REFERENCES

1. Hardalo, C., and Edberg, S. C. (1997) Pseudomonas aeruginosa: assessment of risk from drinking water, Crit. Rev. Microbiol. 23, 47-75.
2. Bodey, G. P., Bolivar, R., Fainstein, V., and Jadeja, L. (1983) Infections caused by Pseudomonas aeruginosa, Rev. Infect. Dis. 5, 279-313.
3. Van Delden, C., and Iglewski, B. H. (1998) Cell-to-cell signaling and Pseudomonas aeruginosa infections, Emerg Infect Dis 4, 551-560.
4. Strateva, T., and Yordanov, D. (2009) Pseudomonas aeruginosa—a phenomenon of bacterial resistance, J Med Microbiol 58, 1133-1148.
5. Lyczak, J. B., Cannon, C. L., and Pier, G. B. (2002) Lung infections associated with cystic fibrosis, Clin Microbiol Rev 15, 194-222.
6. Govan, J. R., and Deretic, V. (1996) Microbial pathogenesis in cystic fibrosis: mucoid Pseudomonas aeruginosa and Burkholderia cepacia, Microbiol Rev 60, 539-574.
7. Wagner, V. E., Bushnell, D., Passador, L., Brooks, A. I., and Iglewski, B. H. (2003) Microarray analysis of Pseudomonas aeruginosa quorum-sensing regulons: effects of growth phase and environment, J Bacteriol 185, 2080-2095.
8. Schuster, M., Lostroh, C. P., Ogi, T., and Greenberg, E. P. (2003) Identification, timing, and signal specificity of Pseudomonas aeruginosa quorum-controlled genes: a transcriptome analysis, J Bacteriol 185, 2066-2079.
9. Hentzer, M., Wu, H., Andersen, J. B., Riedel, K., Rasmussen, T. B., Bagge, N., Kumar, N., Schembri, M. A., Song, Z., Kristoffersen, P., Manefield, M., Costerton, J. W., Molin, S., Eberl, L., Steinberg, P., Kjelleberg, S., Hoiby, N., and Givskov, M. (2003) Attenuation of Pseudomonas aeruginosa virulence by quorum sensing inhibitors, EMBO J. 22, 3803-3815.
10. Rumbaugh, K. P., Griswold, J. A., Iglewski, B. H., and Hamood, A. N. (1999) Contribution of quorum sensing to the virulence of Pseudomonas aeruginosa in burn wound infections, Infect Immun 67, 5854-5862.
11. Smith, R. S., Harris, S. G., Phipps, R., and Iglewski, B. (2002) The Pseudomonas aeruginosa quorum-sensing molecule N-(3-oxododecanoyl)homoserine lactone contributes to virulence and induces inflammation in vivo, J Bacteriol 184, 1132-9.
12. Pearson, J. P., Feldman, M., Iglewski, B. H., and Prince, A. (2000) Pseudomonas aeruginosa cell-to-cell signaling is required for virulence in a model of acute pulmonary infection, Infection and Immunity 68, 4331-4334.
13. Wu, H., Song, Z., Givskov, M., Doring, G., Worlitzsch, D., Mathee, K., Rygaard, J., and Hoiby, N. (2001) Pseudomonas aeruginosa mutations in lasI and rhlI quorum sensing systems result in milder chronic lung infection, Microbiology 147, 1105-13.
14. Storey, D. G., Ujack, E. E., Rabin, H. R., and Mitchell, I. (1998) Pseudomonas aeruginosa lasR transcription correlates with the transcription of lasA, lasB, and toxA in chronic lung infections associated with cystic fibrosis, Infect Immun 66, 2521-2528.
15. Erickson, D. L., Endersby, R., Kirkham, A., Stuber, K., Vollman, D. D., Rabin, H. R., Mitchell, I., and Storey, D. G. (2002) Pseudomonas aeruginosa quorum-sensing systems may control virulence factor expression in the lungs of patients with cystic fibrosis, Infection and Immunity 70, 1783-1790.
16. Smith, R. S., and Iglewski, B. H. (2003) Pseudomonas aeruginosa quorum sensing as a potential antimicrobial target, Journal of Clinical Investigation 112, 1460-1465.
17. Gutierrez, J. A., Crowder, T., Rinaldo-Mat this, A., Ho, M.-C., Almo, S. C., and Schramm, V. L. (2009) Transition state analogues of 5'-methylthioadenosine nucleosidase disrupt quorum sensing, Nature Chemical Biology 5, 251-257.
18. Parsek, M. R., Val, D. L., Hanzelka, B. L., Cronan, J. E., Jr., and Greenberg, E. P. (1999) Acyl homoserine-lactone quorum-sensing signal generation, Proc Natl Acad Sci USA 96, 4360-4365.
19. Oberhardt, M. A., Puchalka, J., Fryer, K. E., Martins dos Santos, V. A., and Papin, J. A. (2008) Genome-scale metabolic network analysis of the opportunistic pathogen *Pseudomonas aeruginosa* PAO1, *J Bacteriol* 190, 2790-2803.

20. Sekowska, A., Denervaud, V., Ashida, H., Michoud, K., Haas, D., Yokota, A., and Danchin, A. (2004) Bacterial variations on the methionine salvage pathway, *BMC Microbiology* 4, 9.

21. Singh, V., Lee, J. E., Nunez, S., Howell, P. L., and Schramm, V. L. (2005) Transition state structure of 5'-methylthioadenosine/S-adenosylhomocysteine nucleosidase from *Escherichia coli* and its similarity to transition state analogues, *Biochemistry* 44, 11647-11659.

22. Miles, R. W., Tyler, P. C., Furneaux, R. H., Bagdassarian, C. K., and Schramm, V. L. (1998) One-third-the-sites transition-state inhibitors for purine nucleoside phosphorylase, *Biochemistry* 37, 8615-8621.

23. Singh, V., Evans, G. B., Lenz, D. H., Mason, J. M., Clinch, K., Mee, S., Painter, G. F., Tyler, P. C., Furneaux, R. H., Lee, J. E., Howell, P. L., and Schramm, V. L. (2005) Femtomolar transition state analogue inhibitors of 5'-methylthioadenosine/S-adenosylhomocysteine nucleosidase from *Escherichia coli*, *Journal of Biological Chemistry* 280, 18265-18273.

24. Morrison, J. F., and Walsh, C. T. (1988) The behavior and significance of slow-binding enzyme inhibitors, *Advances in enzymology and related areas of molecular biology* 61, 201-301.

25. (1994) The CCP4 suite: programs for protein crystallography, *Acta Crystallogr D Biol Crystallogr* 50, 760-763.

26. Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., McCoy, A. J., Moriarty, N. W., Oeffner, R., Read, R. J., Richardson, D. C., Richardson, J. S., Terwilliger, T. C., and Zwart, P. H. (2010) PHENIX: a comprehensive Python-based system for macromolecular structure solution, *Acta Crystallogr D Biol Crystallogr* 66, 213-221.

27. Emsley, P., and Cowtan, K. (2004) Coot: model-building tools for molecular graphics, *Acta Crystallogr D Biol Crystallogr* 60, 2126-2132.

28. Potterton, E., Briggs, P., Turkenburg, M., and Dodson, E. (2003) A graphical user interface to the CCP4 program suite, *Acta Crystallogr D Biol Crystallogr* 59, 1131-7.

29. Winsor, G. L., Lo, R., Sui, S. J., Ung, K. S., Huang, S., Cheng, D., Ching, W. K., Hancock, R. E., and Brinkman, F. S. (2005) *Pseudomonas aeruginosa* genome database and PseudoCAP: facilitating community-based, continually updated, genome annotation, *Nucleic Acids Res* 33, D338-343.

30. Carteni-Farina, M., Oliva, A., Romeo, G., Napolitano, G., De Rosa, M., Gambacorta, A., and Zappia, V. (1979) 5'-Methylthioadenosine phosphorylase from *Caldariella acidophila*. Purification and properties, *European J. Biochemistry* 101, 317-324.

31. Zappia, V., Oliva, A., Cacciapuoti, G., Galletti, P., Mignucci, G., and Carteni-Farina, M. (1978) Substrate specificity of 5'-methylthioadenosine phosphorylase from human prostate, *Biochemical Journal* 175, 1043-1050.

32. Stoeckler, J. D., Cambor, C., Kuhns, V., Chu, S. H., and Parks, R. E., Jr. (1982) Inhibitors of purine nucleoside phosphorylase, C(8) and C(5') substitutions, *Biochem Pharmacol* 31, 163-171.

33. Shi, W., Ting, L.-M., Kicska, G. A., Lewandowicz, A., Tyler, P. C., Evans, G. B., Furneaux, R. H., Kim, K., Almo, S. C., and Schramm, V. L. (2004) *Plasmodium falciparum* purine nucleoside phosphorylase: crystal structures, immucillin inhibitors, and dual catalytic function, *Journal of Biological Chemistry* 279, 18103-18106.

34. Ting, L.-M., Shi, W., Lewandowicz, A., Singh, V., Mwakingwe, A., Birck, M. R., Ringia, E. A. T., Bench, G., Madrid, D. C., Tyler, P. C., Evans, G. B., Furneaux, R. H., Schramm, V. L., and Kim, K. (2005) Targeting a novel *Plasmodium falciparum* purine recycling pathway with specific immucillins, *Journal of Biological Chemistry* 280, 9547-9554.

35. Ho, M. C., Shi, W., Rinaldo-Mat this, A., Tyler, P. C., Evans, G. B., Clinch, K., Almo, S. C., and Schramm, V. L. (2010) Four generations of transition-state analogues for human purine nucleoside phosphorylase, *Proc Natl Acad Sci USA* 107, 4805-4812.

36. Stoeckler, J. D., Poirot, A. F., Smith, R. M., Parks, R. E., Jr., Ealick, S. E., Takabayashi, K., and Erion, M. D. (1997) Purine nucleoside phosphorylase. 3. Reversal of purine base specificity by site-directed mutagenesis, *Biochemistry* 36, 11749-11756.

37. Appleby, T. C., Erion, M. D., and Ealick, S. E. (1999) The structure of human 5'-deoxy-5'-methylthioadenosine phosphorylase at 1.7 angstrom resolution provides insights into substrate binding and catalysis, *Structure (London, England)* 1993) 7, 629-641.

38. Murkin, A. S., Clinch, K., Mason, J. M., Tyler, P. C., and Schramm, V. L. (2008) Immucillins in custom catalytic-site cavities, *Bioorganic & Medicinal Chemistry Letters* 18, 5900-5903.

39. Ferro, A. J., Barrett, A., and Shapiro, S. K. (1976) Kinetic properties and the effect of substrate analogues on 5'-methylthioadenosine nucleosidase from *Escherichia coli*, *Biochimica et biophysica acta* 438, 487-494.

40. Guranowski, A. B., Chiang, P. K., and Cantoni, G. L. (1981) 5'-Methylthioadenosine nucleosidase. Purification and characterization of the enzyme from *Lupinus luteus* seeds, *European journal of biochemistry/FEBS* 114, 293-299.

41. Cornell, K. A., Swarts, W. E., Barry, R. D., and Riscoe, M. K. (1996) Characterization of recombinant *Eschericha coli* 5'-methylthioadenosine/S-adenosylhomocysteine nucleosidase: analysis of enzymatic activity and substrate specificity, *Biochemical and biophysical research communications* 228, 724-732.

42. White, M. W., Vandenbark, A. A., Barney, C. L., and Ferro, A. J. (1982) Structural analogues of 5'-methylthioadenosine as substrates and inhibitors of 5'-methylthioadenosine phosphorylase and as inhibitors of human lymphocyte transformation, *Biochemical Pharmacology* 31, 503-507.

43. Marchitto, K. S. (1982) The metabolism of 5'-deoxy-5'-methylthioadenosine in *Saccharomyces cerevisiae*, p 167 pp.

44. Kaneko, K., Fujimori, S., Kumakawa, T., Kamatani, N., and Akaoka, I. (1991) Disturbance in the metabolism of 5'-methylthioadenosine and adenine in patients with neoplastic diseases, and in those with a deficiency in adenine phosphoribosyltransferase, *Metabolism* 40, 918-921.

45. Savarese, T. M., Ghoda, L. Y., Dexter, D. L., and Parks, R. E., Jr. (1983) Conversion of 5'-deoxy-5'-methylthioadenosine and 5'-deoxy-5'-methylthioinosine to methionine in cultured human leukemic cells, *Cancer Research* 43, 4699-4702.

46. Carson, D. A., Willis, E. H., and Kamatani, N. (1983) Metabolism to methionine and growth stimulation by 5'-methylthioadenosine and 5'-methylthioinosine in mammalian cells, *Biochemical and biophysical research communications* 112, 391-397.

47. Evans, G. B., Furneaux, R. H., Gainsford, G. J., Schramm, V. L., and Tyler, P. C. (2000) Synthesis of transition state analogue inhibitors for purine nucleoside phosphorylase and N-riboside hydrolases, *Tetrahedron* 56, 3053-3062.
48. Evans, G. B., Furneaux, R. H., Lewandowicz, A., Schramm, V. L., and Tyler, P. C. (2003) Synthesis of second-generation transition state analogues of human purine nucleoside phosphorylase, *Journal of Medicinal Chemistry* 46, 5271-5276.
49. Lewandowicz, A., Ringia, E. A. T., Ting, L.-M., Kim, K., Tyler, P. C., Evans, G. B., Zubkova, O. V., Mee, S., Painter, G. F., Lenz, D. H., Furneaux, R. H., and Schramm, V. L. (2005) Energetic mapping of transition state analogue interactions with human and *Plasmodium falciparum* purine nucleoside phosphorylases, *Journal of Biological Chemistry* 280, 30320-30328.
50. Lewandowicz, A., and Schramm, V. L. (2004) Transition state analysis for human and *Plasmodium falciparum* purine nucleoside phosphorylases, *Biochemistry* 43, 1458-68.
51. Richard E. Lee, Jr., Gareth J. Warren, L. V. Gusta (Editors) (1995). "Chapter 3, "Ecology of Ice Nucleation—Active Bacteria" by Susan S. Hirano and Christen D. Upper". *Biological Ice Nucleation and Its Applications*. St. Paul, Minn.: APS Press (The American Phytopathological Society). pp. 41-61.
52. Bantia S, Montgomery J A, Johnson H G, Walsh G M. In vivo and in vitro pharmacologic activity of the purine nucleoside phosphorylase inhibitor BCX-34: the role of GTP and dGTP. Immunopharmacology. 1996 October; 35(1):53-63.

What is claimed is:

1. A method for treating an infection caused by bacteria that use 5'-methylthioinosine phosphorylase (MTIP) in a quorum sensing pathway comprising administering to a subject having the infection a sub-growth inhibiting amount of a 5'-methylthioinosine phosphorylase (MTIP) inhibitor,
wherein the MTIP inhibitor has an IC50 value less than 50 nanomolar for MTIP,
wherein the MTIP inhibitor has an IC50 value greater than or equal to 50 nanomolar for human purine nucleoside phosphorylase (PNP),
wherein the MTIP inhibitor has an IC50 value greater than or equal to 50 nanomolar for 5'-methylthioadenosine nucleosidase (MTAN), and
wherein the MTIP inhibitor has an IC50 value greater than or equal to 50 nanomolar for 5'-methylthioadenosine phosphorylase (MTAP).

2. The method of claim 1, wherein the bacteria is *Pseudomonas aeruginosa*, *Pseudomonas syringae* or *Xanthomonas campestris*.

3. The method of claim 1, wherein the MTIP inhibitor comprises a compound having formula (I):

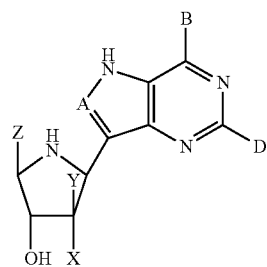

(I)

wherein
A is CH or N;
B is OH;
D is chosen from H, OH, $NH_2$, or $SCH_3$;
X and Y are independently selected from H, OH or halogen, except that when one of X and Y is hydroxy or halogen, the other is hydrogen;
Z is selected from $CH_2SQ$, $CH_2OQ$ or Q, where Q is an optionally substituted alkyl, aralkyl, aralkenyl or aryl group, each of which is optionally substituted with one or more substituents selected from hydroxy, halogen, methoxy, amino, carboxy, or straight- or branched-chain $C_1$-$C_6$ alkyl; provided that Q is not $CH_2OH$;
or a tautomer thereof; or a pharmaceutically acceptable salt thereof; or an ester thereof; or a prodrug thereof.

4. The method of claim 3, wherein the MTIP inhibitor comprises a compound having formula (II):

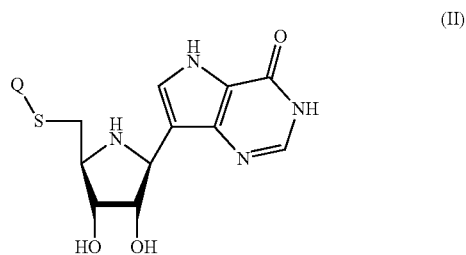

(II)

wherein Q is an optionally substituted alkyl, aralkyl or aryl group, each of which is optionally substituted with one or more substituents selected from hydroxy, halogen, methoxy, amino, carboxy, or straight- or branched-chain $C_1$-$C_6$ alkyl;
or a tautomer thereof; or a pharmaceutically acceptable salt thereof, or an ester thereof; or a prodrug thereof.

5. The method of claim 1, wherein the MTIP inhibitor comprises a compound having formula (III) or formula (IIIa):

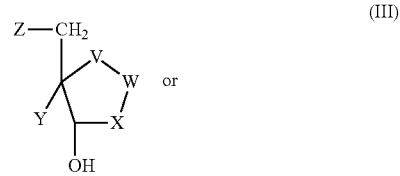

(III)

or

(IIIa)

wherein
V is $CH_2$;
W is $NR^1$;
X is $CH_2$;
Y is selected from hydrogen, halogen and hydroxyl;
Z is selected from hydrogen, halogen, SQ, OQ and Q, where Q is an optionally substituted alkyl, aralkyl or aryl group, each of which is optionally substituted with one or more substituents selected from hydroxy, halogen, methoxy, amino, carboxy, or straight- or branched-chain $C_1$-$C_6$ alkyl;

$R^1$ is a radical of the formula (IV)

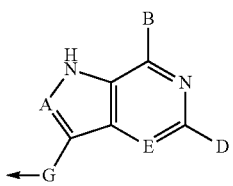

(IV)

A is selected from N, CH and CR, where R is selected from halogen or optionally substituted alkyl, aralkyl or aryl group, each of which is optionally substituted with one or more substituents selected from hydroxy, halogen, methoxy, amino, carboxy, or straight- or branched-chain $C_1$-$C_6$ alkyl;

B is OH;

D is selected from OH, $NH_2$, $SCH_3$ and hydrogen;

E is N;

G is $CH_2$;

or a tautomer thereof or a pharmaceutically acceptable salt thereof or an ester thereof.

6. The method of claim 1, wherein the MTIP inhibitor comprises a compound having formula (VI):

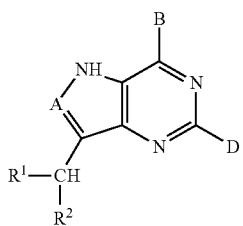

(VI)

wherein $R^1$ is H or $NR^3R^4$;

$R^2$ is H or an alkyl, alkenyl, alkynyl, aralkyl, aralkenyl, aralkynyl, or aryl group, each of which is optionally substituted with one or more hydroxy, alkoxy, thiol, alkylthio, arylthio, aralkylthio, halogen, carboxylic acid, carboxylate alkyl ester, nitro, or $NR^3R^4$ groups, where each alkylthio, arylthio and aralkylthio group is optionally substituted with one or more alkyl, halogen, amino, hydroxy, or alkoxy groups;

provided that when $R^1$ is H, $R^2$ is an alkyl, alkenyl, alkynyl, aralkyl, aralkenyl, aralkynyl, or aryl group which is substituted with at least one $NR^3R^4$ group, and optionally substituted with one or more hydroxy, alkoxy, thiol, alkylthio, arylthio, aralkylthio, halogen, carboxylic acid, carboxylate alkyl ester or nitro group;

$R^3$ and $R^4$, independently of each other, are H or an alkyl, alkenyl, alkynyl, aralkyl, aralkenyl, aralkynyl, or aryl group, each of which is optionally substituted with one or more hydroxy, alkoxy, thiol, alkylthio, arylthio, aralkylthio, halogen, carboxylic acid, carboxylate alkyl ester, nitro, or $NR^3R^4$ groups, where each alkylthio, arylthio and aralkylthio group is optionally substituted with one or more alkyl, halogen, amino, hydroxy, or alkoxy groups;

A is N or CH;

B is OH; and

D is H, OH, $NH_2$, or $SCH_3$;

or a tautomer thereof, or a pharmaceutically acceptable salt thereof, or an ester prodrug form thereof.

7. The method of claim 1, wherein the MTIP inhibitor comprises a compound having formula (VII):

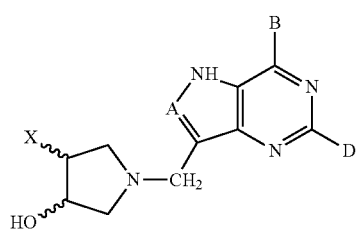

(VII)

wherein

X is an alkyl, cycloalkyl, aralkyl, aralkenyl, alkenyl, alkynyl or aryl group, each of which is optionally substituted with one or more substituents selected from the group consisting of hydroxy, alkoxy, cycloalkyl, thiol, alkylthio, arylthio, aralkylthio, halogen, carboxylic acid, carboxylate alkyl ester, nitro, cyano, thiazole and $NR^2R^3$ group, where each alkylthio, arylthio and aralkylthio group is optionally substituted with one or more alkyl, halogen, amino, hydroxy, or alkoxy groups; or X is $SR^1$; or X is $NR^2R^3$;

$R^1$, $R^2$ and $R^3$ are independently selected from the group consisting of alkyl, alkenyl, alkynyl, aralkyl or aryl, each of which is optionally substituted with one or more substituents selected from the group consisting of hydroxy, alkoxy, thiol, alkylthio, arylthio, aralkylthio, halogen, carboxylic acid, carboxylate alkyl ester, nitro, cyano and $NR^2R^3$ group, where each alkylthio, arylthio and aralkylthio group is optionally substituted with one or more alkyl, halogen, amino, hydroxy, or alkoxy groups;

A is N or CH;

B is OH;

D is H, OH, $NH_2$, or $SCH_3$;

provided that X is not $CH_2Z$, where Z is selected from OH, hydrogen, halogen, $SQ^1$, $OQ^2$ and $Q^3$, where $Q^1$ is an optionally substituted alkyl, aralkyl or aryl group, $Q^2$ is an optionally substituted alkyl group and $Q^3$ is an optionally substituted alkyl group;

or a tautomer thereof, or a pharmaceutically acceptable salt thereof, or an ester prodrug form thereof.

8. The method of claim 1, wherein the sub-growth inhibiting amount of the MTIP inhibitor inhibits quorum sensing in the bacteria.

9. The method of claim 1, wherein the MTIP inhibitor has the formula:

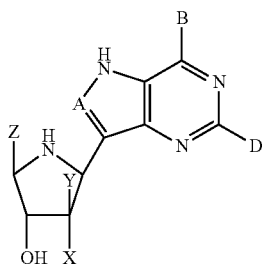

(I)

wherein A is CH or N; B is OH; D is chosen from H, OH, NH₂, or SCH₃; X is OH; Y is H; and Z is Q, where Q is a methyl group which is substituted with one or more substituents selected from the group consisting of methoxy, amino and carboxy, or Q is an optionally substituted, alkenyl, aralkyl, aralkenyl, aryl group or $C_2$-$C_{10}$ alkyl group, each of which is optionally substituted with one or more substituents selected from hydroxy, halogen, methoxy, amino, carboxy, or straight- or branched-chain $C_1$-$C_6$ alkyl; or a tautomer thereof; or a pharmaceutically acceptable salt thereof; or an ester thereof.

10. The method of claim 1, wherein the MTIP inhibitor is selected from the group consisting of:

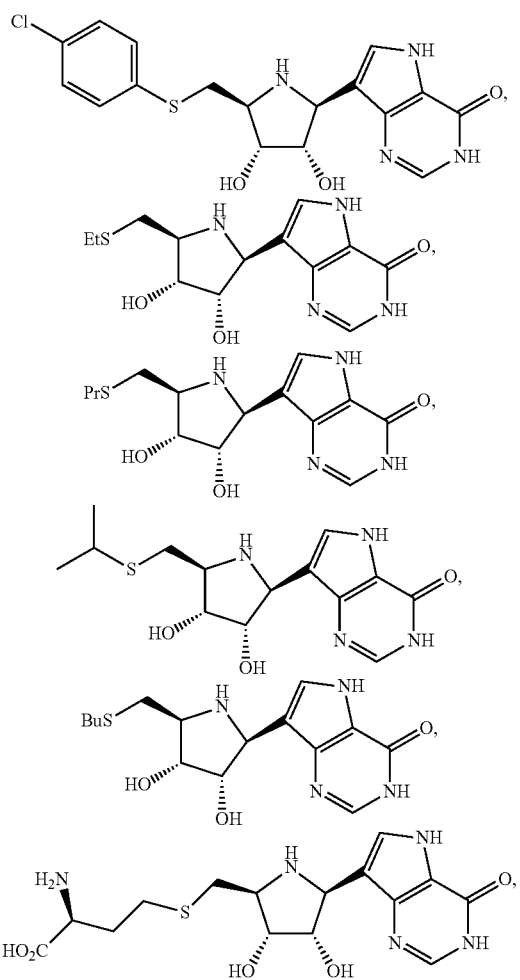

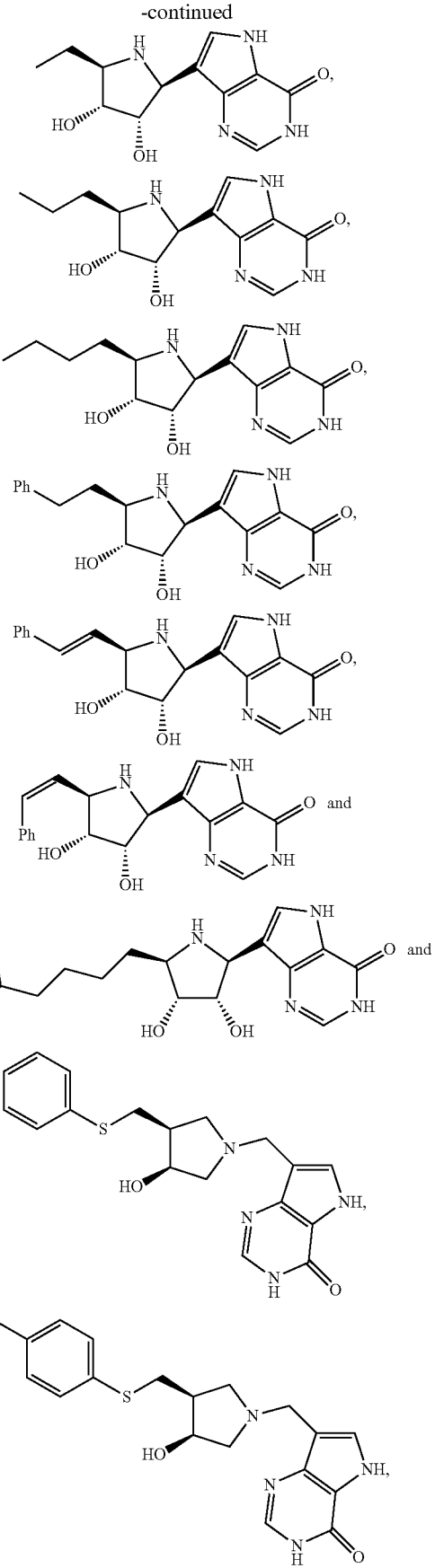

117
-continued
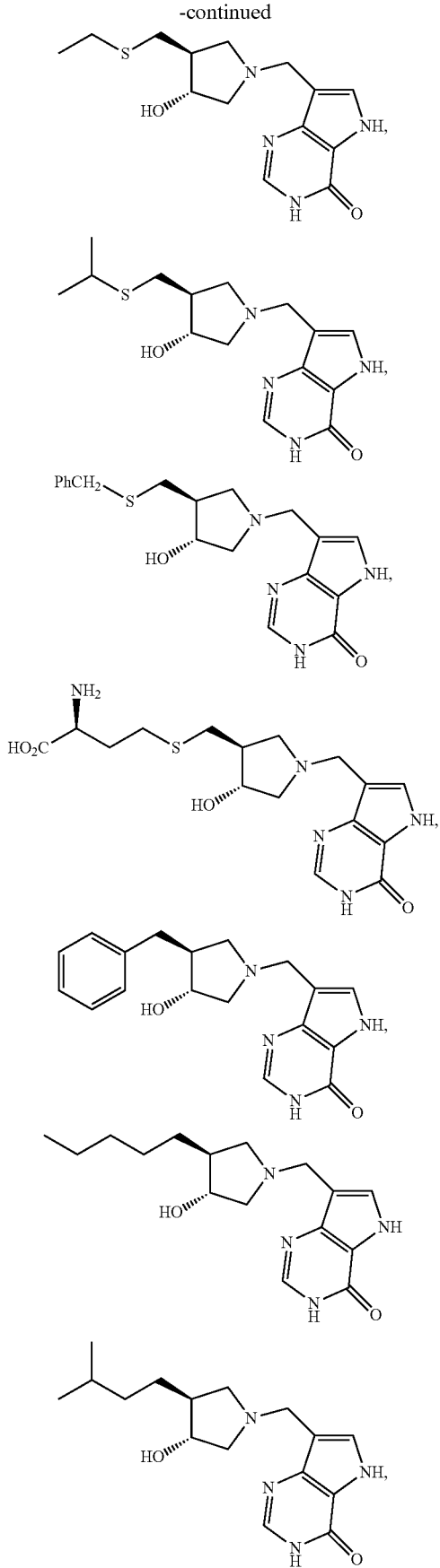
118
-continued
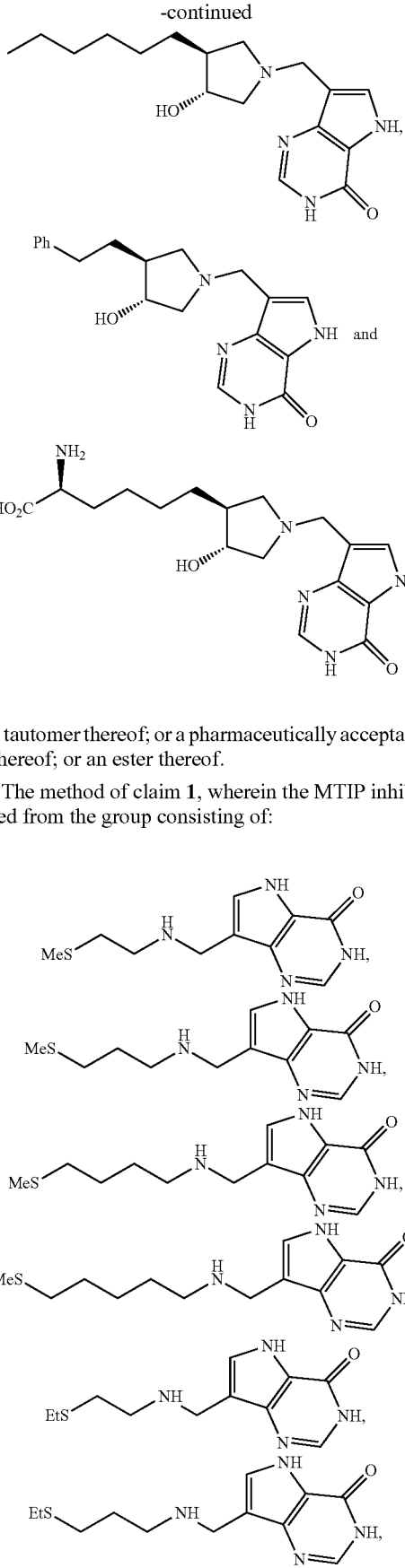
or a tautomer thereof; or a pharmaceutically acceptable salt thereof; or an ester thereof.
11. The method of claim 1, wherein the MTIP inhibitor is selected from the group consisting of:

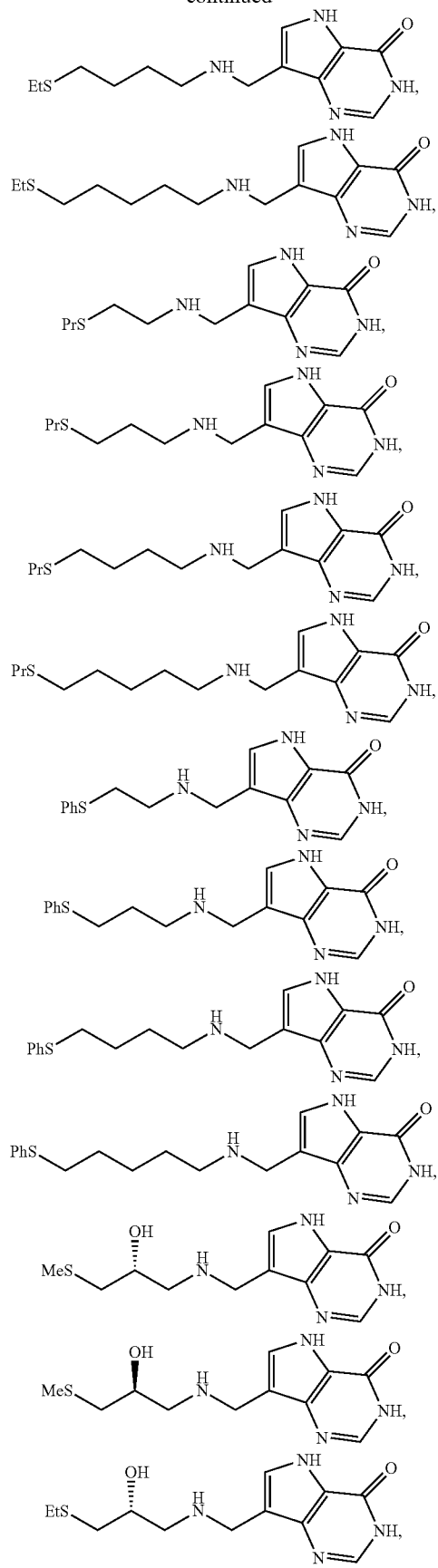
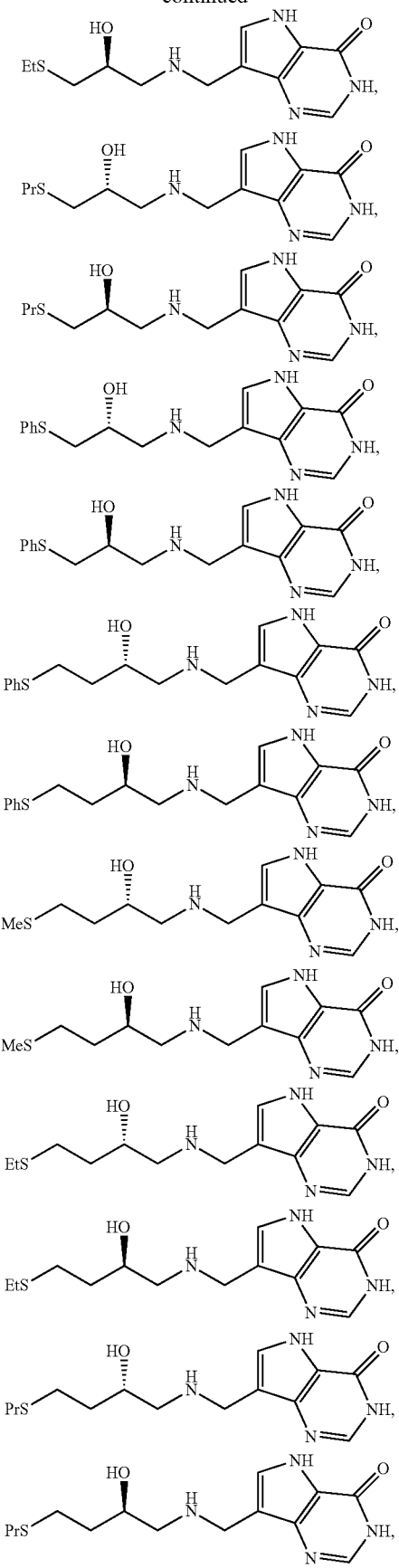

-continued
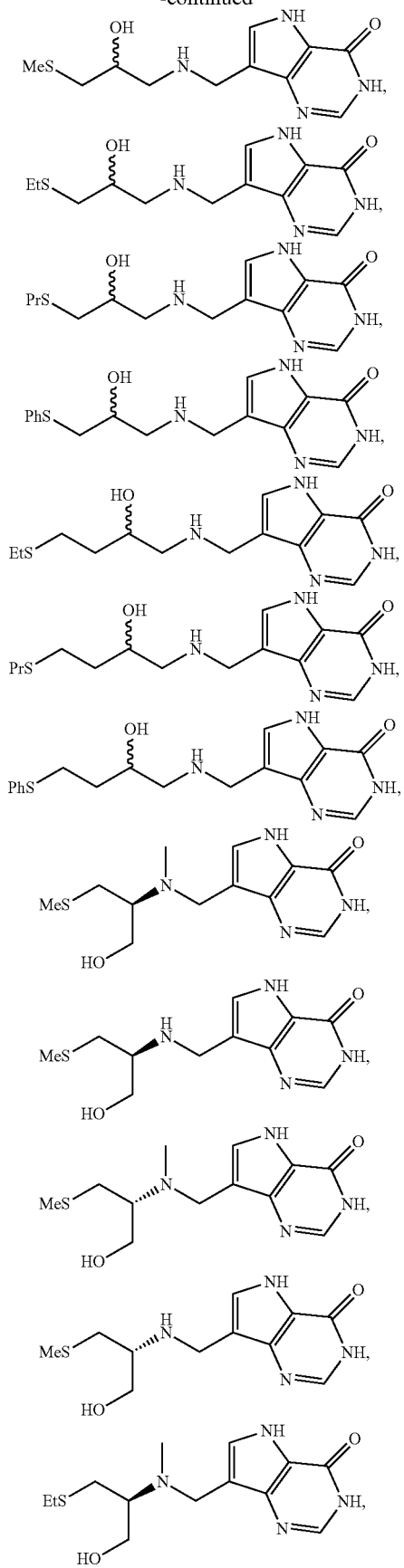
-continued
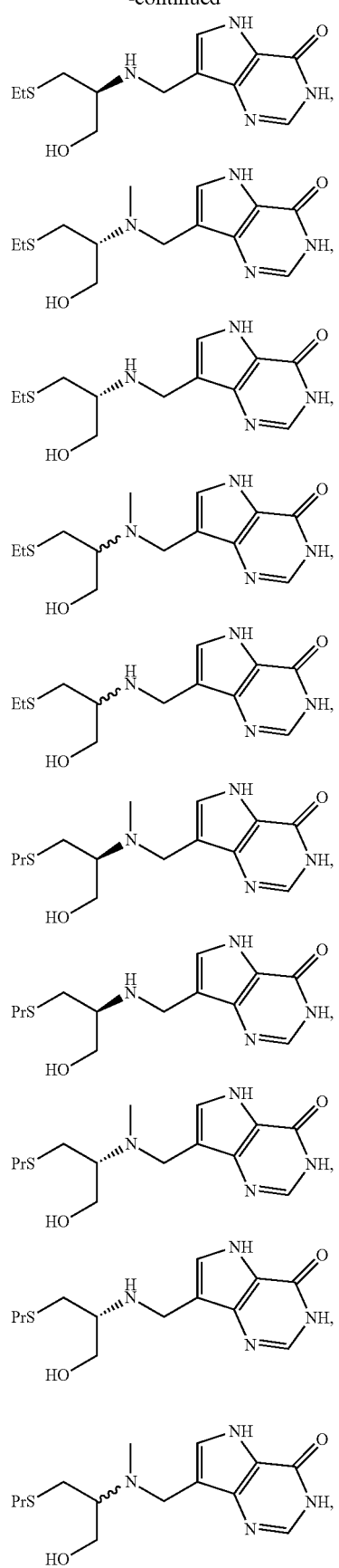

123
-continued
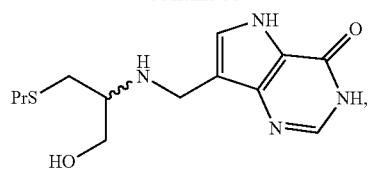
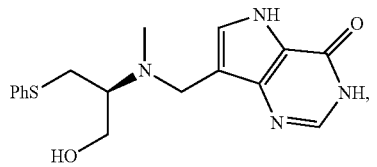
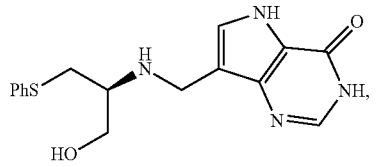
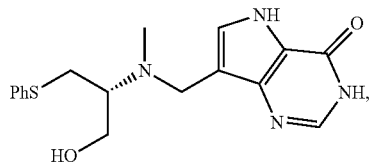
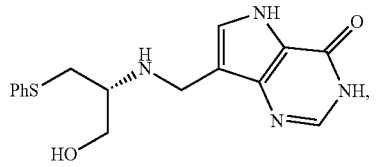
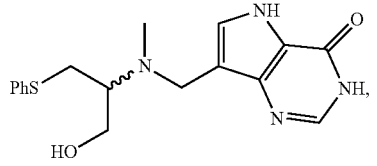
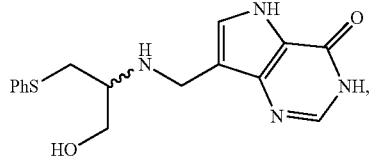
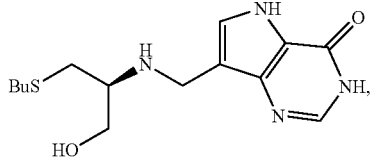
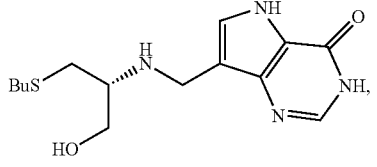
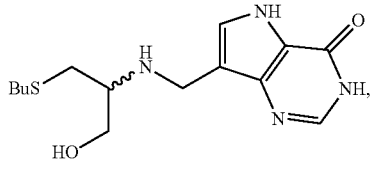
124
-continued
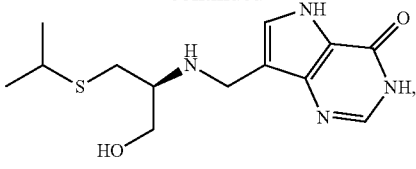
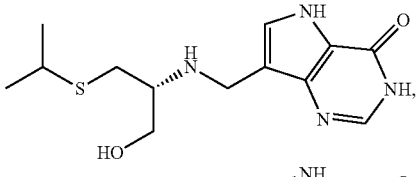
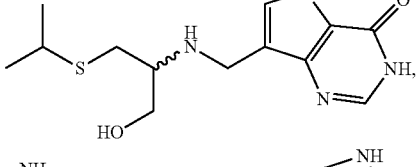
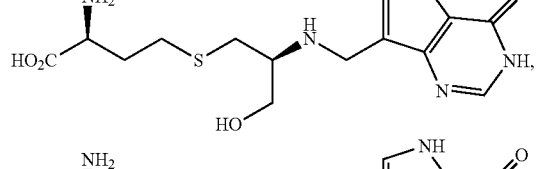
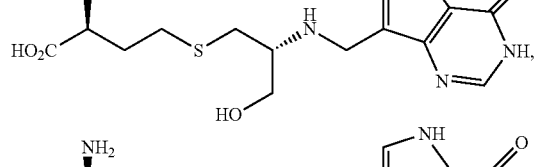
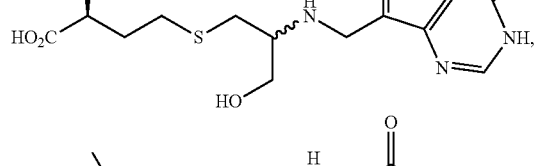
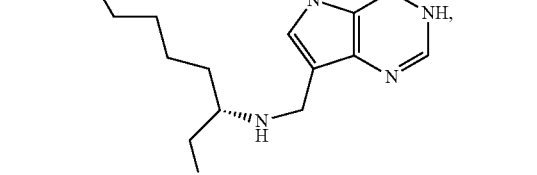
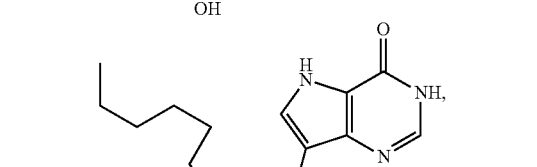
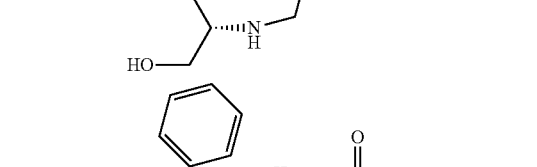
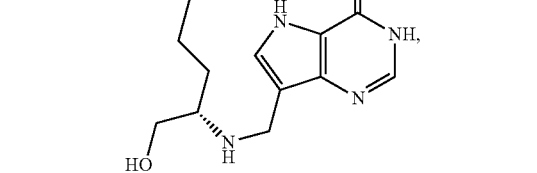

125
-continued
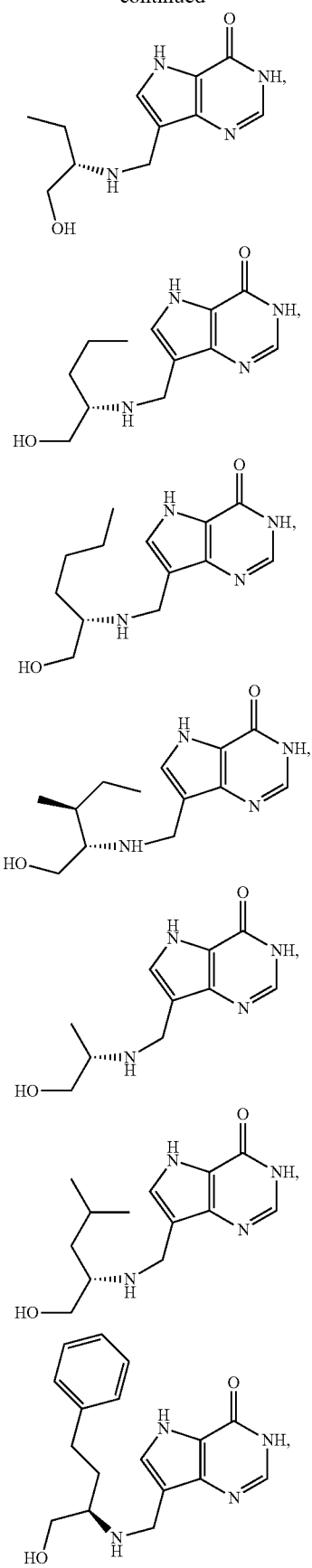
126
-continued
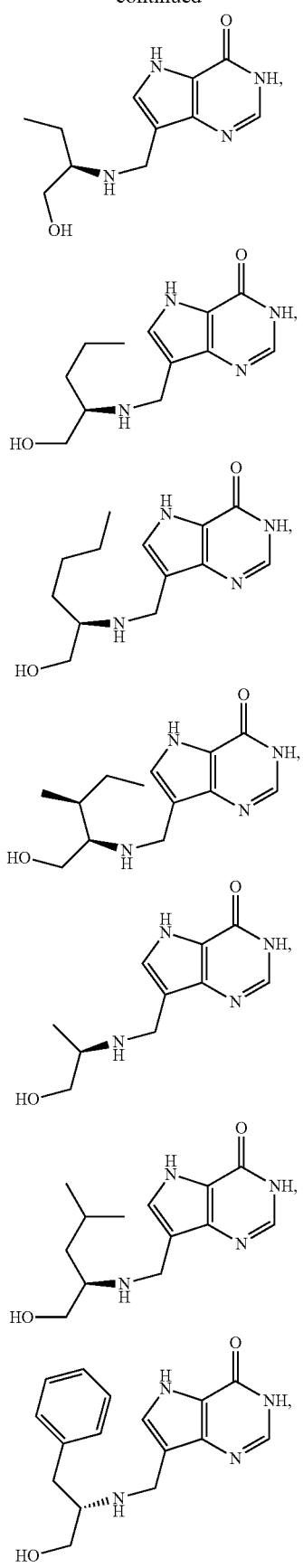

-continued
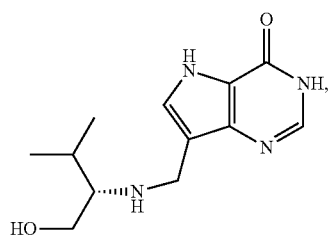
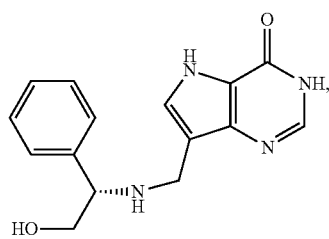
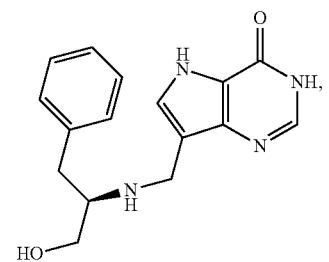
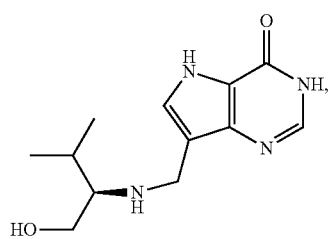
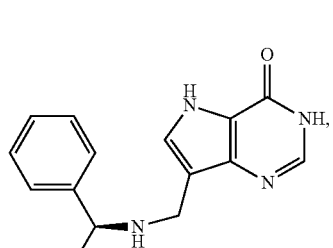
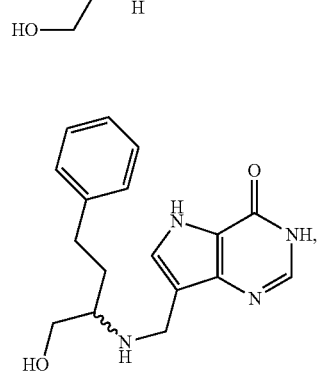
-continued
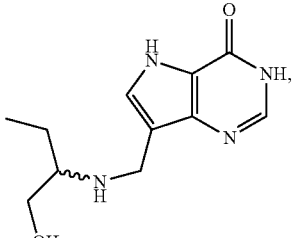
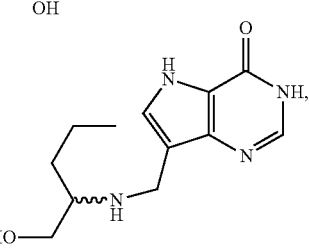
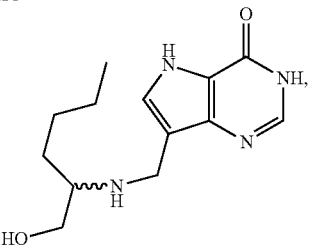
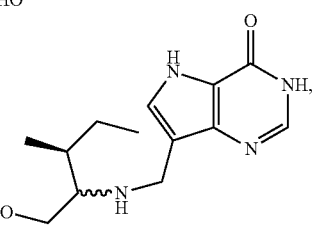
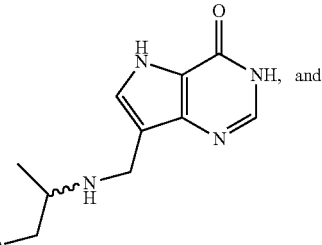, and
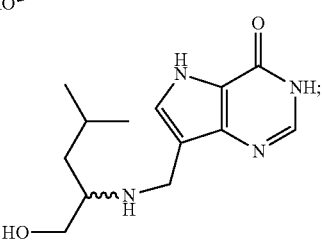
or a tautomer thereof; or a pharmaceutically acceptable salt thereof; or an ester thereof.
12. The method of claim 1, comprising coadministering the 5'-methylthioinosine phosphorylase (MTIP) inhibitor with 5'-methylthioinosine and/or 5'-methylthioadenosine.
* * * * *

SEQUENCE LISTING

<160> NUMBER OF SEQ ID NOS: 12

<210> SEQ ID NO 1
<211> LENGTH: 272
<212> TYPE: PRT
<213> ORGANISM: Escherichia coli

<400> SEQUENCE: 1

```
Phe Ser His Asn Pro Leu Phe Cys Ile Asp Ile Ile Lys Thr Tyr Lys
1               5                   10                  15

Pro Asp Phe Thr Pro Arg Val Ala Phe Ile Leu Gly Ser Gly Leu Gly
            20                  25                  30

Ala Leu Ala Asp Gln Ile Glu Asn Ala Val Ala Ile Ser Tyr Glu Lys
        35                  40                  45

Leu Pro Gly Phe Pro Val Ser Thr Val His Gly His Ala Gly Glu Leu
    50                  55                  60

Val Leu Gly His Leu Gln Gly Val Pro Val Val Cys Met Lys Gly Arg
65                  70                  75                  80

Gly His Phe Tyr Glu Gly Arg Gly Met Thr Ile Met Thr Asp Ala Ile
                85                  90                  95

Arg Thr Phe Lys Leu Leu Gly Cys Glu Leu Leu Phe Cys Thr Asn Ala
            100                 105                 110

Ala Gly Ser Leu Arg Pro Glu Val Gly Ala Gly Ser Leu Val Ala Leu
        115                 120                 125

Lys Asp His Ile Asn Thr Met Pro Gly Thr Pro Met Val Gly Leu Asn
    130                 135                 140

Asp Asp Arg Phe Gly Glu Arg Phe Phe Ser Leu Ala Asn Ala Tyr Asp
145                 150                 155                 160

Ala Glu Tyr Arg Ala Leu Leu Gln Lys Val Ala Lys Glu Glu Gly Phe
                165                 170                 175

Pro Leu Thr Glu Gly Val Phe Val Ser Tyr Pro Gly Pro Asn Phe Glu
            180                 185                 190

Thr Ala Ala Glu Ile Arg Met Met Gln Ile Ile Gly Gly Asp Val Val
        195                 200                 205

Gly Met Ser Val Val Pro Glu Val Ile Ser Ala Arg His Cys Asp Leu
    210                 215                 220

Lys Val Val Ala Val Ser Ala Ile Thr Asn Met Ala Glu Gly Leu Ser
225                 230                 235                 240

Asp Val Lys Leu Ser His Ala Gln Thr Leu Ala Ala Ala Glu Leu Ser
                245                 250                 255
```

-continued

```
Lys Gln Asn Phe Ile Asn Leu Ile Cys Gly Phe Leu Arg Lys Ile Ala
            260                 265                 270

<210> SEQ ID NO 2
<211> LENGTH: 260
<212> TYPE: PRT
<213> ORGANISM: Mycobacterium tuberculosis

<400> SEQUENCE: 2

Asp Glu Leu Ala Arg Arg Ala Ala Gln Val Ile Ala Asp Arg Thr Gly
1               5                   10                  15

Ile Gly Glu His Asp Val Ala Val Val Leu Gly Ser Gly Trp Leu Pro
            20                  25                  30

Ala Val Ala Ala Leu Gly Ser Pro Thr Thr Val Leu Pro Gln Ala Glu
        35                  40                  45

Leu Pro Gly Phe Val Pro Pro Thr Ala Ala Gly His Ala Gly Glu Leu
    50                  55                  60

Leu Ser Val Pro Ile Gly Ala His Arg Val Leu Val Leu Ala Gly Arg
65                  70                  75                  80
Ile His Ala Tyr Glu Gly His Asp Leu Arg Tyr Val Val His Pro Val
                85                  90                  95
Arg Ala Ala Arg Ala Ala Gly Ala Gln Ile Met Val Leu Thr Asn Ala
            100                 105                 110
Ala Gly Gly Leu Arg Ala Asp Leu Gln Val Gly Gln Pro Val Leu Ile
        115                 120                 125
Ser Asp His Leu Asn Leu Thr Ala Arg Ser Pro Leu Val Gly Gly Glu
    130                 135                 140
Phe Val Asp Leu Thr Asp Ala Tyr Ser Pro Arg Leu Arg Glu Leu Ala
145                 150                 155                 160
Arg Gln Ser Asp Pro Gln Leu Ala Glu Gly Val Tyr Ala Gly Leu Pro
                165                 170                 175
Gly Pro His Tyr Glu Thr Pro Ala Glu Ile Arg Met Leu Gln Thr Leu
            180                 185                 190
Gly Ala Asp Leu Val Gly Met Ser Thr Val His Glu Thr Ile Ala Ala
        195                 200                 205
Arg Ala Ala Gly Ala Glu Val Leu Gly Val Ser Leu Val Thr Asn Leu
    210                 215                 220
Ala Ala Gly Ile Thr Gly Glu Pro Leu Ser His Ala Glu Val Leu Ala
225                 230                 235                 240

Ala Gly Ala Ala Ser Ala Thr Arg Met Gly Ala Leu Leu Ala Asp Val
                245                 250                 255
Ile Ala Arg Phe
            260

<210> SEQ ID NO 3
<211> LENGTH: 280
<212> TYPE: PRT
<213> ORGANISM: Grouper iridoviurs

<400> SEQUENCE: 3

Asp Tyr Asp Leu Ala Lys Glu Thr Ala Ala Trp Leu Asn Lys Gln Leu
1               5                   10                  15

Gln Ile Arg Pro Val Leu Gly Ile Val Cys Gly Ser Gly Leu Gly Lys
            20                  25                  30

Ile Gly Asp Ser Leu Glu Thr Ser Ile Thr Val Ala Tyr Ser Asp Ile
        35                  40                  45
```

```
Pro Asn Phe Pro Val Gly Ser Val Lys Gly His Ala Gly Ser Leu Ile
        50                  55                  60

Phe Gly Ser Val Asn Gly Val Ser Cys Val Cys Met Lys Gly Arg Phe
 65                  70                  75                  80

His Leu Tyr Glu Gly His Thr Ala Ala Arg Ala Thr Phe Pro Met Arg
                85                  90                  95

Val Phe Lys Ala Leu Gly Val Lys Ile Val Val Leu Thr Asn Ala Ala
               100                 105                 110

Gly Gly Leu Asn Pro Ser Tyr Arg Pro Gly Asp Phe Met Val Val Arg
               115                 120                 125

Asp His Ile Asn Leu Pro Gly Leu Ala Gly Ala Asn Pro Leu Thr Gly
130                 135                 140

Pro Asn Asp Asp Thr Glu Gly Glu Arg Phe Pro Ser Met Thr Ser Val
145                 150                 155                 160

Tyr Asp Lys Thr Leu Arg Lys Tyr Ala Ile Ser Ala Ala Arg Glu Leu
                165                 170                 175

Gly Met Ser Tyr Ala Thr His Glu Gly Val Tyr Cys Cys Val Asn Gly
               180                 185                 190

Pro Ser Phe Glu Thr Pro Ala Glu Cys Lys Ile Leu Arg Leu Met Gly
               195                 200                 205

Ser Asp Ala Val Gly Met Ser Thr Ala Pro Glu Thr Ile Val Ala Lys
210                 215                 220

His Gly Gly Met Arg Cys Leu Ala Val Ser Leu Ile Ser Asn Val Ile
225                 230                 235                 240

Ala Ser Asn Cys Glu Thr Pro Ala Glu Pro Thr His Glu Glu Val Leu
                245                 250                 255

Arg Ala Gly Glu Glu Ala Ser Ala Arg Met Thr Ala Leu Val Lys Leu
               260                 265                 270

Val Ile Glu Lys Ile Arg Gly Glu
               275                 280

<210> SEQ ID NO 4
<211> LENGTH: 281
<212> TYPE: PRT
<213> ORGANISM: Anopheles gambia

<400> SEQUENCE: 4

Tyr Thr Tyr Asp Thr Leu Gln Glu Ile Ala Thr Tyr Leu Leu Glu Arg
 1               5                  10                  15

Thr Glu Leu Arg Pro Lys Val Gly Ile Ile Cys Gly Ser Gly Leu Gly
                20                  25                  30

Thr Leu Ala Glu Gln Leu Thr Asp Val Asp Ser Phe Asp Tyr Glu Thr
            35                  40                  45

Ile Pro His Phe Pro Val Ser Thr Val Ala Gly His Val Gly Arg Leu
 50                  55                  60

Val Phe Gly Tyr Leu Ala Gly Val Pro Val Met Cys Met Gln Gly Arg
 65                  70                  75                  80

Phe His His Tyr Glu Gly Tyr Pro Leu Ala Lys Cys Ala Met Pro Val
                85                  90                  95

Arg Val Met His Leu Ile Gly Cys Thr His Leu Ile Ala Thr Asn Ala
               100                 105                 110

Ala Gly Gly Ala Asn Pro Lys Tyr Arg Val Gly Asp Ile Met Leu Ile
               115                 120                 125

Lys Asp His Ile Asn Leu Met Gly Phe Ala Gly Asn Asn Pro Leu Gln
130                 135                 140
```

```
Gly Pro Asn Asp Glu Arg Phe Gly Pro Arg Phe Gly Met Ala Asn Thr
145                 150                 155                 160

Tyr Asp Pro Lys Leu Asn Gln Gln Ala Lys Val Ile Ala Arg Gln Ile
                165                 170                 175

Gly Ile Glu Asn Glu Leu Arg Gly Val Tyr Thr Cys Leu Gly Gly
            180                 185                 190

Pro Asn Phe Glu Thr Val Ala Glu Val Lys Met Leu Ser Met Leu Gly
                195                 200                 205

Val Asp Ala Ile Gly Met Ser Thr Val His Glu Ile Thr Ala Arg
210                 215                 220

His Cys Gly Met Thr Cys Phe Ala Phe Ser Leu Ile Thr Asn Met Cys
225                 230                 235                 240

Thr Met Ser Tyr Glu Glu Glu Glu His Cys His Asp Ser Ile Val
                245                 250                 255

Gly Val Gly Lys Asn Arg Glu Lys Thr Leu Gly Glu Phe Val Ser Arg
                260                 265                 270

Ile Val Lys His Ile His Tyr Glu Ala
275                 280
```

<210> SEQ ID NO 5
<211> LENGTH: 265
<212> TYPE: PRT
<213> ORGANISM: Thermotoga maritime

<400> SEQUENCE: 5

```
Met Met Lys Lys Ile Glu Glu Ala Arg Thr Phe Ile Ser Glu Arg Thr
1               5                   10                  15

Asn Leu Ser Pro Asp Ile Leu Ile Ile Leu Gly Ser Gly Phe Gly Pro
                20                  25                  30

Phe Ile Glu Lys Val Glu Asp Pro Val Ile Ile Asp Tyr Lys Asp Ile
                35                  40                  45

Pro His Phe Pro Gln Pro Thr Val Glu Gly His Ser Gly Lys Leu Val
            50                  55                  60

Phe Gly Arg Ile Ser Asp Lys Pro Val Met Ile Met Ala Gly Arg Phe
65                  70                  75                  80

His Leu Tyr Glu Gly His Asp Pro Ala Thr Val Ala Phe Pro Val Tyr
                85                  90                  95

Leu Ala Lys Tyr Val Gly Val Lys Gly Val Val Thr Asn Ala Ala
                100                 105                 110

Gly Ala Ile Asn Pro Glu Phe Lys Pro Gly Glu Ile Ile Leu Val Arg
            115                 120                 125

Asp Ile Ile Asn Phe Met Phe Arg Asn Pro Leu Arg Gly Pro Asn Asp
130                 135                 140

Glu Lys Ile Gly Pro Arg Phe Pro Asp Met Ser Ser Val Val Asp Pro
145                 150                 155                 160

Glu Trp Ala Arg Lys Ile Gln Gly Arg Leu Ser Leu Lys Glu Gly Val
                165                 170                 175

Tyr Ile Gly Val Leu Gly Pro Ser Tyr Glu Thr Pro Ala Glu Ile Arg
            180                 185                 190

Val Phe Glu Lys Leu Gly Ala Asp Leu Val Gly Met Ser Thr Val Pro
                195                 200                 205

Glu Val Ile Ala Ala Lys His Cys Gly Leu Lys Val Val Val Phe Ser
210                 215                 220

Cys Val Thr Asn Met Ala Ala Gly Ile Thr His Gly Arg Leu Ser His
```

-continued

```
                225                 230                 235                 240
Glu Glu Val Val Arg Thr Thr Lys Met Ala Gln Gly Lys Ile Glu Lys
                    245                 250                 255

Ala Leu Thr Thr Ala Val Glu Val Phe
                    260                 265

<210> SEQ ID NO 6
<211> LENGTH: 278
<212> TYPE: PRT
<213> ORGANISM: Bos taurus

<400> SEQUENCE: 6

Tyr Thr Tyr Glu Asp Tyr Gln Asp Thr Ala Lys Trp Leu Leu Ser His
1               5                   10                  15

Thr Glu Gln Arg Pro Gln Val Ala Val Ile Cys Gly Ser Gly Leu Gly
                20                  25                  30

Gly Leu Val Asn Lys Leu Thr Gln Ala Gln Thr Phe Asp Tyr Ser Glu
            35                  40                  45

Ile Pro Asn Phe Pro Glu Ser Thr Val Pro Gly His Ala Gly Arg Leu
        50                  55                  60

Val Phe Gly Ile Leu Asn Gly Arg Ala Cys Val Met Met Gln Gly Arg
65                  70                  75                  80

Phe His Met Tyr Glu Gly Tyr Pro Phe Trp Lys Val Thr Phe Pro Val
                85                  90                  95

Arg Val Phe Arg Leu Leu Gly Val Glu Thr Leu Val Val Thr Asn Ala
                100                 105                 110

Ala Gly Gly Leu Asn Pro Asn Phe Glu Val Gly Asp Ile Met Leu Ile
            115                 120                 125

Arg Asp His Ile Asn Leu Pro Gly Phe Ser Gly Glu Asn Pro Leu Arg
        130                 135                 140

Gly Pro Asn Glu Glu Arg Phe Gly Val Arg Phe Pro Ala Met Ser Asp
145                 150                 155                 160

Ala Tyr Asp Arg Asp Met Arg Gln Lys Ala His Ser Thr Trp Lys Gln
                165                 170                 175

Met Gly Glu Gln Arg Glu Leu Gln Glu Gly Thr Tyr Val Met Leu Gly
                180                 185                 190

Gly Pro Asn Phe Glu Thr Val Ala Glu Cys Arg Leu Leu Arg Asn Leu
            195                 200                 205

Gly Ala Asp Ala Val Gly Met Ser Thr Val Pro Glu Val Ile Val Ala
        210                 215                 220

Arg His Cys Gly Leu Arg Val Phe Gly Phe Ser Leu Ile Thr Asn Lys
225                 230                 235                 240

Val Ile Met Asp Thr Glu Ser Gln Gly Lys Ala Asn His Glu Glu Val
                245                 250                 255

Leu Glu Ala Gly Lys Gln Ala Ala Gln Lys Leu Glu Gln Phe Val Ser
                260                 265                 270

Leu Leu Met Ala Ser Ile
            275

<210> SEQ ID NO 7
<211> LENGTH: 278
<212> TYPE: PRT
<213> ORGANISM: Homo sapiens

<400> SEQUENCE: 7

Tyr Thr Tyr Glu Asp Tyr Lys Asn Thr Ala Glu Trp Leu Leu Ser His
```

```
  1               5                  10                 15
Thr Lys His Arg Pro Gln Val Ala Ile Ile Cys Gly Ser Gly Leu Gly
                20                  25                 30

Gly Leu Thr Asp Lys Leu Thr Gln Ala Gln Ile Phe Asp Tyr Ser Glu
                35                  40                 45

Ile Pro Asn Phe Pro Arg Ser Thr Val Pro Gly His Ala Gly Arg Leu
 50                  55                  60

Val Phe Gly Phe Leu Asn Gly Arg Ala Cys Val Met Met Gln Gly Arg
 65                  70                  75                 80

Phe His Met Tyr Glu Gly Tyr Pro Leu Trp Lys Val Thr Phe Pro Val
                85                  90                 95

Arg Val Phe His Leu Leu Gly Val Asp Thr Leu Val Val Thr Asn Ala
                100                 105                110

Ala Gly Gly Leu Asn Pro Lys Phe Glu Val Gly Asp Ile Met Leu Ile
                115                 120                125

Arg Asp His Ile Asn Leu Pro Gly Phe Ser Gly Gln Asn Pro Leu Arg
                130                 135                140

Gly Pro Asn Asp Glu Arg Phe Gly Asp Arg Phe Pro Ala Met Ser Asp
145                 150                 155                160

Ala Tyr Asp Arg Thr Met Arg Gln Arg Ala Leu Ser Thr Trp Lys Gln
                165                 170                175

Met Gly Glu Gln Arg Glu Leu Gln Glu Gly Thr Tyr Val Met Val Ala
                180                 185                190

Gly Pro Ser Phe Glu Thr Val Ala Glu Cys Arg Val Leu Gln Lys Leu
                195                 200                205

Gly Ala Asp Ala Val Gly Met Ser Thr Val Pro Glu Val Ile Val Ala
                210                 215                220

Arg His Cys Gly Leu Arg Val Phe Gly Phe Ser Leu Ile Thr Asn Lys
225                 230                 235                240

Val Ile Met Asp Tyr Glu Ser Leu Glu Lys Ala Asn His Glu Glu Val
                245                 250                255

Leu Ala Ala Gly Lys Gln Ala Ala Gln Lys Leu Glu Gln Phe Val Ser
                260                 265                270

Ile Leu Met Ala Ser Ile
                275

<210> SEQ ID NO 8
<211> LENGTH: 242
<212> TYPE: PRT
<213> ORGANISM: Pseudomonas aeruginosa

<400> SEQUENCE: 8

Val Tyr Ala Ile Ile Gly Gly Thr Gly Leu Thr Gln Leu Glu Gly Leu
 1               5                  10                 15

Thr Leu Ser Glu Ser Leu Pro Ile Glu Thr Pro Tyr Gly Ala Pro Ser
                20                  25                 30

Ala Pro Leu Gln Arg Gly Arg Tyr Ala Gly Arg Glu Val Leu Phe Leu
                35                  40                 45

Ala Arg His Gly His Pro His Arg Phe Pro Pro His Gln Val Asn Tyr
 50                  55                  60

Arg Ala Asn Leu Trp Ala Leu Lys Gln Ala Gly Ala Glu Ala Val Ile
 65                  70                  75                 80

Ala Val Asn Ala Val Gly Gly Ile His Ala Ala Met Gly Thr Gly His
                85                  90                 95
```

```
Leu Cys Val Pro His Gln Leu Ile Asp Tyr Thr Ser Gly Arg Glu His
                100                 105                 110

Thr Tyr Phe Ala Gly Asp Ile Glu His Val Thr His Ile Asp Phe Ser
            115                 120                 125

His Pro Tyr Asp Glu Pro Leu Arg Gln Arg Leu Ile Glu Ala Leu Arg
        130                 135                 140

Ala Leu Gly Leu Ala His Ser Ser His Gly Val Tyr Ala Cys Thr Gln
145                 150                 155                 160

Gly Pro Arg Leu Glu Thr Val Ala Glu Ile Ala Arg Leu Glu Arg Asp
                165                 170                 175

Gly Asn Asp Ile Val Gly Met Thr Gly Met Pro Glu Ala Ala Leu Ala
            180                 185                 190

Arg Glu Leu Asp Leu Pro Tyr Ala Cys Leu Ala Leu Val Val Asn Pro
        195                 200                 205

Ala Ala Gly Lys Ser Ala Gly Ile Ile Thr Met Ala Glu Ile Glu Gln
210                 215                 220

Ala Leu His Asp Gly Ile Gly Lys Val Arg Glu Val Leu Ala Arg Val
225                 230                 235                 240

Leu Ala

<210> SEQ ID NO 9
<211> LENGTH: 246
<212> TYPE: PRT
<213> ORGANISM: Sulfolobus tokodaii

<400> SEQUENCE: 9

Glu Lys Ala Ser Ile Gly Ile Ile Gly Gly Ser Gly Leu Tyr Asp Pro
1               5                   10                  15

Gln Ile Leu Thr Asn Val Lys Glu Ile Lys Val Tyr Thr Pro Tyr Gly
            20                  25                  30

Glu Pro Ser Asp Asn Ile Ile Leu Gly Glu Leu Glu Gly Arg Lys Val
        35                  40                  45

Ala Phe Leu Pro Arg His Gly Arg Gly His Arg Ile Pro Pro His Lys
50                  55                  60

Ile Asn Tyr Arg Ala Asn Ile Trp Ala Leu Lys Ser Leu Gly Val Lys
65                  70                  75                  80

Trp Val Ile Ala Val Ser Ala Val Gly Ser Leu Arg Leu Asp Tyr Lys
                85                  90                  95

Pro Gly Asp Phe Val Val Pro Asn Gln Phe Ile Asp Met Thr Lys Gly
            100                 105                 110

Arg Thr Tyr Thr Phe Phe Asp Gly Pro Thr Val Ala His Val Ser Met
        115                 120                 125

Ala Asp Pro Phe Cys Glu His Leu Arg Ser Ile Ile Leu Asp Ser Ala
130                 135                 140

Lys Asp Leu Gly Ile Thr Thr His Asp Lys Gly Thr Tyr Ile Cys Ile
145                 150                 155                 160

Glu Gly Pro Arg Phe Ser Thr Arg Ala Glu Ser Ile Val Trp Lys Glu
                165                 170                 175

Val Phe Lys Ala Asp Ile Ile Gly Met Thr Leu Val Pro Glu Val Asn
            180                 185                 190

Leu Ala Cys Glu Ala Glu Met Cys Tyr Ser Val Ile Gly Met Val Thr
        195                 200                 205

Asp Tyr Asp Val Phe Ala Asp Ile Pro Val Thr Ala Glu Glu Val Thr
210                 215                 220
```

```
Lys Val Met Ala Glu Asn Thr Ala Lys Val Lys Leu Leu Tyr Glu
225                 230                 235                 240

Val Ile Arg Arg Leu Pro
                245

<210> SEQ ID NO 10
<211> LENGTH: 252
<212> TYPE: PRT
<213> ORGANISM: Homo sapiens

<400> SEQUENCE: 10

Lys Ile Gly Ile Ile Gly Gly Thr Gly Leu Asp Asp Pro Glu Ile Leu
1               5                   10                  15

Glu Gly Arg Thr Glu Lys Tyr Val Asp Thr Pro Phe Gly Lys Pro Ser
                20                  25                  30

Asp Ala Leu Ile Leu Gly Lys Ile Lys Asn Val Asp Cys Val Leu Leu
            35                  40                  45

Ala Arg His Gly Arg Gln His Thr Ile Met Pro Ser Lys Val Asn Tyr
50                  55                  60

Gln Ala Asn Ile Trp Ala Leu Lys Glu Glu Gly Cys Thr His Val Ile
65                  70                  75                  80

Val Thr Thr Ala Cys Gly Ser Leu Arg Glu Glu Ile Gln Pro Gly Asp
                85                  90                  95

Ile Val Ile Ile Asp Gln Phe Ile Asp Arg Thr Thr Met Arg Pro Gln
            100                 105                 110

Ser Phe Tyr Asp Gly Ser His Ser Cys Ala Arg Gly Val Cys His Ile
        115                 120                 125

Pro Met Ala Glu Pro Phe Cys Pro Lys Thr Arg Glu Val Leu Ile Glu
130                 135                 140

Thr Ala Lys Lys Leu Gly Leu Arg Cys His Ser Lys Gly Thr Met Val
145                 150                 155                 160

Thr Ile Glu Gly Pro Arg Phe Ser Ser Arg Ala Glu Ser Phe Met Phe
                165                 170                 175

Arg Thr Trp Gly Ala Asp Val Ile Asn Met Thr Thr Val Pro Glu Val
            180                 185                 190

Val Leu Ala Lys Glu Ala Gly Ile Cys Tyr Ala Ser Ile Ala Met Ala
        195                 200                 205

Thr Asp Tyr Asp Cys Trp Lys Glu His Glu Glu Ala Val Ser Val Asp
210                 215                 220

Arg Val Leu Lys Thr Leu Lys Glu Asn Ala Asn Lys Ala Lys Ser Leu
225                 230                 235                 240

Leu Leu Thr Thr Ile Pro Gln Ile Gly Ser Thr Glu
                245                 250

<210> SEQ ID NO 11
<211> LENGTH: 256
<212> TYPE: PRT
<213> ORGANISM: Aeropyrum pernix

<400> SEQUENCE: 11

Glu Ile Thr Arg Pro Pro Gly Val Arg Ala His Val Gly Val Ile Gly
1               5                   10                  15

Gly Ser Gly Leu Tyr Asp Pro Gly Ile Val Glu Asn Pro Val Glu Val
                20                  25                  30

Lys Val Ser Thr Pro Tyr Gly Asn Pro Ser Asp Phe Ile Val Val Gly
            35                  40                  45
```

```
Asp Val Ala Gly Val Lys Val Ala Phe Leu Pro Arg His Gly Arg Gly
    50                  55                  60

His Arg Ile Pro Pro His Ala Ile Asn Tyr Arg Ala Asn Ile Trp Ala
65                  70                  75                  80

Leu Lys Ala Leu Gly Val Lys Trp Val Ile Ser Val Ser Ala Val Gly
                85                  90                  95

Ser Leu Arg Glu Asp Tyr Arg Pro Gly Asp Phe Val Val Pro Asp Gln
                100                 105                 110

Phe Ile Asp Met Thr Lys Asn Arg Arg His Tyr Thr Phe Tyr Asp Gly
            115                 120                 125

Pro Val Thr Val His Val Ser Met Ala Asp Pro Phe Cys Glu Asp Leu
        130                 135                 140

Arg Gln Arg Leu Ile Asp Ser Gly Arg Arg Leu Gly Tyr Thr Val His
145                 150                 155                 160

Glu Arg Gly Thr Tyr Val Cys Ile Glu Gly Pro Arg Phe Ser Thr Arg
                165                 170                 175

Ala Glu Ser Arg Val Trp Lys Asp Val Phe Lys Ala Asp Ile Ile Gly
                180                 185                 190

Met Thr Leu Val Pro Glu Ile Asn Leu Ala Cys Glu Ala Gln Leu Cys
            195                 200                 205

Tyr Ala Thr Leu Ala Met Val Thr Asp Tyr Asp Val Trp Ala Asp Arg
        210                 215                 220

Pro Val Thr Ala Glu Glu Val Glu Arg Val Met Ile Ser Asn Val Glu
225                 230                 235                 240

Arg Ala Arg Arg Met Leu Tyr Asp Val Ile Pro Lys Leu Ala Gly Glu
                245                 250                 255

<210> SEQ ID NO 12
<211> LENGTH: 253
<212> TYPE: PRT
<213> ORGANISM: Sulfolobus solfataricus

<400> SEQUENCE: 12

Ile Glu Gln Asn Glu Lys Ala Ser Ile Gly Ile Ile Gly Ser Gly
1               5                   10                  15

Leu Tyr Asp Pro Gly Ile Phe Ser Glu Ser Lys Glu Ile Lys Val Tyr
            20                  25                  30

Thr Pro Tyr Gly Gln Pro Ser Asp Phe Ile Thr Ile Gly Lys Ile Gly
        35                  40                  45

Asn Lys Ser Val Ala Phe Leu Pro Arg His Gly Arg Gly His Arg Ile
    50                  55                  60

Pro Pro His Lys Ile Asn Tyr Arg Ala Asn Ile Trp Ala Leu Lys Glu
65                  70                  75                  80

Leu Gly Val Arg Trp Val Ile Ser Val Ser Ala Val Gly Ser Leu Arg
                85                  90                  95

Met Asp Tyr Lys Leu Gly Asp Phe Val Ile Pro Asp Gln Phe Ile Asp
                100                 105                 110

Met Thr Lys Asn Arg Glu Tyr Ser Phe Phe Asp Gly Pro Val Val Ala
            115                 120                 125

His Val Ser Met Ala Asp Pro Phe Cys Asn Ser Leu Arg Lys Leu Ala
        130                 135                 140

Ile Glu Thr Ala Lys Glu Leu Asn Ile Lys Thr His Glu Ser Gly Thr
145                 150                 155                 160

Tyr Ile Cys Ile Glu Gly Pro Arg Phe Ser Thr Arg Ala Glu Ser Arg
                165                 170                 175
```

```
Thr Trp Arg Glu Val Tyr Lys Ala Asp Ile Ile Gly Met Thr Leu Val
            180                 185                 190

Pro Glu Val Asn Leu Ala Cys Glu Ala Gln Met Cys Tyr Ala Thr Ile
            195                 200                 205

Ala Met Val Thr Asp Tyr Asp Val Phe Ala Glu Ile Pro Val Thr Ala
    210                 215                 220

Glu Glu Val Thr Arg Val Met Ala Glu Asn Thr Glu Lys Ala Lys Lys
225             230                 235                 240

Leu Leu Tyr Ala Leu Ile Gln Lys Leu Pro Glu Lys Pro
                245                 250
```